US008870900B2

(12) United States Patent
Julian et al.

(10) Patent No.: US 8,870,900 B2
(45) Date of Patent: Oct. 28, 2014

(54) ENDOSCOPIC BEATING-HEART STABILIZER AND VESSEL OCCLUSION FASTENER

(75) Inventors: Christopher A. Julian, Los Gatos, CA (US); Michael Ikeda, San Jose, CA (US); Andris D. Ramans, Mountain View, CA (US); Dean F. Hoornaert, Mountain View, CA (US); Margaret M. Isaac, Redwood City, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1857 days.

(21) Appl. No.: 11/689,287

(22) Filed: Mar. 21, 2007

(65) Prior Publication Data
US 2007/0208223 A1 Sep. 6, 2007

Related U.S. Application Data

(60) Division of application No. 09/998,004, filed on Nov. 28, 2001, now Pat. No. 7,250,028, which is a continuation-in-part of application No. 09/436,524, filed on Nov. 9, 1999, now Pat. No. 6,398,726.

(60) Provisional application No. 60/253,484, filed on Nov. 28, 2000, provisional application No. 60/285,641, filed on Apr. 19, 2001, provisional application No. 60/290,556, filed on May 10, 2001.

(51) Int. Cl.
*A61B 17/08* (2006.01)
*A61B 1/32* (2006.01)
(Continued)

(52) U.S. Cl.
CPC ........... *A61B 17/00234* (2013.01); *A61B 17/04* (2013.01); *A61B 17/122* (2013.01);
(Continued)

(58) Field of Classification Search
CPC ................... A61B 18/1442; A61B 2017/306; A61B 2017/0243
USPC ............ 606/151, 157, 158; 128/898; 600/229
See application file for complete search history.

(56) References Cited

U.S. PATENT DOCUMENTS 977,825 A 12/1910 George
1,327,577 A 1/1920 Turner
(Continued)

FOREIGN PATENT DOCUMENTS

DE 9204118 7/1992
DE 4310842 C2 1/1996
(Continued)

OTHER PUBLICATIONS

Adachi, Y., "Touch and trace on the free-form surface of virtual object," *IEEE Research & Development Center*, Suzuki Motor Corp., Japan, (Jan. 1993) pp. 162-168.
(Continued)

*Primary Examiner* — Katherine Dowe
*Assistant Examiner* — Michael Mendoza

(57) ABSTRACT

Devices, systems and methods related to endoscopic surgery, particularly related to robotic surgical operations, provide a tissue stabilizer for endoscopically stabilizing a target tissue within a patient's body. For stabilizing a beating heart during a closed-chest coronary artery bypass grafting procedure, a stabilizer is inserted through an endoscopic cannula and provides sufficient surface area to contact the heart and effectively stabilize the target tissue area. The stabilizer can straddle a blood vessel, such as a coronary artery, which is targeted for an anastomosis. Vessel occlusion fasteners may occlude the target blood vessel prior to the anastomosis procedure.

7 Claims, 45 Drawing Sheets

(51) Int. Cl.
   *A61B 19/00* (2006.01)
   *A61B 17/122* (2006.01)
   *A61B 17/132* (2006.01)
   *A61B 17/04* (2006.01)
   *A61B 17/00* (2006.01)
   *A61B 17/12* (2006.01)
   *A61B 17/29* (2006.01)
   *A61B 17/02* (2006.01)
   *A61B 17/30* (2006.01)

(52) U.S. Cl.
   CPC .............. *A61B 2017/0454* (2013.01); *A61B 2017/00243* (2013.01); *A61B 17/12013* (2013.01); *A61B 2017/2933* (2013.01); *A61B 19/2203* (2013.01); *A61B 2019/2223* (2013.01); *A61B 2017/0243* (2013.01); *A61B 17/0401* (2013.01); *A61B 2017/2932* (2013.01); *A61B 2017/0414* (2013.01); *A61B 2019/2276* (2013.01); *A61B 19/5212* (2013.01); *A61B 2017/0464* (2013.01); *A61B 17/0487* (2013.01); *A61B 19/26* (2013.01); *A61B 2017/306* (2013.01); *A61B 17/0469* (2013.01); *A61B 2017/2905* (2013.01); *A61B 2019/223* (2013.01); *A61B 2017/0404* (2013.01); *A61B 2019/2242* (2013.01); *A61B 17/1327* (2013.01)
   USPC .................... 606/158; 600/229; 128/898

(56) References Cited

U.S. PATENT DOCUMENTS

| | | | |
|---|---|---|---|
| 3,171,549 | A | 3/1965 | Orloff |
| 3,280,991 | A | 10/1966 | Melton et al. |
| 3,497,668 | A | 2/1970 | Hirsch |
| 3,628,535 | A | 12/1971 | Ostrowsky et al. |
| 3,698,791 | A | 10/1972 | Walchle et al. |
| 3,880,166 | A * | 4/1975 | Fogarty ............ 606/158 |
| 3,910,280 | A * | 10/1975 | Talonn ............ 606/203 |
| 3,961,921 | A | 6/1976 | Heiman et al. |
| 3,993,076 | A | 11/1976 | Fogarty |
| 4,041,942 | A | 8/1977 | Dougan et al. |
| 4,058,001 | A | 11/1977 | Waxman |
| 4,062,455 | A | 12/1977 | Flatau |
| 4,078,568 | A | 3/1978 | Etes et al. |
| 4,101,961 | A | 7/1978 | Fletcher et al. |
| 4,128,880 | A | 12/1978 | Cray, Jr. |
| 4,182,311 | A | 1/1980 | Seppi et al. |
| 4,221,997 | A | 9/1980 | Flemming |
| 4,337,045 | A | 6/1982 | Jones et al. |
| 4,349,837 | A | 9/1982 | Hinds |
| 4,367,998 | A | 1/1983 | Causer |
| 4,401,852 | A | 8/1983 | Noso et al. |
| 4,456,961 | A | 6/1984 | Price et al. |
| 4,460,302 | A | 7/1984 | Moreau et al. |
| 4,474,174 | A | 10/1984 | Petruzzi |
| 4,491,135 | A | 1/1985 | Klein |
| 4,503,854 | A | 3/1985 | Jako |
| 4,511,305 | A | 4/1985 | Kawai et al. |
| 4,517,963 | A | 5/1985 | Michel |
| 4,523,884 | A | 6/1985 | Clement et al. |
| 4,586,398 | A | 5/1986 | Yindra |
| 4,598,725 | A | 7/1986 | Brewer |
| 4,604,016 | A | 8/1986 | Joyce |
| 4,614,499 | A | 9/1986 | Arseneault et al. |
| 4,616,637 | A | 10/1986 | Caspari et al. |
| 4,624,011 | A | 11/1986 | Watanabe et al. |
| 4,633,389 | A | 12/1986 | Tanaka et al. |
| 4,635,292 | A | 1/1987 | Mori et al. |
| 4,635,479 | A | 1/1987 | Salisbury, Jr. |
| 4,641,292 | A | 2/1987 | Tunnell et al. |
| 4,649,930 | A | 3/1987 | Groch et al. |
| 4,655,257 | A | 4/1987 | Iwashita |
| 4,655,673 | A | 4/1987 | Hawkes |
| 4,672,963 | A | 6/1987 | Barken |
| 4,676,243 | A | 6/1987 | Clayman |
| 4,728,974 | A | 3/1988 | Nio et al. |
| 4,750,636 | A | 6/1988 | Wortham |
| 4,762,455 | A | 8/1988 | Coughlan et al. |
| 4,764,944 | A | 8/1988 | Finlayson |
| 4,791,934 | A | 12/1988 | Brunnett |
| 4,791,940 | A | 12/1988 | Hirschfeld et al. |
| 4,794,912 | A | 1/1989 | Lia |
| 4,799,779 | A | 1/1989 | Mesmer |
| 4,800,614 | A | 1/1989 | Kopco et al. |
| 4,815,006 | A | 3/1989 | Andersson et al. |
| 4,815,450 | A | 3/1989 | Patel |
| 4,817,592 | A | 4/1989 | Auchinleck et al. |
| 4,819,978 | A | 4/1989 | Scheinman et al. |
| 4,826,392 | A | 5/1989 | Hayati |
| 4,837,734 | A | 6/1989 | Ichikawa et al. |
| 4,852,083 | A | 7/1989 | Niehaus et al. |
| 4,853,874 | A | 8/1989 | Iwamoto et al. |
| 4,854,301 | A | 8/1989 | Nakajima |
| 4,860,215 | A | 8/1989 | Seraji |
| 4,863,133 | A | 9/1989 | Bonnell |
| 4,883,400 | A | 11/1989 | Kuban et al. |
| 4,891,767 | A | 1/1990 | Rzasa et al. |
| 4,930,494 | A | 6/1990 | Takehana et al. |
| 4,942,538 | A | 7/1990 | Yuan et al. |
| 4,942,539 | A | 7/1990 | McGee et al. |
| 4,945,479 | A | 7/1990 | Rusterholz et al. |
| 4,949,717 | A | 8/1990 | Shaw |
| 4,954,952 | A | 9/1990 | Ubhayakar et al. |
| 4,965,417 | A | 10/1990 | Massie |
| 4,969,709 | A | 11/1990 | Sogawa et al. |
| 4,969,890 | A | 11/1990 | Sugita et al. |
| 4,979,933 | A | 12/1990 | Runge |
| 4,979,949 | A | 12/1990 | Matsen, III |
| 4,980,626 | A | 12/1990 | Hess et al. |
| 4,989,253 | A | 1/1991 | Liang et al. |
| 4,996,975 | A | 3/1991 | Nakamura |
| 5,019,968 | A | 5/1991 | Wang et al. |
| 5,020,001 | A | 5/1991 | Yamamoto et al. |
| 5,036,463 | A | 7/1991 | Abela et al. |
| 5,046,022 | A | 9/1991 | Conway et al. |
| 5,046,375 | A | 9/1991 | Salisbury, Jr. |
| 5,053,687 | A | 10/1991 | Merlet |
| 5,053,975 | A | 10/1991 | Tsuchihashi et al. |
| 5,056,031 | A | 10/1991 | Nakano et al. |
| 5,065,741 | A | 11/1991 | Uchiyama et al. |
| 5,078,140 | A | 1/1992 | Kwoh |
| 5,086,401 | A | 2/1992 | Glassman et al. |
| 5,091,656 | A | 2/1992 | Gahn |
| 5,097,829 | A | 3/1992 | Quisenberry |
| 5,097,839 | A | 3/1992 | Allen |
| 5,098,426 | A | 3/1992 | Sklar et al. |
| 5,105,367 | A | 4/1992 | Tsuchihashi et al. |
| 5,109,499 | A | 4/1992 | Inagami et al. |
| 5,119,817 | A | 6/1992 | Allen |
| 5,123,095 | A | 6/1992 | Papadopoulos et al. |
| 5,131,105 | A | 7/1992 | Harrawood et al. |
| 5,142,930 | A | 9/1992 | Allen et al. |
| 5,145,227 | A | 9/1992 | Monford, Jr. |
| 5,166,513 | A | 11/1992 | Keenan et al. |
| 5,175,694 | A | 12/1992 | Amato |
| 5,182,641 | A | 1/1993 | Diner et al. |
| 5,184,319 | A | 2/1993 | Kramer |
| 5,184,601 | A | 2/1993 | Putman |
| 5,186,232 | A | 2/1993 | Zahner |
| 5,187,574 | A | 2/1993 | Kosemura et al. |
| 5,193,963 | A | 3/1993 | McAffee et al. |
| 5,196,688 | A | 3/1993 | Hesse et al. |
| 5,198,894 | A | 3/1993 | Hicks |
| 5,201,325 | A | 4/1993 | McEwen et al. |
| 5,201,743 | A | 4/1993 | Haber et al. |
| 5,210,911 | A | 5/1993 | Brown et al. |
| 5,213,141 | A | 5/1993 | Dorman |
| 5,217,003 | A | 6/1993 | Wilk |
| 5,217,453 | A | 6/1993 | Wilk |
| 5,221,283 | A | 6/1993 | Chang |
| 5,222,499 | A | 6/1993 | Allen et al. |
| 5,228,429 | A | 7/1993 | Hatano |

(56) References Cited

U.S. PATENT DOCUMENTS

| | | |
|---|---|---|
| 5,230,338 A | 7/1993 | Allen et al. |
| 5,230,623 A | 7/1993 | Guthrie et al. |
| 5,231,693 A | 7/1993 | Backes et al. |
| 5,233,516 A | 8/1993 | Le Roux |
| 5,236,432 A | 8/1993 | Matsen, III et al. |
| 5,239,883 A | 8/1993 | Rosheim |
| 5,239,981 A | 8/1993 | Anapliotis |
| 5,240,011 A | 8/1993 | Assa |
| 5,251,127 A | 10/1993 | Raab |
| 5,251,128 A | 10/1993 | Crawford |
| 5,253,289 A | 10/1993 | Tanaka |
| 5,257,999 A | 11/1993 | Slanetz, Jr. |
| 5,271,384 A | 12/1993 | McEwen et al. |
| 5,274,500 A | 12/1993 | Dunn |
| 5,275,608 A | 1/1994 | Forman et al. |
| 5,279,309 A | 1/1994 | Taylor et al. |
| 5,282,806 A | 2/1994 | Haber et al. |
| 5,282,826 A | 2/1994 | Quadri |
| 5,284,130 A | 2/1994 | Ratliff |
| 5,289,273 A | 2/1994 | Lang |
| 5,289,365 A | 2/1994 | Caldwell et al. |
| 5,297,034 A | 3/1994 | Weinstein |
| 5,299,288 A | 3/1994 | Glassman et al. |
| 5,300,926 A | 4/1994 | Stoeckl |
| 5,301,657 A | 4/1994 | Lafferty et al. |
| 5,303,148 A | 4/1994 | Mattson et al. |
| 5,304,149 A | 4/1994 | Morigi |
| 5,304,185 A | 4/1994 | Taylor |
| 5,305,149 A | 4/1994 | Newman et al. |
| 5,305,203 A | 4/1994 | Raab |
| 5,305,427 A | 4/1994 | Nagata |
| 5,309,717 A | 5/1994 | Minch |
| 5,313,306 A | 5/1994 | Kuban et al. |
| 5,320,630 A | 6/1994 | Ahmed |
| 5,321,353 A | 6/1994 | Furness |
| 5,337,732 A | 8/1994 | Grundfest et al. |
| 5,339,799 A | 8/1994 | Kami et al. |
| 5,343,385 A | 8/1994 | Joskowicz et al. |
| 5,343,391 A | 8/1994 | Mushabac |
| 5,345,538 A | 9/1994 | Narayannan et al. |
| 5,357,962 A | 10/1994 | Green |
| 5,368,015 A | 11/1994 | Wilk |
| 5,368,428 A | 11/1994 | Hussey et al. |
| 5,371,536 A | 12/1994 | Yamaguchi |
| 5,382,885 A | 1/1995 | Salcudean et al. |
| 5,388,987 A | 2/1995 | Badoz et al. |
| 5,395,369 A | 3/1995 | McBrayer et al. |
| 5,397,323 A | 3/1995 | Taylor et al. |
| 5,402,801 A | 4/1995 | Taylor |
| 5,403,319 A | 4/1995 | Matsen, III et al. |
| 5,403,332 A | 4/1995 | Christoudias |
| 5,408,409 A | 4/1995 | Glassman et al. |
| 5,410,638 A | 4/1995 | Colgate et al. |
| 5,410,944 A | 5/1995 | Cushman |
| 5,413,092 A | 5/1995 | Williams, III et al. |
| 5,417,210 A | 5/1995 | Funda et al. |
| 5,417,701 A | 5/1995 | Holmes |
| 5,422,521 A | 6/1995 | Neer et al. |
| 5,423,648 A | 6/1995 | Akeel et al. |
| 5,429,142 A | 7/1995 | Szabo et al. |
| 5,431,645 A | 7/1995 | Smith et al. |
| 5,434,457 A | 7/1995 | Josephs et al. |
| 5,441,042 A | 8/1995 | Putman |
| 5,442,728 A | 8/1995 | Kaufman et al. |
| 5,443,484 A | 8/1995 | Kirsch et al. |
| 5,445,166 A | 8/1995 | Taylor |
| 5,451,852 A | 9/1995 | Gusakov |
| 5,451,924 A | 9/1995 | Massimino et al. |
| 5,452,733 A | 9/1995 | Sterman et al. |
| 5,453,686 A | 9/1995 | Anderson |
| 5,454,827 A | 10/1995 | Aust et al. |
| 5,455,766 A | 10/1995 | Scheller et al. |
| 5,458,547 A | 10/1995 | Teraoka et al. |
| 5,458,574 A | 10/1995 | Machold et al. |
| 5,464,410 A | 11/1995 | Skeens et al. |
| 5,467,223 A | 11/1995 | Cleveland, Jr. et al. |
| 5,474,571 A | 12/1995 | Lang |
| 5,476,010 A | 12/1995 | Fleming et al. |
| 5,478,351 A | 12/1995 | Meade et al. |
| 5,489,292 A | 2/1996 | Tovey et al. |
| 5,490,117 A | 2/1996 | Oda et al. |
| 5,490,843 A | 2/1996 | Hildwein et al. |
| 5,506,912 A | 4/1996 | Nagasaki et al. |
| 5,512,919 A | 4/1996 | Araki |
| 5,514,157 A | 5/1996 | Nicholas et al. |
| 5,515,478 A | 5/1996 | Wang |
| 5,524,180 A | 6/1996 | Wang et al. |
| 5,531,520 A | 7/1996 | Grimson et al. |
| 5,544,654 A | 8/1996 | Murphy et al. |
| 5,553,198 A | 9/1996 | Wang et al. |
| 5,562,503 A | 10/1996 | Ellman et al. |
| 5,571,110 A | 11/1996 | Matsen, III |
| 5,572,999 A | 11/1996 | Funda et al. |
| 5,588,432 A | 12/1996 | Crowley |
| 5,597,146 A | 1/1997 | Putman |
| 5,608,847 A | 3/1997 | Pryor |
| 5,609,560 A | 3/1997 | Ichikawa et al. |
| 5,613,937 A | 3/1997 | Garrison et al. |
| 5,626,595 A | 5/1997 | Sklar et al. |
| 5,629,594 A | 5/1997 | Jacobus et al. |
| 5,630,431 A | 5/1997 | Taylor |
| 5,631,973 A | 5/1997 | Green |
| 5,636,259 A | 6/1997 | Khutoryansky et al. |
| 5,647,361 A | 7/1997 | Damadian |
| 5,649,956 A | 7/1997 | Jensen et al. |
| 5,657,429 A | 8/1997 | Wang et al. |
| 5,658,250 A | 8/1997 | Blomquist et al. |
| 5,676,673 A | 10/1997 | Ferre et al. |
| 5,693,071 A | 12/1997 | Gorecki et al. |
| 5,695,500 A | 12/1997 | Taylor et al. |
| 5,696,574 A | 12/1997 | Schwaegerle |
| 5,696,837 A | 12/1997 | Green |
| 5,697,939 A | 12/1997 | Kubota et al. |
| 5,715,729 A | 2/1998 | Toyama et al. |
| 5,715,836 A | 2/1998 | Kliegis et al. |
| 5,718,038 A | 2/1998 | Takiar et al. |
| 5,727,569 A | 3/1998 | Benetti et al. |
| 5,735,290 A | 4/1998 | Sterman et al. |
| 5,737,500 A | 4/1998 | Seraji et al. |
| 5,737,506 A | 4/1998 | McKenna et al. |
| 5,737,711 A | 4/1998 | Abe |
| 5,738,649 A | 4/1998 | Macoviak |
| 5,740,699 A | 4/1998 | Ballantyne et al. |
| 5,740,802 A | 4/1998 | Nafis et al. |
| 5,743,884 A | 4/1998 | Hasson et al. |
| 5,744,363 A | 4/1998 | Hasson |
| 5,748,767 A | 5/1998 | Raab |
| 5,749,362 A | 5/1998 | Funda et al. |
| 5,749,892 A | 5/1998 | Vierra et al. |
| 5,754,741 A | 5/1998 | Wang et al. |
| 5,762,458 A | 6/1998 | Wang et al. |
| 5,765,565 A | 6/1998 | Adair |
| 5,766,126 A | 6/1998 | Anderson |
| 5,769,640 A | 6/1998 | Jacobus et al. |
| 5,776,126 A | 7/1998 | Wilk et al. |
| 5,778,889 A | 7/1998 | Jascomb |
| 5,779,623 A | 7/1998 | Bonnell |
| 5,784,542 A | 7/1998 | Ohm et al. |
| 5,791,908 A | 8/1998 | Gillio |
| 5,792,045 A | 8/1998 | Adair |
| 5,792,135 A | 8/1998 | Madhani et al. |
| 5,792,178 A | 8/1998 | Welch et al. |
| 5,797,900 A | 8/1998 | Madhani et al. |
| 5,800,179 A | 9/1998 | Bailey |
| 5,800,423 A | 9/1998 | Jensen |
| 5,807,243 A | 9/1998 | Vierra et al. |
| 5,807,284 A | 9/1998 | Foxlin |
| 5,807,377 A | 9/1998 | Madhani et al. |
| 5,807,378 A | 9/1998 | Jensen et al. |
| 5,807,379 A | 9/1998 | Lesperance, Jr. |
| 5,808,665 A | 9/1998 | Green |
| 5,810,880 A | 9/1998 | Jensen et al. |
| 5,813,813 A | 9/1998 | Daum et al. |
| 5,814,038 A | 9/1998 | Jensen et al. |

(56) References Cited

U.S. PATENT DOCUMENTS

| | | |
|---|---|---|
| 5,815,640 A | 9/1998 | Wang et al. |
| 5,817,084 A | 10/1998 | Jensen |
| 5,825,862 A | 10/1998 | Voit et al. |
| 5,825,908 A | 10/1998 | Pieper et al. |
| 5,825,982 A | 10/1998 | Wright et al. |
| 5,827,319 A | 10/1998 | Carlson et al. |
| 5,828,197 A | 10/1998 | Martin et al. |
| 5,828,813 A | 10/1998 | Ohm |
| 5,836,869 A | 11/1998 | Kudo et al. |
| 5,844,824 A | 12/1998 | Newman et al. |
| 5,855,553 A | 1/1999 | Tajima et al. |
| 5,855,583 A | 1/1999 | Wang et al. |
| 5,859,934 A | 1/1999 | Green |
| 5,860,420 A | 1/1999 | Wiedner et al. |
| 5,860,985 A | 1/1999 | Anschutz |
| 5,860,995 A | 1/1999 | Berkelaar |
| 5,865,730 A * | 2/1999 | Fox et al. .................... 600/228 |
| 5,867,210 A | 2/1999 | Rod |
| 5,876,325 A | 3/1999 | Mizuno et al. |
| 5,878,193 A | 3/1999 | Wang et al. |
| 5,882,206 A | 3/1999 | Gillio |
| 5,885,583 A | 3/1999 | Miyazaki et al. |
| 5,887,121 A | 3/1999 | Funda et al. |
| 5,894,843 A | 4/1999 | Benetti et al. |
| 5,898,599 A | 4/1999 | Massie et al. |
| 5,904,702 A | 5/1999 | Ek et al. |
| 5,906,630 A | 5/1999 | Anderhub et al. |
| 5,907,664 A | 5/1999 | Wang et al. |
| 5,911,036 A | 6/1999 | Wright et al. |
| 5,920,395 A | 7/1999 | Schulz |
| 5,923,770 A | 7/1999 | O'Donnell et al. |
| 5,931,832 A | 8/1999 | Jensen |
| 5,938,678 A | 8/1999 | Zirps et al. |
| 5,950,629 A | 9/1999 | Taylor et al. |
| 5,951,475 A | 9/1999 | Gueziec et al. |
| 5,951,587 A | 9/1999 | Qureshi et al. |
| 5,954,692 A | 9/1999 | Smith et al. |
| 5,954,731 A | 9/1999 | Yoon |
| 5,957,831 A | 9/1999 | Adair |
| 5,957,902 A | 9/1999 | Teves |
| 5,971,976 A | 10/1999 | Wang |
| 5,976,122 A | 11/1999 | Madhani et al. |
| 5,980,782 A | 11/1999 | Hershkowitz et al. |
| 5,984,932 A | 11/1999 | Yoon |
| 6,001,108 A | 12/1999 | Wang et al. |
| 6,001,111 A | 12/1999 | Sepetka et al. |
| 6,013,027 A | 1/2000 | Khan et al. |
| 6,017,304 A | 1/2000 | Vierra et al. |
| 6,019,722 A | 2/2000 | Spence et al. |
| 6,024,695 A | 2/2000 | Taylor et al. |
| 6,033,362 A | 3/2000 | Cohn |
| 6,036,641 A | 3/2000 | Taylor et al. |
| 6,038,641 A | 3/2000 | Zangenehpour |
| 6,050,266 A | 4/2000 | Benetti et al. |
| 6,063,021 A | 5/2000 | Hossain |
| 6,080,181 A | 6/2000 | Jensen et al. |
| 6,102,850 A | 8/2000 | Wang et al. |
| 6,102,854 A | 8/2000 | Cartier et al. |
| 6,106,511 A | 8/2000 | Jensen |
| 6,113,534 A | 9/2000 | Koros et al. |
| 6,120,433 A | 9/2000 | Mizuno et al. |
| 6,132,368 A | 10/2000 | Cooper |
| 6,132,441 A | 10/2000 | Grace |
| 6,149,583 A | 11/2000 | Vierra et al. |
| 6,196,081 B1 | 3/2001 | Yau |
| 6,197,017 B1 | 3/2001 | Brock et al. |
| 6,201,984 B1 | 3/2001 | Funda et al. |
| 6,205,716 B1 | 3/2001 | Peltz |
| 6,206,903 B1 | 3/2001 | Ramans |
| 6,210,323 B1 | 4/2001 | Gilhuly |
| 6,213,124 B1 | 4/2001 | Butterworth |
| 6,223,100 B1 | 4/2001 | Green |
| 6,226,566 B1 | 5/2001 | Funda et al. |
| 6,231,526 B1 | 5/2001 | Taylor et al. |
| 6,231,585 B1 | 5/2001 | Takahashi et al. |
| 6,244,809 B1 | 6/2001 | Wang et al. |
| 6,246,200 B1 | 6/2001 | Blumenkranz et al. |
| 6,246,898 B1 | 6/2001 | Vesely et al. |
| 6,254,532 B1 | 7/2001 | Paolitto et al. |
| 6,259,806 B1 | 7/2001 | Green |
| 6,270,453 B1 | 8/2001 | Sakai |
| 6,292,712 B1 | 9/2001 | Bullen |
| 6,307,285 B1 | 10/2001 | Delson et al. |
| 6,309,397 B1 | 10/2001 | Julian et al. |
| 6,312,435 B1 | 11/2001 | Wallace et al. |
| 6,330,837 B1 | 12/2001 | Charles et al. |
| 6,331,181 B1 | 12/2001 | Tierney et al. |
| 6,346,072 B1 | 2/2002 | Cooper |
| 6,346,077 B1 | 2/2002 | Taylor et al. |
| 6,364,888 B1 | 4/2002 | Niemeyer et al. |
| 6,368,332 B1 | 4/2002 | Salcudean et al. |
| 6,371,952 B1 | 4/2002 | Madhani et al. |
| 6,398,726 B1 | 6/2002 | Ramans |
| 6,402,737 B1 | 6/2002 | Tajima et al. |
| 6,424,885 B1 | 7/2002 | Niemeyer et al. |
| 6,436,107 B1 | 8/2002 | Wang et al. |
| 6,459,926 B1 | 10/2002 | Nowlin et al. |
| 6,464,691 B1 | 10/2002 | Castaneda |
| 6,468,265 B1 | 10/2002 | Evans et al. |
| 6,470,236 B2 | 10/2002 | Ohtsuki |
| 6,490,490 B1 | 12/2002 | Uchikubo et al. |
| 6,496,099 B2 | 12/2002 | Wang et al. |
| 6,522,906 B1 | 2/2003 | Salisbury, Jr. et al. |
| 6,549,926 B1 | 4/2003 | Kalambur et al. |
| 6,574,355 B2 | 6/2003 | Green |
| 6,574,503 B2 | 6/2003 | Ferek-Petric |
| 6,589,164 B1 | 7/2003 | Flaherty |
| 6,646,541 B1 | 11/2003 | Wang et al. |
| 6,659,939 B2 | 12/2003 | Moll |
| 6,699,177 B1 | 3/2004 | Laby et al. |
| 6,699,235 B2 | 3/2004 | Wallace et al. |
| 6,714,839 B2 | 3/2004 | Salisbury et al. |
| 6,720,988 B1 | 4/2004 | Gere et al. |
| 6,728,599 B2 | 4/2004 | Wang et al. |
| 6,740,028 B2 | 5/2004 | Boone |
| 6,764,445 B2 | 7/2004 | Ramans et al. |
| 6,793,669 B2 | 9/2004 | Nakamura et al. |
| 6,799,065 B1 | 9/2004 | Niemeyer |
| 6,817,972 B2 | 11/2004 | Snow |
| 6,837,883 B2 | 1/2005 | Moll et al. |
| 6,852,107 B2 | 2/2005 | Wang et al. |
| 6,858,003 B2 | 2/2005 | Evans et al. |
| 6,905,460 B2 | 6/2005 | Wang et al. |
| 6,936,001 B1 | 8/2005 | Snow |
| 6,951,535 B2 | 10/2005 | Ghodoussi et al. |
| 7,083,571 B2 | 8/2006 | Wang et al. |
| 7,087,049 B2 | 8/2006 | Nowlin et al. |
| 7,250,028 B2 | 7/2007 | Julian et al. |
| 7,413,565 B2 | 8/2008 | Wang et al. |
| 7,682,357 B2 | 3/2010 | Ghodoussi et al. |
| 7,695,481 B2 | 4/2010 | Wang et al. |
| 7,806,891 B2 | 10/2010 | Nowlin et al. |
| 7,865,266 B2 | 1/2011 | Moll et al. |
| RE43,049 E | 12/2011 | Grace |
| 8,105,235 B2 | 1/2012 | Ramans et al. |
| 8,241,306 B2 | 8/2012 | Grace |
| 8,292,916 B2 | 10/2012 | Grace |
| 8,489,235 B2 | 7/2013 | Moll et al. |
| 8,504,201 B2 | 8/2013 | Moll et al. |
| 8,527,094 B2 | 9/2013 | Kumar et al. |
| 8,600,551 B2 | 12/2013 | Itkowitz et al. |
| 8,666,544 B2 | 3/2014 | Moll et al. |
| 2002/0062435 A1 | 5/2002 | Nemirovsky et al. |
| 2002/0140665 A1 | 10/2002 | Gordon |
| 2003/0083648 A1 | 5/2003 | Wang et al. |
| 2005/0107808 A1 | 5/2005 | Evans et al. |
| 2005/0228365 A1 | 10/2005 | Wang et al. |
| 2008/0046122 A1 | 2/2008 | Manzo et al. |
| 2008/0228196 A1 | 9/2008 | Wang et al. |
| 2008/0312668 A1 | 12/2008 | Grace |
| 2009/0099576 A1 | 4/2009 | Wang et al. |
| 2010/0225209 A1 | 9/2010 | Goldberg et al. |
| 2010/0228249 A1 | 9/2010 | Mohr et al. |
| 2011/0112571 A1 | 5/2011 | Grace |

(56) References Cited

U.S. PATENT DOCUMENTS

| | | |
|---|---|---|
| 2012/0123217 A1 | 5/2012 | Ramans et al. |
| 2013/0304256 A1 | 11/2013 | Moll et al. |
| 2013/0331859 A1 | 12/2013 | Kumar et al. |

FOREIGN PATENT DOCUMENTS

| | | |
|---|---|---|
| DE | 69735708 T2 | 9/2006 |
| EP | 239409 | 9/1987 |
| EP | 424687 | 5/1991 |
| EP | 0494343 A2 | 7/1992 |
| EP | 494943 | 8/1995 |
| EP | 1083830 A1 | 3/2001 |
| EP | 0776738 B1 | 4/2002 |
| EP | 2016908 A2 | 1/2009 |
| EP | 1131004 B1 | 10/2009 |
| EP | 2138105 A2 | 12/2009 |
| EP | 2298222 A2 | 3/2011 |
| JP | H11262492 A | 9/1999 |
| WO | WO-9104711 | 4/1991 |
| WO | WO-9220295 | 11/1992 |
| WO | WO-9313916 A1 | 7/1993 |
| WO | WO-9418881 A1 | 9/1994 |
| WO | WO-9426167 | 11/1994 |
| WO | WO 95/01757 | 1/1995 |
| WO | WO-9715240 A1 | 5/1997 |
| WO | WO-9729690 | 8/1997 |
| WO | WO-9817182 A1 | 4/1998 |
| WO | WO-9825666 A1 | 6/1998 |
| WO | WO-9848704 A1 | 11/1998 |
| WO | WO 99/09892 | 3/1999 |
| WO | WO-9916367 A1 | 4/1999 |
| WO | WO 99/50721 | 10/1999 |
| WO | WO-0007503 A1 | 2/2000 |
| WO | WO0015119 A2 | 3/2000 |
| WO | WO-0030548 A1 | 6/2000 |
| WO | WO-0030551 A1 | 6/2000 |
| WO | WO-0033726 A1 | 6/2000 |
| WO | WO-0015119 A9 | 8/2000 |
| WO | WO-0030548 B1 | 9/2000 |
| WO | WO-0059384 A1 | 10/2000 |
| WO | WO-0030551 A9 | 11/2000 |
| WO | WO-0015119 A3 | 5/2001 |
| WO | WO-0030548 A8 | 7/2001 |
| WO | WO-0030548 A9 | 8/2002 |

OTHER PUBLICATIONS

Alexander, III Impacts of telemation on modern society, *Intl. Centre for Mechanical Sciences, 1st CISM-IFToMM Symposium, on Theory and Practice of Robots and Manipulators*, (Sep. 5-8, 1973) vol. II, pp. 1122-1136.

Iwata, H., "Pen-based haptic virtual environment," *IEEE Institute of Engineering Mechanics*, U. of Tsukuba, Japan, (1993) pp. 287-292.

Mack, et al., "Video-assisted coronary bypass grafting on the beating heart," *Ann. Thorac. Surg.*, (1997) 63:S100-103.

Madhani, A., "Thesis Proposal: Force-Reflecting Teleoperated Endoscopic Surgery." *MIT Department of Mechanical Engineering and Artificial Intelligence Laboratory*, Cambridge, MA, (Nov. 17, 1995) pp. 1-6 w/attachments pp. 1-2.

Rovetta et al., "The first experiment in the world of robotic telesurgery for laparoscopy carried out by means of satellites networks and optical fibres networks on (Jul. 7, 1999)," *IEEE Telerobotics Laboratory*, Italy, Institute of Clinical Surgery, Italy, *Jet Propulsion Laboratory*, Pasadena, USA, pp. 51-56.

Sukthankar et al., "Towards force feedback in laparoscopic surgical tools," *IEEE, Human Interface Laboratory Dept. of Biomedical Engineering*, Ohio, (1994) pp. 1041-1042.

PCT/US01/44771 International Search Report, mailed Apr. 23, 2003, 7 pages; and Written Opinion, mailed Aug. 12, 2003, 6 pages.

Vertut, Jean and Coeffet, Philippe Coiffet; "Robot Technology; vol. 3A Teleoperation and Robotics Evolution and Development"; 1986; Prentice-Hall, Inc; Englewood Cliffs, N.J.

EP10181123.0 Extended European Search Report, mailed Apr. 14, 2011, 9 pages.

Abstract of a presentation "3-D Vision Technology Applied to Advanced Minimally Invasive Surgery Systems," (Session 15/3) given at the 3rd World Congress of Endoscopic Surgery in Bordeaux, Jun. 18-20, 1992, 1 page.

Abstract of a presentation "A Pneumatic Controlled Sewing Device for Endoscopic Application the MIS Sewing Instrument MSI" given at the 3rd World Congress of Endoscopic Surgery in Bordeaux, Jun. 18-20, 1992, 1 page.

Abstract of a presentation given at the 3rd World Congress of Endoscopic Surgery in Bordeaux entitled "Session 15/1", Jun. 18-20, 1992, 1 page.

Abstract of a presentation given at the 3rd World Congress of Endoscopic Surgery in Bordeaux, entitled "Session 15/2", Jun. 18-20, 1992, 1 page total.

Abstract of a presentation given at the 3rd World Congress of Endoscopic Surgery in Bordeaux entitled "Session 15/4", Jun. 18-20, 1992, 1 page.

Abstract of a presentation given at the 3rd World Congress of Endoscopic Surgery in Bordeaux entitled "Session 15/5", Jun. 18-20, 1992, 1 page.

Alexander, Arthur D., "A Survey Study of Teleoperators Robotics and Remote Systems Technology," Remotely Manned Systems Exploration and Operation in Space, California Institute of Technology, 1973, pp. 449-458.

Anderson, Robert J., "Bilateral Control of Teleoperators with Time Delay," IEEE Transactions on Automatic Control, IEEE, 1989, vol. 34, No. 5, pp. 494-501.

Asada Haruhiko et al., "Development of a direct drive arm using high torque brushless motors," Proc. of 1st Int. Symp. On Robotics Research, 1984, pp. 583-599, Chapter 7, MIT Press.

Askew, Scott R. et al., "Ground control testbed for space station freedom robot manipulators," IEEE Virtual Reality Annual International Symposium, 1993, pp. 69-75, IEEE.

B-1 Bomber Simulator, 8 pages [online], [retrieved on Jun. 28, 2013]. Retrieved from the Internet: <URL:http://www.seeingtheusa.com/2012/10/b-1-bomber-simulator.html>.

Baumann, Roger, "Haptic Interface for Virtual Reality Based Laparoscopic Surgery Training Environment," These No. 1734 Ecole Pholytechnique Federale de Lausanne, 1997, 104 Total Pages.

Bejczy, Antal K. et al., "A synchronized computational architecture for generalized bilateral control of robot arms," SPIE Space Station Automation III, 1987, pp. 123-134, vol. 851.

Bejczy, Antal K. et al., "Controlling Remote Manipulators through Kinesthetic Coupling," Computers in Mechanical Engineering, 1983, pp. 48-60, vol. 1-Issue 1.

Ben Gayed, M. et al., "An Advanced Control Micromanipulator for Surgical Application," Systems Science, 1987, pp. 23-34, vol. 13 No. 1-2ol 13 No. 1-2.

Ben Gayed, M. et al., "An Advanced Control Micromanipulator for Surgical Applications," Systems Science, 1987, pp. 123-134, vol. 13.

Besant, Colin et al., Abstract of presentation "Camera Control for Laparoscopic Surgery by Speech recognizing Robot: Constant Attention and Better Use of Personnel," 3rd World Congress of Endoscopic surgery, 1992, p. 271, vol. 3—issue 3.

Bose, Bijo et al., "Tremor compensation for robotics assisted microsurgery," Annual Intl Conf of IEEE Engineering in Medicine and Biology Society, Oct.-Nov. 1992, pp. 1067-1068, vol. 14—Issue 3, IEEE.

Bowersox, Jon C. et al., "Vascular applications of telepresence surgery: Initial feasibility studies in swine," J. Vascular Surgery, Feb. 1996, pp. 281-287, vol. 23—Issue 2.

Butner, Steven E. et al., "A real-time system for tele-surgery," IEEE 21st International Conference on Distributed Computing Systems, 2001, pp. 236-243, IEEE.

Cavusoglu, Murat Cenk et al., "A Laparoscopic Telesurgical Workstation," IEEE Transactions on Robotics and Automation, Aug. 1999, vol. 15, Issue 4, pp. 728-739.

Charles, Steve et al., "Design of a Surgeon Machine Interface for Teleoperated Microsurgery," Proceedings of IEEE Annual Conference on Engineering in Medicine and Biology, 1989, pp. 0883-0884, vol. 11, IEEE.

(56) References Cited

OTHER PUBLICATIONS

Christensen, B. et al., "Model based sensor directed remediation of underground storage tanks," International Conf. on Robotics and Automation, Sacramento, CA, Apr. 1991, pp. 1377-1383, vol. 2. IEEE.
Cohn, Michael C., "Medical Robotics," http://www-bsac.eecs.berkeley.edu/ , 1996, pp. 1-8 and 4.
Colgate, Edward, J., "Power and Impedance Scaling in Bilateral Manipulation," IEEE International Conference on Robotics and Automation, Sacramento, California, Apr. 1991, pp. 2292-2297, vol. 3, IEEE.
Colgate, J. Edward, "Robust Impedance Shaping Telemanipulation,"IEEE Transactions on Robotics and Automotion, 1993, pp. 374-384, vol. 9—No. 4, IEEE.
Computer Motion, Inc., "AESOP: Automated Endoscopic Systems for Optimal Positioning," Press Release, 1994, 2 pages.
Computer Motion, Inc., "Automated Endoscopic System for Optimal Positioning," Enhancing Performance Through Robotics, Date Unknown, 2 pages.
Co-pending U.S. Appl. No. 60/111,710, filed Dec. 8, 1998.
Co-pending U.S. Appl. No. 60/111,711, filed Dec. 8, 1998.
Co-pending U.S. Appl. No. 60/111,713, filed Dec. 8, 1998.
Co-pending U.S. Appl. No. 60/111,714, filed Dec. 8, 1998.
Co-pending U.S. Appl. No. 60/116,891, filed Jan. 22, 1999.
Corcoran, Elizabeth, "Robots for the Operating Room," The New York Times, 2 pages total, Jul. 19, 1992, Section 3 p. 9C.
Das, Had et al., "Kinematic Control and Visual Display of Redundant Teleoperators," IEEE International Conference on Systems, Man, and Cybernetics, 1989, pp. 1072-1077, vol. 3, IEEE.
Dolan, J.M. et al., "A Robot in an Operating Room: A Bull in a China Shop," 1987, pp. 1096-1097, vol. 2.
Elder, Matthew C. et al., "Specifying user interfaces for safety critical medical systems," Second Annual International Symposium on Medical Robotics and Computer Assisted Surgery, Nov. 1995, pp. 148-155.
EP Patent Application No. 00921806.6 Extended European Search Report, mailed on Jul. 9, 2004, 3 pages.
EP Patent Application No. 08017470.9 Extended European Search Report, mailed Oct. 28, 2009, 6 pages.
EP Patent Application No. 09171392 European Search Report dated Feb. 22, 2010, 7 pages total.
EP Patent Application No. 11150512 Partial European Search Report, mailed on Feb. 7, 2012, 9 pages.
EP Patent Application No. 99965017 Supplementary European Search Report mailed on Jun. 12, 2007, 3 pages.
European Search Report for Application No. EP09166502, mailed on Nov. 25, 2009, 10 pages.
European Search Report for Application No. EP12151644, mailed on Jun. 8, 2012, 2 pages.
European Search Report for Application No. EP12151647, mailed on Jun. 7, 2012, 4 pages.
European Search Report for Application No. EP12151648, mailed on Jun. 8, 2012, 3 pages.
Finlay, Patrick A., "Orthosista, An Active Surgical Localiser for Assisting Orthopaedic Fracture Fixation," Proceedings of the Second Annual International Symposium on Medical Robotics and Computer Assisted Surgery; Baltimore, MD; Nov. 4-7, 1995, pp. 203-207.
Fu, K.S. et al., "Robotics: control, sensing, vision, and intelligence," 1987, pp. 12-76 and 201-265, Ch. 2 & 5, McGraw-Hill Book Company.
Funda, Janez et al., "Constrained Cartesian Motion Control for Teleoperated Surgical Robots,". IEEE Transactions on Robotics and Automation, IEEE, Jun. 1996, vol. 12, No. 3, pp. 453-465.
Galloway, Robert L. et al., "A new device for interactive image guided surgery," Proceedings The International Society of Optical Engineering SPIE Medical Imaging V: Image Capture Formatting and Display Kim Y Ed, 1991, pp. 9-18, vol. 1444, SPIE.
Goertz, Ray et al., "ANL mark E4A electric master slave manipulator," Proc 14th Conf. on Remote System Technology, 1996, pp. 115-123.
Graves, Sean et al., "Dynamic Session Management for Telerobotic Control and Simulation," IEEE International Conference on Robotics and Automation, 1994, pp. 1740-1745, vol. 2, IEEE.
Green, Philip S., "A Pneumatic Controlled Sewing Device for Endoscopic Application the MIS Sewing Instrument MSI," Abstract No. 7, 1992.
Green, Philip S. et al., Abstract of a presentation, "Telepresence: Advanced Teleoperator Technology for Minimally Invasive Surgery," 1992 Medicine Meets Virutual Reality (MMVR) symposium in San Diego, Jun. 4-7, 1992, 1 page.
Green, Philip S. et al., Abstract of a presentation "Telepresence: Advanced Teleoperator Technology for Minimally Invasive Surgery, " given at the 3rd World Congress of Endoscopic Surgery in Bordeaux, Jun. 18-20, 1992, 2 pages total, abstract 704.
Green, Philip, S. et al. "Mobile telepresence surgery, " 2nd Annual Intl Symposium on Med. Robotics and Computer Assisted Surgery, Maryland Nov. 1995, pp. 97-103.
Green, Philip S. et al., Statutory Declaration by Dr. Phillip S. Green, the presenter of the video entitled "Telepresence Surgery: The Future of Minimally Invasive Medicine, " European Patent Convention in the Matter of EP-B-653922. 32 pages, Sep. 12, 2000.
Guerrouad, Aicha et al., "SMOS: Stereotaxical Microtelemanipulator for Ocular Surgery," IEEE Engineering in Medicine & Biology 11th annual international conference, Nov. 9-12, 1989, pp. 879-880, vol. 3, IEEE.
Guo, Shuxinng et al., "Micro active guide wire catheter system—characteristic evaluation, electrical model and operability evaluation of micro active catheter," Sixth Internaional IEEE Symposium on Micro Machine and Human Science, 1995, pp. 131-136, IEEE.
Guthart, Gary S. et al., "The IntuitiveT telesurgery system: overview and application," Proceedings of the 2000 IEEE International Conference on Robotics & Automation, 2000, pp. 618-621, vol. 1, IEEE.
Hamilton, E.C. et al., "Comparision of Video Trainer and Virtual Reality Training Systems on acquisition of Laparoscopic Skills," , Surgical endoscopy, 2001, pp. 406-411, vol. 16, Springer Verlang New York Inc.
Heer, Ewald, "Remotely Manned Systems: Exploration and Operation in Space," Proceedings of the First National Conference Pasadena, CA, Sep. 13-15, 1972, pp. 449-458 and 483-492.
Hill, John, W. et al., "Tactile Perception Studies Related to Teleoperator Systems," Final Report, Contract NAS 2-5409, SRI Project 7948, Stanford Research Institute, Menlo Park, California, 1971, 45 pages.
Hill, John W. et al., "Telepresence Technology in Medicine: Principles and Applications," Proceedings of IEEE, 1998, vol. 86—Issue 3, pp. 569-580, IEEE.
Hill, John W., "Telepresence surgery demoonstration system," Robotics and Automation, 1994, pp. 2302-2307, vol. 3, SRI International.
Hogan, Neville, "Controlling Impedance at the Man/Machine Interface," IEEE International Conference on Robotics and Automation, 1989, pp. 1626-1631, vol. 3, IEEE.
Holler, Elmar et al., "An ATM based local communication system for telesurgery," Interactive Tech. and New Paradigm Healthcare, 1995, pp. 137-146.
Hunter, Ian W. et al., "A teleoperated microsurgical robot and associated virtual environment for eye surgery," Presence: Teleoperators and Vitual Environments, 1993, pp. 265-280, vol. 2—No. 4, MIT Press.
Hunter, Ian, W. et al., "Manipulation and dynamic mechanical testing of microscopic objects using a tele-micro-robot system," IEEE Control Systems Magazine, 1990, pp. 3-9, vol. 10—Issue 2, IEEE.
Hurteau et al., "Laparoscopic surgery assisted by a robotic cameraman: Concept and Experimental results," IEEE International Conference on Robotics and Automation, May 8-13, 1994, pp. 2286-2289, vol. 3, IEEE.
Ikuta, Koji et al., "Hyper redundant active endoscope for minimum invasive surgery," pp. 230-237, Proc. IEEE The First International Conference on Medical Robot and Computer Aided Surgery (MRCAS'94), (1994).
Imaida, Takashi et al., "Ground-Space Bilateral Teleoperation of ETS-VII Robot Arm by Direct Bilateral Coupling Under 7-s Time Delay Condition," IEEE Transactions on Robotics and Automation, 2004, pp. 499-511, vol. 20—No. 3, IEEE.

(56) References Cited

OTHER PUBLICATIONS

Inoue, Masao; "Six-Axis bilateral control of an articulated slave manipulator using a Cartesian master manipulator," Advanced robotics, 1990, pp. 139-150, vol. 4—Issue 2, Robotic society of Japan.
International Preliminary Examination Report for Application No. PCT/US01/44771, mailed on Feb. 26, 2004, 5 pages.
International Preliminary Examination Report for Application No. PCT/US03/01348, mailed on Apr. 19, 2004, 4 pages.
International Preliminary Examination Report for Application No. PCT/US1999/27632, mailed on Aug. 24, 2001, 6 pages.
International Preliminary Examination Report for Application No. PCT/US99/27616, mailed on May 16, 2001, 4 pages.
International Search Report for application No. PCT/US03/01348, Mailed on Jun. 5, 2003, 1 page.
International Search Report for application No. PCT/US99/27632, Mailed on Feb. 23, 2001, 2 pages.
Jackson, Bernie G. et al., "Force Feedback and Medical Simulation," Interactive Technology and the New Paradigm for Healthcare, Morgan et al. (Eds), 1995, pp. 147-151, vol. 24, IOS Press and OHMS.
Jau, B. M., "Anthropomorphic Remote Manipulator," NASA Tech Briefs, Apr. 1991, p. 92, NASA's Jet Propulsion Laboratory, Pasadena, California.
Kazerooni, H., "Human Extenders," ASME J. Dynamic Systems, Measurements and Control, 1993, pp. 281-290, vol. 115 No. 2(B).
Kazerooni, H., "Design and analysis of the statically balanced direct-drive robot manipulator, " Robotics and Computer-Integrated Manufacturing, 1989, pp. 287-293, vol. 6, Issue 4.
Kazerooni, H., "Human/Robot Interaction via the Transfer of Power and Information Signals Part 1: Dynamics and Control Analysis," IEEE International Conference on Robotics and Automation, 1989, pp. 1632-1640, IEEE.
Kazerooni, H, "Human/Robot Interaction via the Transfer of Power and Information Signals—Part II," An Experiemental Analysis, Proc. of the 1989 IEEE International Conference on Robotics and Automation, 1989, pp. 1641-1647, vol. 3, IEEE.
Kim, Won S., "Developments of New Force Reflecting Control Schemes and an Application to a Teleoperation Training Simulator," Proceedings of the 1992 IEEE International Conference on Robotics and Automation, 1992, pp. 1412-1419, vol. 2, IEEE.
Kirklin, John W. et al., "Cardiac Surgery," 1993, 4 pages Total, vol. 1 and 2, Second ed John Wiley and Sons Inc N Y (Table of Contents).
Kosuge, Kazuhiro, "Bilateral Feedback Control of Telemanipulators via Computer Network," IEEE International Conference on Intelligent Robots and Systems, 1996, pp. 1380-1385. vol. 3, IEEE.
Krishnan, S.M. et al., Abstract of a presentation "Design Considerations of a New Generation Endoscope Using Robotics and Computer Vision Technology," given at the 3rd World Congress of Endoscopic Surgery in Bordeaux, Jun. 18-20, 1992, 1 page.
Landreneau, Rodney J. et al., "Video Assisted Thoracic Surgery: Basic Technical Concepts and Intercostal Approach Strategies," The Annals of Thoracic Surgery, 1992, pp. 800-807, vol. 54—Issue 4, The Society of Thoracic Surgeons.
Lappalainen J., et al., Direct Connection of Simulator and DCS Enhances Testing and Operator Training, 8 pages, [online], [retrieved on Jul. 2, 2013]. Retrieved from the Internet: <URL:http//www.tappi.org/Downloads/unsorted/Untitled—ENG99495pdf.aspx>.
Lavallee, Stephane, "A New System for Computer Assisted Neurosurgery," IEEE Eng. in Med. & Biol. Soc. 11th Annual International Conference, Jun. 1989, pp. 926-927, vol. 11.
Lazarevic, Zoran, "Feasibility of a Stewart Platform with Fixed Actuators as a Platform for CABG Surgery Device," 1997, 45 pages, Master's Thesis Columbia University Department of Bioengineering.
Liu, Alan et al., "A Survey of Surgical Simulation: Applications, Technology and Education," Presence, 2003, pp. 599-614, MIT Press.
Madhani, Akhil J. et al., "The black falcon: A teleoperated surgical instrument for minimally invasive surgery," IEEE/RSJ Int. Conf. on Intelligent Robots and Systems (IROS) Victoria B.C. Canada ), 1998, pp. 936-944, vol. 2, IEEE.
Mair, Gordon M., Industrial Robotics, Prentice Hall, 1988, pp. 41-43, 49-50, 54, 203-209.
Majima S. et al., "On a Micro Manipulator for Medical Application Stability Consideration of its Bilateral Controller Mechatronics," 1991, pp. 293-309, vol. 1—Issue 3.
Medical Simulation, 7 pages, [online], [retrieved on Jul. 2, 2013]. Retrieved from the Internet: <URL:http://en.wikipedia.org/wiki/Medical_simulation>.
Melzer, Abstract of a presentation "Concept and Experimental Application of a Surgical Robotic System the Steerable MIS Instrument SMI," given at the 3rd World Congress of Endoscopic Surgery in Bordeaux, Jun. 18-20, 1992, 1 page total.
Moravec, Hans, Peter, "Obstacle Avoidance and Navigation in the Real World by a Seeing Robot Rover," PhD thesis, 1980, Chapter 3, pp. 13-18, Stanford University.
Neisius B. et al., "Robotic manipulator for endoscopic handling of surgical effectors and cameras," 1st Intl. Symposium on Medical Robotics and Computer Assisted Surgery, 1994, pp. 169-176, vol. 2.
Nudehi, Shahin S. et al., "A Shared-Control Approach to Haptic Interface Design for Minimally Invasive Telesurgical Training," IEEE Transactions on Control Systems Technology, 2005, pp. 588-592, vol. 13—No. 4, IEEE.
PCT/US00/09201 International Search Report, mailed Aug. 30, 2000, 1 page.
PCT/US99/27610 International Search Report, mailed Apr. 25, 2000, 3 pages.
PCT/US99/27616 International Search Report mailed on May 3, 2000, 1 page.
Preising, B. et al., "A Literature Review: Robots in Medicine," IEEE Engineering in Medicine and Biology, 1991, pp. 13-22, 71, vol. 10—Issue 2, IEEE.
Rasor, Ned S. et al., "Endocorporeal Surgery Using Remote Manipulators," Proceedings of the First National Conference held at California Institute of Technology, 1972, pp. 483-492.
Richardson, I. E. G. et al., "SAVIOUR: Telemedicine in Action," IEE Colloquium on Teleworking and Teleconferencing, 1994, pp. 4/1-4/2, IEEE.
Rosheim, Mark E., Chapter 5: "Pitch-Yaw-Roll Wrists," Robot Wrist Actuators, Wiley & Sons, New York, 1989, pp. 95-206.
Sabatini, A. M. et al., "Force Feedback Based Telemicromanipulation for Robot Surgery on Soft Tissue," IEEE Engineering in Medicine and Biology Society 11th Annual International Conference, 1989, pp. 890-891, vol. 3, IEEE.
Sackier J.M., et al., "Robotically Assisted Laparoscopic Surgery, From Concept to Development," Surgical Endoscopy, Springer-Verlag, 1994, vol. 8 (8), pp. 63-66.
Sastry, Shankar et al., "Millirobotics for remote minamally invasive surgery," Proceedings of the Intl. Workshop on Some Critical Issues in Robotics, Singapore, Oct. 2-3, 1995, pp. 81-98.
Sato, Yoshinobu et al., "The Safety Assessment of Human-Robot Systems (Architectonic principles of hazard-control systems), " JSME International Journal, 1989, pp. 67-74, vol. 32—Issue 1.
Schenker Paul S. et al., "Development of a New High Dexterity Manipulator for Robot Assisted Microsurgery," Proceedings of SPIE, The Intl. Society for Optical Engineering, 1994, pp. 191-198, vol. 2351.
Schenker, Paul S. et al., "Development of a Telemanipulator for Dexterity Enhanced Microsurgery," 2nd Annual International Symposium on Medical Robotics and Computer Assisted Surgery, Nov. 4-7, Baltimore, Maryland, 1995, pp. 81-88.
Seymout, Neal E. et al., "Virtual Reality Training Improves Operating Room Performance," Annals of Surgery, 2002, pp. 458-464, vol. 236—No. 4, Lippincott Williams & Wilkins, Inc.
Shimoga, K.B. et al., "Touch and Force Reflection for Telepresence Surgery," Proceedings of the 16th Annual International Conference of the IEEE Engineering in Medicine and Biology Society, Engineering Advances: New Opportunities for Biomedical Engineers, 1994, pp. 1049-1050, vol. 2, IEEE.
Sinulation, 22 pages, [online] , [Retrieved on Jul. 2, 2013]. Retrieved from the Internet: <URL: http://en.wikipedia.org/wiki/Simulation>.
Smith, Warren E. et al., "Correction of Distortion in Endoscope Images," IEEE Transactions on Medical Imaging, Mar. 1992, pp. 117-122, vol. 11—Issue 1, IEEE.

(56) References Cited

OTHER PUBLICATIONS

Stevens, Jane E., "Cyber Surgery Computers cameras and robots are creating an improved operating system for doctors," Los Angeles Times, Nov. 30, 1995, p. 2.
Supplementary European Search Report for Application No. EP03707420, mailed on Sep. 13, 2010, 2 pages.
Supplementary European Search Report for Application No. EP99960536, mailed on Jun. 12, 2007, 3 pages.
Supplementary European Search Report for Application No. EP99961747, mailed on Jul. 18, 2007, 3 pages.
Supplementary Partial European Search Report for Application No. EP01987142, mailed on Jul. 28, 2009, 6 pages.
Taubes, Gary et al., "Surgery in Cyberspace," Discover magazine, Dec. 1994, vol. 15, issue 12, pp. 85-92.
Taylor, Russell H. et al., "A Telerobotic Assistant for Laparoscopic Surgery," IEEE Engineering in Medicine and Biology, May/Jun. 1995, pp. 279-288, vol. 14, Issue 3, IEEE.
Taylor, Russell H., et al., "Chapter 46: A Telerobotic Assistant for Laparoscopic Surgery," in Computer-Integrated Surgery, R. H. Taylor, et al., Editors, 1996, MIT Press. pp. 581-592.
Taylor, Russell H. et al., "Computer Integrated Surgery: Technology and Clinical Applications," 1996, pp. vii-xii, MIT Press Cambridge MA.
Taylor, Russell H. et al., "Computer-Integrated Surgery," 1995, 8 Pages, MIT Press.
Taylor, Russell H. et al., "Research Report: A Telerobotic Assistant for Laparoscopic Surgery," Accepted to IEEE EIMBS Magazine, Special Issue on "Robotics in Surgery," Dec. 1994, 24 pages.
Taylor, Russell H. et al., "Taming the Bull: Safety in a Precise Surgical Robot," Fifth International Conference on Advanced Robotics (91 ICAR), Jun. 19-22, 1991, vol. 1, pp. 865-870, IEEE.
Tejima, Noriyuki et al., "A New Microsurgical Robot System for Corneal Transplantation," Precision Machinery, 1988, pp. 1-9, vol. 2, Gordon and Breach Science Publishers Inc.
Tendick Frank, et al., "Analysis of the Surgeon's Grasp for Telerobotic Surgical Manipulation,"IEEE 11th Annual Int Conf on Engineering in Medicine and Biology, Jun. 1989, pp. 914-915, IEEE.
Tendick, Frank et al., "Comparison of Iaproscopic imaging systems and conditions using a knot tying task," Second Annual International Symposium on Medical Robotics and Computer Assisted Surgery, Nov. 4-7, 1995, 9 pages.
Thring, M.W., Robots and Telechirs: Manipulators with Memory; Remote Manipulators; Machine Limbs for the Handicapped, 1983, pp. 9-11, 108-131, 194-195, 235-279; Ellis Horwood Limited, Chapter 5,7,8,9.
Transcript of a video presented by SRI at the 3rd World Congress of Endoscopic Surgery in Bordeaux, France on Jun. 18-20, 1992; in Washington D.C. on Apr. 9, 1992; and in San Diego, CA on Jun. 4-7, 1992; entitled "Telepresence Surgery: The Future of Minimally Invasive Medicine," 3 pages.
Trevelyan, James P. et al., "Motion Control for a Sheep Shearing Robot," IEEE Robotics Research Conference, the 1st International Symposium, Carroll, NH, USA., 1983, pp. 175-190, in Robotics Research, MIT Press.
Trinder J.C. et al., "A Close Range Digital Photogrammetry System,"1990, pp. 440-447, vol. 1395, SPIE.
Tsai, Roger Y., "A Versatile Camera Calibration Technique for High Accuracy 3D Machine Vision Metrology Using," IEEE Journal of Robotics and Automation, 1987, pp. 323-344, vol. RA-3—Issue 4, IEEE.
U.S. Appl. No. 09/399,457, filed Sep. 17, 1999 (now abandoned), Ramans, Andris D.
Vibet, C., "Properties of Master Slave Robots," Motor-con, 1987, pp. 309-316.
Wapler, M., "Medical manipulators—A Realistic Concept" , Minimally Invasive Therapy, 1995, pp. 261-266, vol. 4, Blackwell Science Ltd.
Wolf, Stanley et al., Student Reference Manual for Electronic Instrumentation Laboratories, 1990, pp. 498 and 499, Prentice Hall New Jersey.
Yan, Joseph, et al., "Design and Control of a Motion Scaling System for Microsurgery Experiments," Proc of First Intl Symp on Medical Robotics and Computer Assisted Surgery, 1994, pp. 211-216.
Yan, Joseph et al., "Teleoperation Controller Design Using H Optimization with Application to Motion Scaling," IEEE Transactions on Control Systems Technology, 1996, pp. 244-258, vol. 4—No. 3, IEEE.
Yokokohji, Yasuyoshi and Tsuneo Yoshikawa, "Bilateral Control of Master-Slave Manipulators fro Ideal Kinesthetic Coupling Formulation and Experiment," IEEE Transactions on Robotics and Automation, IEEE, 1994, vol. 10, No. 5, pp. 605-620.
Extended European Search Report for Application No. EP11188641, mailed on May 20, 2014, 6 pages.
Extended European Search Report for Application No. EP11188649, mailed on Jun. 4, 2014, 6 pages.

* cited by examiner

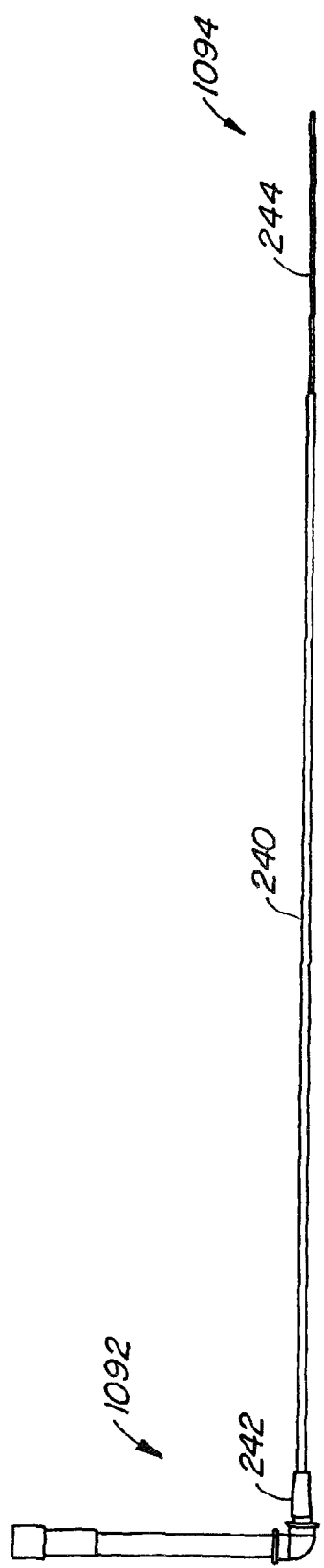
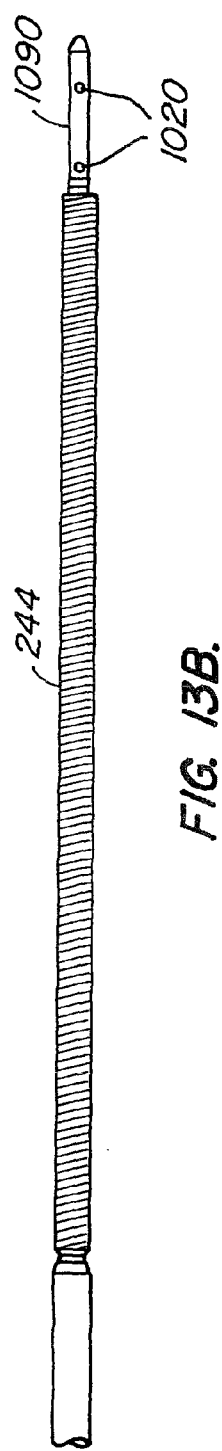
FIG. 13A.
FIG. 13B.

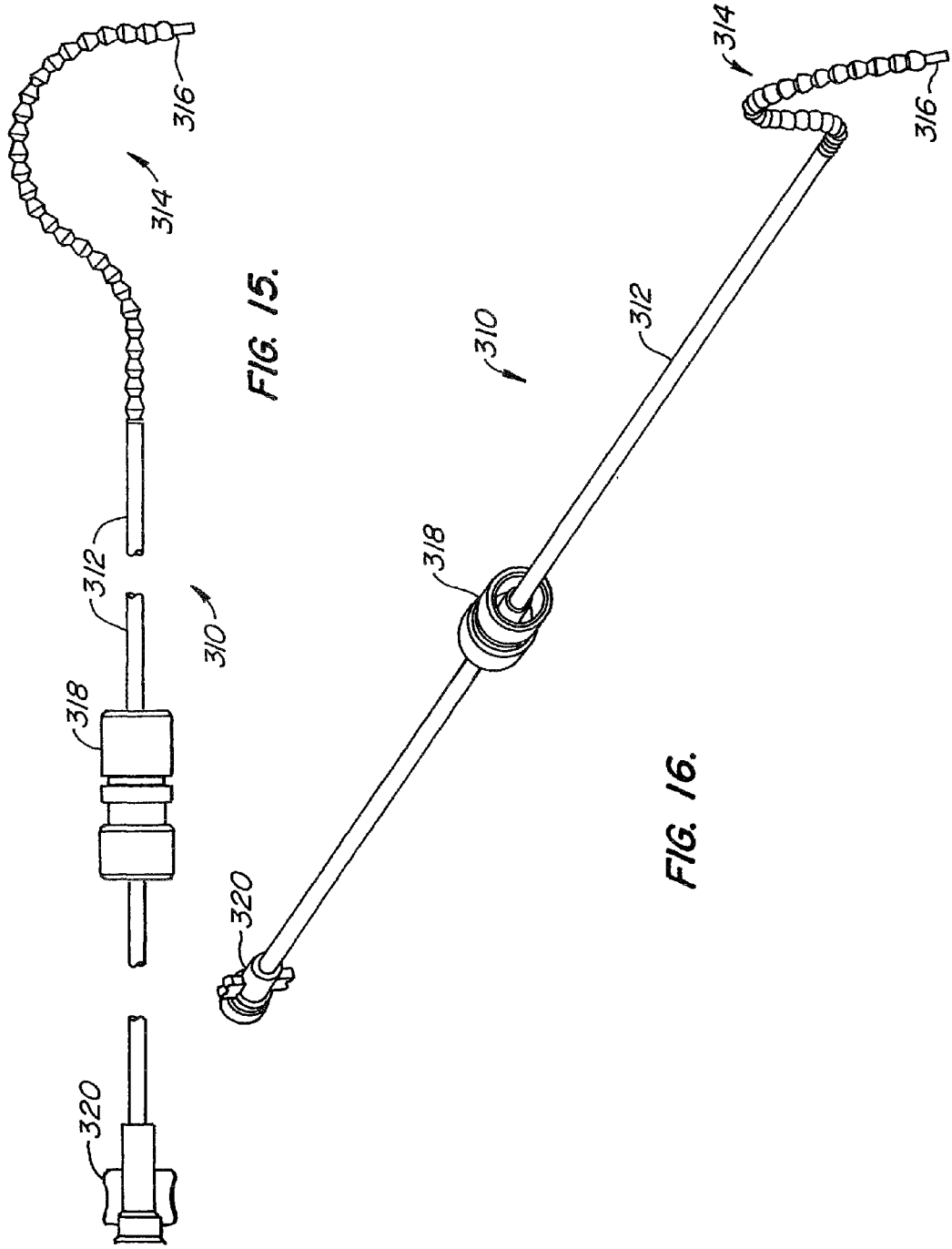

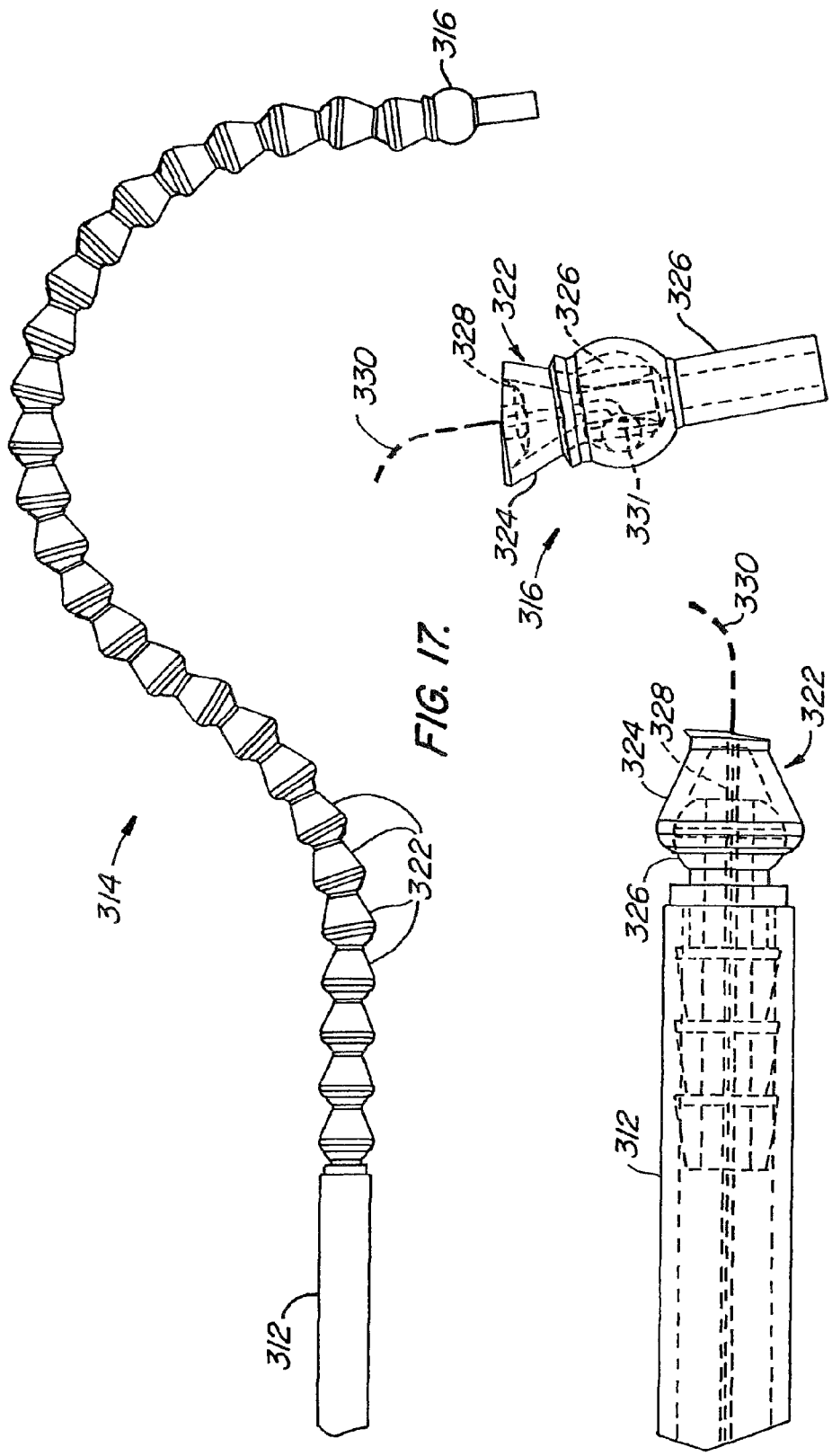

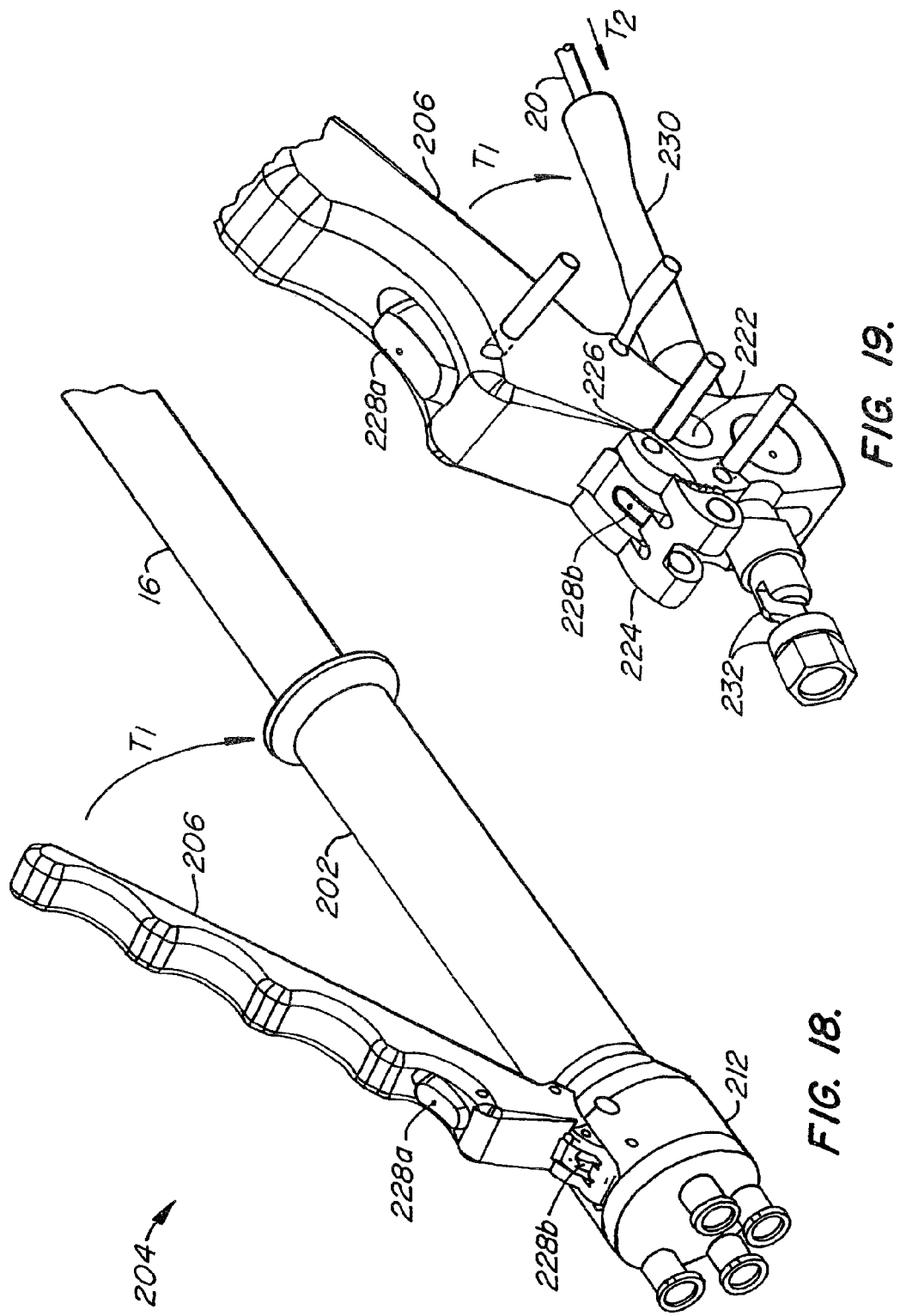

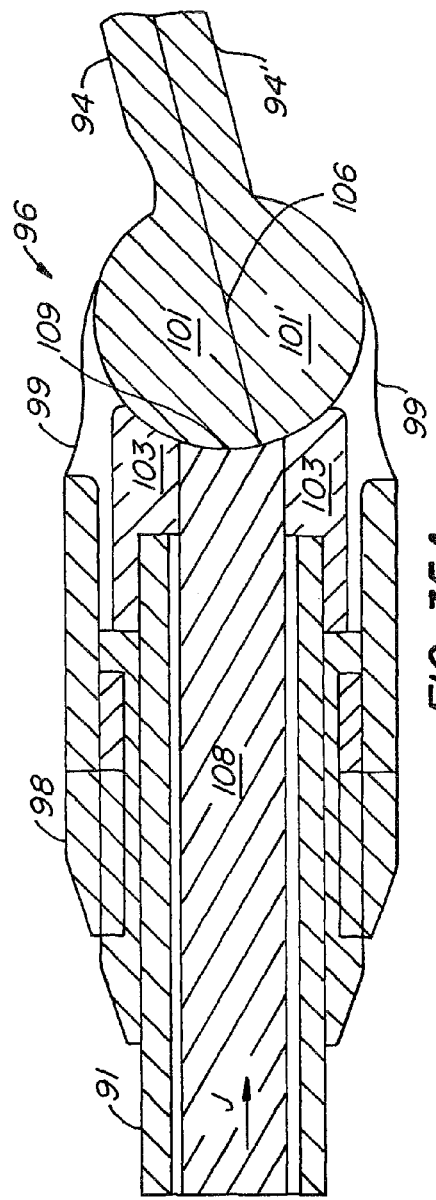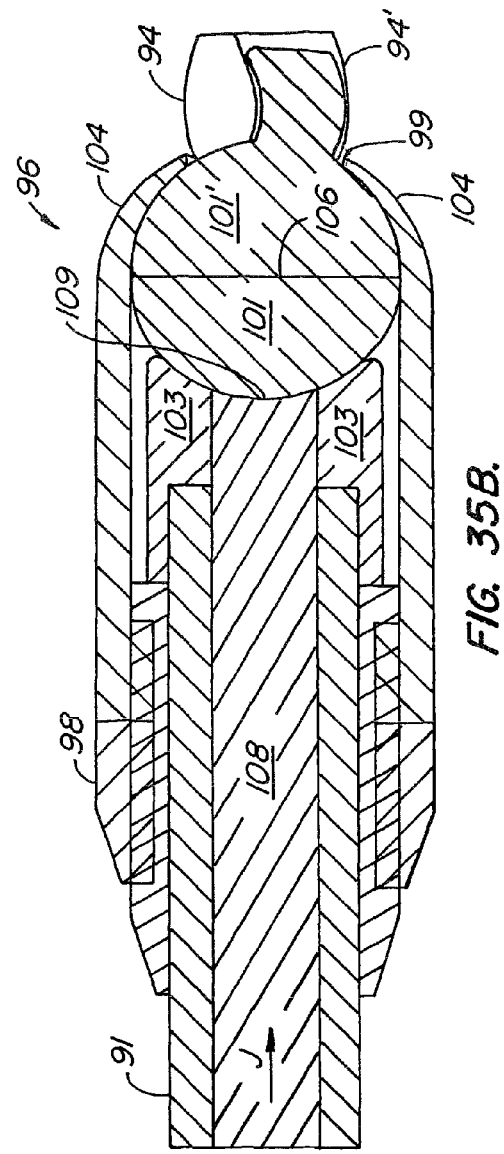

ENDOSCOPIC BEATING-HEART STABILIZER AND VESSEL OCCLUSION FASTENER

CROSS-REFERENCES TO RELATED APPLICATIONS

The present application is a divisional of U.S. patent application Ser. No. 09/998,004, now U.S. Pat. No. 7,250,028, which claims the benefit of priority from the following U.S. patent applications:

No. 60/290,556, filed May 10, 2001, for "Endoscopic Beating-Heart Stabilizer Including Adjustable Irrigator and Vessel Occlusion Fastener";

No. 60/285,641, filed Apr. 19, 2001, for "Endoscopic Beating-Heart Stabilizer";

No. 60/253,484, filed Nov. 28, 2000, for "Endoscopic Beating-Heart Stabilizer".

And which is a continuation-in-part and claims the benefit of priority from Ser. No. 09/436,524, filed Nov. 9, 1999, for "Stabilizer for Robotic Beating-Heart Surgery", now issued as U.S. Pat. No. 6,398,726.

The full disclosures of each of the above referenced patent applications are incorporated herein by reference

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

This invention generally relates to surgical tools, methods, and systems for stabilizing, retracting, and/or inhibiting physiological movement of tissues. In a particular embodiment, the invention provides an endoscopic and optionally robotic surgical stabilizer for use during endoscopic and robotic surgical treatments on a beating heart.

Coronary artery disease remains a leading cause of morbidity and mortality, and particularly in industrialized societies. A number of approaches have been developed for treating coronary artery disease. While lifestyle changes, endovascular approaches (such as balloon angioplasty, atherectomy, and the like) and/or pharmaceutical treatments are often effective, in many cases it is necessary to resort to surgical procedures such as coronary artery bypass grafting to effectively treat coronary artery disease.

Coronary artery bypass graft (CABG) procedures are commonly performed using open-heart techniques. Conventional CABG procedures are described in U.S. Pat. No. 5,452,733 which is fully incorporated herein by reference. These open procedures generally involve dividing the patient's sternum and spreading the chest to provide access to the heart. The patient is placed on a cardiopulmonary bypass (CPB) machine, which oxygenates the patient's blood and pumps it through the patient's circulatory system during the surgical procedure. After the patient is on CPB, drugs (cardioplegia) are administered to temporarily stop the patient's heart to allow the grafting procedure to be performed. Conventional CABG procedures often involve bypassing a narrowed coronary artery by one of two methods. First, existing arteries can be dissected at one end from their natural attachments and transected to a location downstream of the narrowed portion of the coronary artery. The connection site of the graft and the artery is termed an anastomosis. Thus, arterial blood flowing through the existing artery bypasses the narrowing and outputs into the coronary artery which was previously restricted of flow. Second, artificial arterial shunts may be prepared by attaching a natural or synthetic blood vessel, typically a length obtained from a leg vein, at one end to the proximal ascending aorta and at the other end to the target location on a coronary artery downstream of the narrowing. The use of transected arteries is generally preferable since they tend to remain patent for long periods and require only one anastomosis.

When existing arteries are used to bypass a narrowing, the left or right internal mammary artery is often utilized. The left internal mammary artery is suitable as an arterial source for target locations on the left anterior descending coronary artery, the diagonal coronary artery, the circumflex artery/obtuse marginal artery, and the ramus intermedius coronary artery. The right internal mammary artery is available for connection to all of the same target locations, as well as the right coronary artery and the posterior descending artery. It will also be possible to use the gastroepiploic artery in the abdomen. When existing arteries are not available, veins or arteries may be harvested from other locations in a patient's body or synthetic grafts may be used. The grafts thus located will be attached at one end to the proximal ascending aorta (to provide the arterial blood supply) and at the other end to the target location on the coronary artery.

One drawback of conventional CABG procedures is the use of CPB. The use of CPB has been associated with an increased rate of stroke and neurological deficit. Consequently, techniques and devices have been proposed for performing open-heart surgery on a heart while the heart is beating. This eliminates the need for CPB. However, the grafting and anastomosis procedure is often more challenging on a beating heart than on a heart that has been stopped by cardioplegia. To reduce movement of the heart in the grafting area, a tool called a stabilizer is often used to engage the heart and stabilize the area of interest.

While elimination of CPB may improve the outcomes of many patients, the use of open-heart surgery to perform CABG is still highly traumatic to the patient. Thus, minimally invasive medical techniques for performing cardiac surgeries have recently been proposed. Here, the chest cavity is not opened; rather, the heart is accessed through ports or small incisions in the chest through which instruments are inserted. Arteries may be manipulated within the body to provide arterial blood supply to restricted coronary arteries. For example, access to the gastroepiploic artery can be obtained laparoscopically with the artery being brought into the thorax from the abdominal cavity via a window through the diaphragm. Likewise, grafts may be passed into the thorax through either an access trocar sheath or through the aorta (by punching a hole therethrough). These minimally invasive techniques are generally aimed at reducing the amount of extraneous tissue which is damaged during diagnostic or surgical procedures. This can effectively reduce the patient's recovery time, discomfort, and other deleterious side effects of cardiac surgery.

Unfortunately, both the proposed techniques for minimally invasive cardiac surgery and the proposed techniques for beating-heart cardiac surgery significantly increase the difficulty of these already complex surgical procedures. Formation of the anastomosis (the connection between the arterial source and the occluded artery) is quite challenging in a standard coronary artery bypass grafting procedure when the heart tissues are immobile and exposed for direct manipulation. Even skilled surgeons may find it awkward and/or time consuming to instead perform such procedure in a minimally invasive manner or while the heart is beating.

In robotically assisted surgery, the surgeon typically operates one or more master controllers to remotely control the motion of surgical instruments at the surgical site. The controller may be separated from the patient by a significant distance (for example, across the operating room, in a different room, or in a completely different building than the patient). Alternatively, the surgeon's work station with the controllers may be positioned quite near the patient in the operating room. Regardless, the controller will typically include one or more hand input devices, such as a joystick, exo-skeletal gloves, or the like. The hand input devices of the surgeon's workstation are generally coupled to the surgical instrument by a servomechanism. More specifically, servomotors move a manipulator, or "slave" supporting the surgical instrument based on the surgeon's manipulation of the hand input devices.

During a robotic surgical operation, a surgeon using a robotic surgical system may employ, via the manipulator, a variety of surgical instruments, such as tissue graspers, needle drivers, electrosurgical cautery probes, and the like. Each of these structures perform functions for the surgeon, for example, holding or driving a needle, grasping a blood vessel, dissecting, cauterizing, and/or coagulating tissue, and the like. The surgeon and/or an assistant will mount robotic surgical instruments having suitable end effectors to the manipulator, and will often pass the end effectors through cannula sleeves to an internal surgical site, so as to treat the targeted tissues while minimizing injury to the adjacent tissue structures.

In light of the above it would be desirable to provide medical devices, systems, and methods which would facilitate robotically performed endoscopic surgery on tissues undergoing physiological movement. It would be particularly desirable if these devices, systems and methods facilitated coronary artery bypass grafting on a beating heart under closed-chest conditions. It would further be beneficial to provide means for occluding the vessel or coronary artery during the procedure which are independent of the instrumentation so that the vessel may remain occluded while the instrumentation is repositioned. At least some of these objectives will be met by the present invention.

SUMMARY OF THE INVENTION

The present invention provides devices, systems and methods related to endoscopic surgery, particularly related to robotic surgical operations. In particular, the present invention provides a tissue stabilizer for endoscopically stabilizing a target tissue within a patient's body. A primary example would be for stabilizing a beating heart during a closed-chest coronary artery bypass grafting procedure. The stabilizer of the present invention is designed to be inserted through an endoscopic cannula yet provide sufficient surface area to contact the heart and effectively stabilize the target tissue area. In addition, the stabilizer is designed to straddle a blood vessel, such as a coronary artery, which is targeted for the bypass procedure. Typically, an anastomosis is created at the targeted site straddled by the stabilizer. Further, the present invention includes vessel occlusion fasteners to occlude the target blood vessel prior to the anastomosis procedure. This provides a bloodless field when performing the anastomosis procedure.

The stabilizer will typically be coupled to and supported by a drive system or a mounting system to position the stabilizer from outside the patient. The stabilizer is preferably inserted through a cannula or trocar sleeve emplaced in an incision in the patient's body. In some embodiments of the invention, the stabilizer and mounting system may be coupled to the actuators of a servomechanism of a robotic surgical system.

Alternatively, in other embodiments of the invention, the stabilizer may be endoscopic and non-robotic, e.g., may coupled to a positionable mounting apparatus fixed to the operating table or an adjacent base. When the stabilizer is non-robotic, the stabilizer may be manually positioned by an operator outside of the body and/or the stabilizer may be positioned by robotic surgical instruments from within the body. The robotic surgical instruments include a plurality of manipulators with actuators for moving surgical end effectors in response to inputs by a system operator into an input device. The end effectors of the surgical instruments may be used to grasp portions of the stabilizer and adjust or reposition them.

In a first aspect of the present invention, the stabilizer comprises an elongate shaft sized to allow insertion through an endoscopic cannula and a manipulable foot connected with the shaft. The foot is used to engage a target tissue, such as a portion of a beating heart, for stabilization. The stabilizer can inhibit (i.e., substantially reduce) physiological motion of the stabilized region without having to stop the heart. While the stabilized region will not necessarily be absolutely still, motion of the target tissues can be inhibited sufficiently to treat the target tissues, particularly with robotic surgical tools which move in response to inputs of a robotic system operator.

In some embodiments, the manipulable foot comprises a first toe portion rotatably joined with a second toe portion. The first toe portion and second toe portion are rotatable to a first arrangement wherein the foot is insertable through an endoscopic cannula. Such rotation will be described in detail below. Mounted on each toe portion is a stabilizing surface or tissue engaging member. Typically, suction tubes are inserted through suction lumens in the shaft and are connected with each tissue engaging member. Each tissue engaging member comprises as least one suction port through which the suction is provided. Typically, the suction ports are disposed on the underside of the tissue engaging members so that suction is applied when the tissue engaging member is applied to the target tissue. Such suction secures the member to the tissue surface and stabilizes the tissue.

In some embodiments, the toe portions are joined in a toe assembly which allows the toe portions and associated tissue engaging members to rotate, thus reducing the dimensions of the foot to allow the foot to be inserted through a cannula. In some instances, the toe assembly comprises a top ball shell, a first toe portion, a torsion spring, a second toe portion, a bottom ball shell and a rivet which is insertable through these components of the assembly to hold them in place. In these embodiments, each toe portion includes a ring mount. The components of the assembly are assembled so that the ring mount of the first toe portion fits within the top ball shell, the torsion spring fits within a ring notch in each ring mount of the first and second toe portions, and the ring mount of the second toe portion fits within the bottom ball shell. Together, the assembly provides a spring-loaded, collapsible pair of toe portions which are joined at one end to form a spherical split ball shell.

In a second aspect of the present invention, the stabilizer comprises an adjustable ankle disposed between the foot and the shaft. By adjusting the ankle, the foot is moveable in six degrees of freedom relative to the shaft. In some embodiments, the ankle includes an adjustable neck. In some cases, the adjustable neck comprises a series of interlocking elements and intermediate socket rings. Typically, the elements are comprised of balls or ball portions. Each ball is independently rotatable against an adjacent ring to allow the neck to be adjusted. In further embodiments, the ankle also includes an outer housing. A spherical split ball shell, as described above, is mountable within the housing so that the spherical split ball shell is rotatable within the housing. This allows the position of the foot to be adjusted in relation to the shaft.

In a third aspect of the present invention, the stabilizer comprises a tension cable passing through the shaft wherein applying tension to the cable locks the ankle in position. Such locking may be achieved with the use of cable anchor such as a locking ball which is attached to the distal end of the tension cable and is disposed within an inner housing. Both the locking ball and inner housing are disposed within the outer housing. Applying tension to the cable moves the locking ball toward the shaft. This in turn locks the ankle and the foot in place. When the ankle includes an adjustable neck comprising a series of interlocking balls and intermediate rings, the neck may be fixed by applying tension to the cable so that the cable wedges the balls and socket rings together and holds them in place by friction. Thus, the ankle is locked in position. Movement of the locking ball toward the shaft also moves the outer housing toward the shaft. When a spherical split ball shell is disposed within the outer housing, as described above, movement of the outer housing holds the spherical split ball shell in place and restricts its rotation. Thus, the foot is locked in place.

In a fourth aspect of the present invention, the stabilizer comprises at least one suction tube connectable with at least one suction port on the stabilizer foot. Generally, the suction tubes are insertable through suction lumens in the shaft so as to extend distally through the shaft face. In some embodiments, the suction tubes have an elongated shape with a stopper connector portion at its proximal end and a flexible portion at its distal end. The suction tube includes a suction tip disposed at the distal end having one or more suction holes. The suction tip is insertable into a suction tube receptacle in the tissue engaging member so that the suction holes communicate with the suction ports. Suction is provided through the suction ports so that suction holds the stabilizer in firm contact with the target tissue.

In a fifth aspect of the present invention, the stabilizer comprises an irrigator. In most embodiments, the irrigator is insertable through an irrigation lumen in the shaft so that it protrudes outwardly from the shaft face. Fluids may be delivered to the target tissue through the irrigator as needed. The fluids may include liquids (e.g., saline solution, and the like) or gases (e.g., insufflation gas, carbon dioxide, and the like). The fluids may be used for a number of surgical purposes, such as to remove blood from anastomotic site (e.g., by drip irrigating, washing or blowing) and the like. The fluids may also be used to remove blood or other substances from surgical devices, such as cleaning an endoscope objective in vivo, and the like. In some embodiments, the irrigator comprises an elongate conduit and a flexibly adjustable dispenser. The dispenser terminates in a nozzle or spout portion. The dispenser may be adjusted so that the spout portion is directed at the target tissue so that fluid is delivered at the desired location. Alternatively, a vacuum source may be applied to the irrigator mechanism to remove fluids from the body, the spout portion being placed at the location of collected fluids to act as an intake.

In a sixth aspect of the present invention, the stabilizer comprises a handle. As previously mentioned, once the stabilizer has been positioned against the target tissue, the ankle and toe portions may be locked in place to prevent movement of the toes and to maintain proper orientation of the stabilizer. Such locking may be achieved by applying tension to a tension cable. Such tension is applied to the cable with the use of the handle on the stabilizer. In some embodiments, the handle is pivoted to a body at a pivot pin and has an inboard portion which is attached to the cable. When the handle is rotate downward, tension applied from the pivot pin to the inboard portion causes the cable to be stressed and retracted upward. Ratchet pawls then lock the handle in place preventing the handle from pivoting upwards. The cable is released by pressing a release button located on the handle so as to disengage the pawls.

In an additional aspect of the present invention, vessel occlusion devices are provided to isolate a blood vessel from blood flow. To isolate a blood vessel, such as a coronary artery, the vessel is cinched upstream and downstream of the desired location for anastomosis. Thus, when the anastomosis is made, blood will not flow out into the workspace. The vessel occlusion devices of the present invention each include a flexible member attached to a clip. Each flexible member is passed under and around the vessel using instruments inserted within the chest cavity. Each flexible member is then tightened and held by a fastening clip. In some embodiments, the fastening clip comprises a generally elongate plate-like body which has at least one, typically two, holes or bores which intersects radial slots. One end of the flexible member is held in one radial slot, for example, by a locking pin. The free end of the flexible member then wraps around the vessel and is inserted through the second bore to form a loop. After tightening the flexible member to create desired constriction of the vessel, the flexible member is pulled into the adjacent radial slot, holding the flexible member in place.

The flexible members may be attachable with portions of the stabilizer. In particular, the flexible member can be attached to an anchor or cleat on the first and section toe portions so that movement of the first toe portion away from the second toe portion tensions the flexible member. Alternatively, the toe portions can be positioned against the target tissue and the free ends of the flexible member attached to the positioned toe portions to hold the flexible member in place. Thus, the vessel will remain cinched until the flexible members are removed from the toe portions. However, in preferred embodiments, as described above, the flexible members are held in place by the vessel occlusion devices themselves. In this way, the stabilizer may be adjusted and repositioned without affecting the position of the flexible members.

In a method aspect, the invention provides a method for stabilizing a target tissue within a patient's body. In one embodiment, the method includes inserting a tissue stabilizer of the present invention through an endoscopic cannula and positioning the manipulable foot of the stabilizer against the target tissue to stabilize the tissue. When the stabilizer includes toe portions having suction ports, such methods include applying suction to the target tissue through the suction port to stabilize the tissue. When the stabilizer includes any of the above described features, methods of the present invention include positioning, manipulation, adjustment and/or use of any of these features.

In another method aspect, the invention comprises positioning one or more vessel occlusion devices to restrict blood flow through a blood vessel. Other objects and advantages of the present invention will become apparent from the detailed description to follow, together with the accompanying drawings.

BRIEF DESCRIPTION OF THE DRAWINGS

FIGS. 13A-13B illustrate an embodiment of a suction tube.

FIGS. 15, 16, 17, 17A-17B illustrate an embodiment of an irrigator of the present invention.

FIG. 18 illustrates an embodiment of the a handle of the present invention.

FIG. 19 illustrates the mechanisms within the handle which connect the handle with the cable to hold the ankle in position.

FIGS. 35A and 35B are longitudinal cross-sectional views of the split ball ankle portion of the stabilizer showing the split ball mechanism in the deployed and furled positions respectively.

DETAILED DESCRIPTION OF THE INVENTION

The following detailed description illustrates the invention by way of example, not by way of limitation of the principles of the invention. This description will clearly enable one skilled in the art to make and use the invention, and describes several embodiments, adaptations, variations, alternatives and uses of the invention, including what is presently believed to be the best mode of carrying out the invention.

In this regard, the invention is illustrated in the several figures, and is of sufficient complexity that the many parts, interrelationships, and sub-combinations are most clearly or meaningfully illustrated in a series of separate patent-type drawings. Accordingly, several of the drawings show in schematic, or omit, parts that are not essential in that drawing to a description of a particular feature, aspect or principle of the invention being disclosed. Thus, the best mode embodiment of one feature may be shown in one drawing, and the best mode of another feature will be called out in another drawing.

All publications and patent applications cited in this specification are herein incorporated by reference as if each individual publication or patent application were specifically and individually indicated to be incorporated by reference.

Overview of Robotic Surgery Devices and Methods

Figure 1:
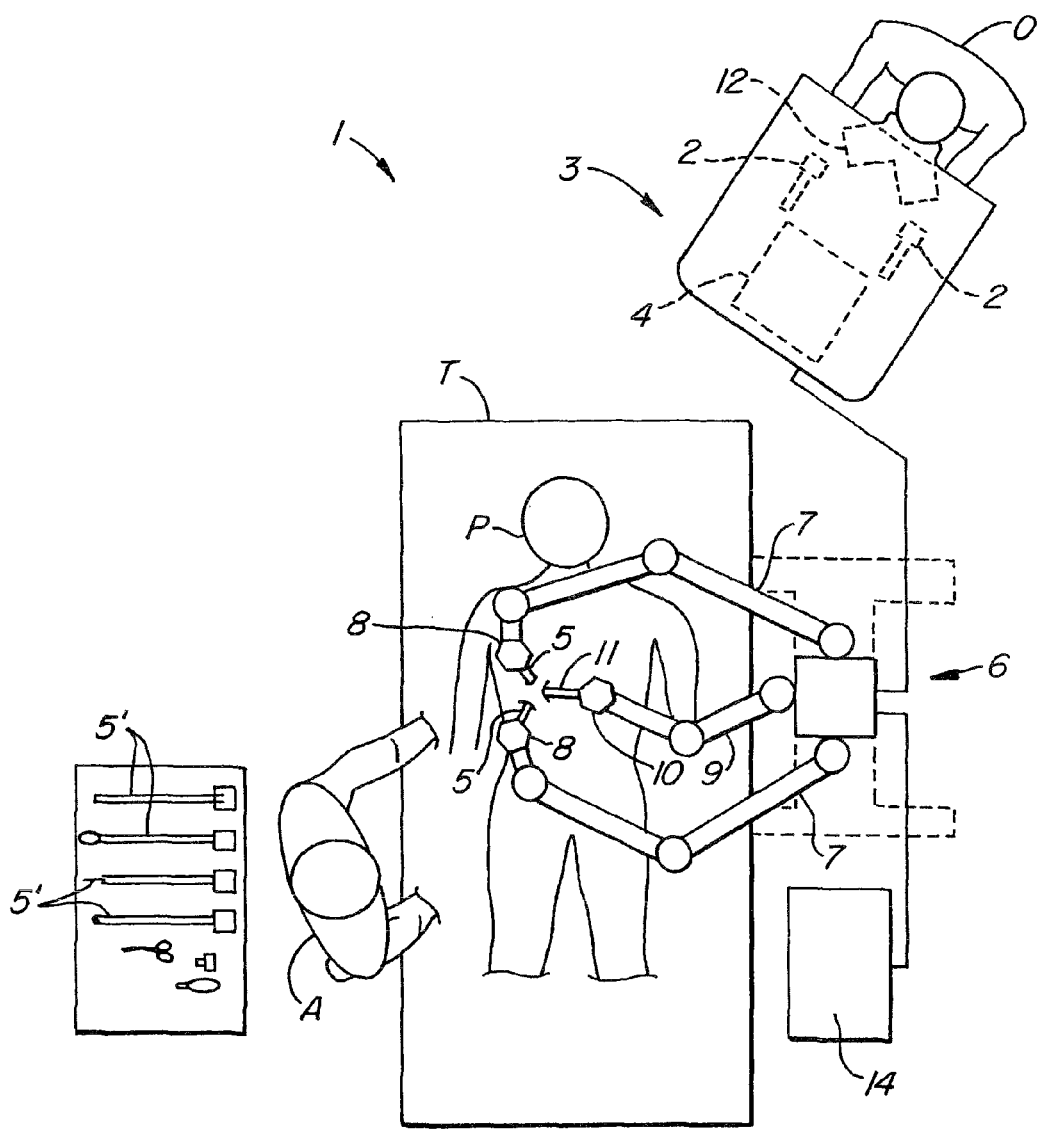
FIG. 1 is a schematic plane view of a portion of an operating room showing a typical robotic surgical system performing a minimally invasive robotic surgical procedure.

FIG. 1 is a schematic plane view of a portion of an operating room showing by way of background an exemplary robotic surgical system 1 performing a minimally invasive robotic surgical procedure. Such a robotic surgical system is described in Application No. PCT/US99/17,522, filed Aug. 3, 1999, entitled Manipulator Positioning Linkage For Robotic Surgery, published on Feb. 17, 2000 as WO00/07,503, the full disclosure of which is incorporated by reference.

Additional examples of robotic surgical systems, related apparatus and subsystems and surgical methods for use with the present invention are described in co-pending U.S. patent application Ser. No. 09/433,120, filed on Nov. 3, 1999, entitled "Cooperative Minimally Invasive Telesurgical System", which was the basis for International Application No. PCT/US99/27,61, filed Nov. 18, 1999 and published as WO 00/30548 on Jun. 2, 2000; and in co-pending U.S. patent application Ser. No. 09/373,678 entitled "Camera Reference Control in a Minimally Invasive Surgical Apparatus," filed Aug. 13, 1999. The full disclosure of each application is incorporated herein by reference.

Examples of both robotic and endoscopic beating heart stabilizers are described in co-pending U.S. patent application Ser. No. 09/436,524, filed Nov. 9, 1999, entitled "Stabilizer For Robotic Beating-Heart Surgery," which was the basis for International Application No. PCT/US99/27,610, filed Nov. 18, 1999 and published as WO 00/30551 on Jun. 2, 2000, both of which are assigned to the assignee of the present application. The full disclosures of these applications are incorporated by reference as if fully set forth herein.

An operator O (generally a surgeon) performs a minimally invasive surgical procedure on patient P lying on operating table T, the operator O manipulating one or more input devices or masters 2 at a surgeon's console 3. In response to the surgeon's inputs, a computer processor 4 of console 3 directs movement of endoscopic surgical instruments or tools 5, effecting servo-mechanical movement of the instruments via a robotic patient-side system 6 (a cart-mounted system in this example).

Typically, patient side system or cart 6 includes at least three robotic manipulator arms. Two arms or linkages 7 (mounted at the sides of cart 6 in this example) support and position servo-manipulators 8 which drive surgical tools 5; and one arm or linkage 9 (mounted at the center of cart 6 in this example) supports and positions servo-manipulator 10 which controls the motion of an endoscope/camera probe 11, which captures an image (preferably stereoscopic) of the internal surgical site.

The image of the internal surgical site shown to operator O by a stereoscopic display viewer 12 in surgeon's console 3, and is simultaneously shown to assistant A by an assistant's display 14. Assistant A assists in pre-positioning the manipulator 8 and 10 relative to patient P, in swapping tools 5 in one or more of surgical manipulator 8 (and/or 10) for alternative surgical tools or instruments 5' in operating related non-robotic medical instruments and equipment, and the like.

In general terms, the arms or linkages 7, 9 comprise a positioning linkage or set-up arm portion of patient-side system 6, typically remaining in a fixed configuration while tissue is manipulated, and the manipulators 8, 10 comprise a driven portion which is actively articulated under the direction of surgeon's console 3. The actively driven portion is herein generally referred to as a "manipulator", and the fixable portion of the positioning linkage of patient-side system linkage is referred to herein as a "set-up arm", it being noted that such setup arms may optionally have powered and computer controlled joints as described herein.

For convenience in terminology, a manipulator such as 8 actuating tissue affecting surgical tools is generally referred to herein as a PSM (patient-side manipulator), and a manipulator such as 10 controlling an image capture or data acquisition device, such as endoscope 11, is generally referred to herein as a ECM (endoscope-camera manipulator), it being noted that such telesurgical robotic manipulators may optionally actuate, maneuver and control a wide variety of instruments, tools and devices useful in surgery.

Overview of Stabilizer of Present Invention

Figure 2:
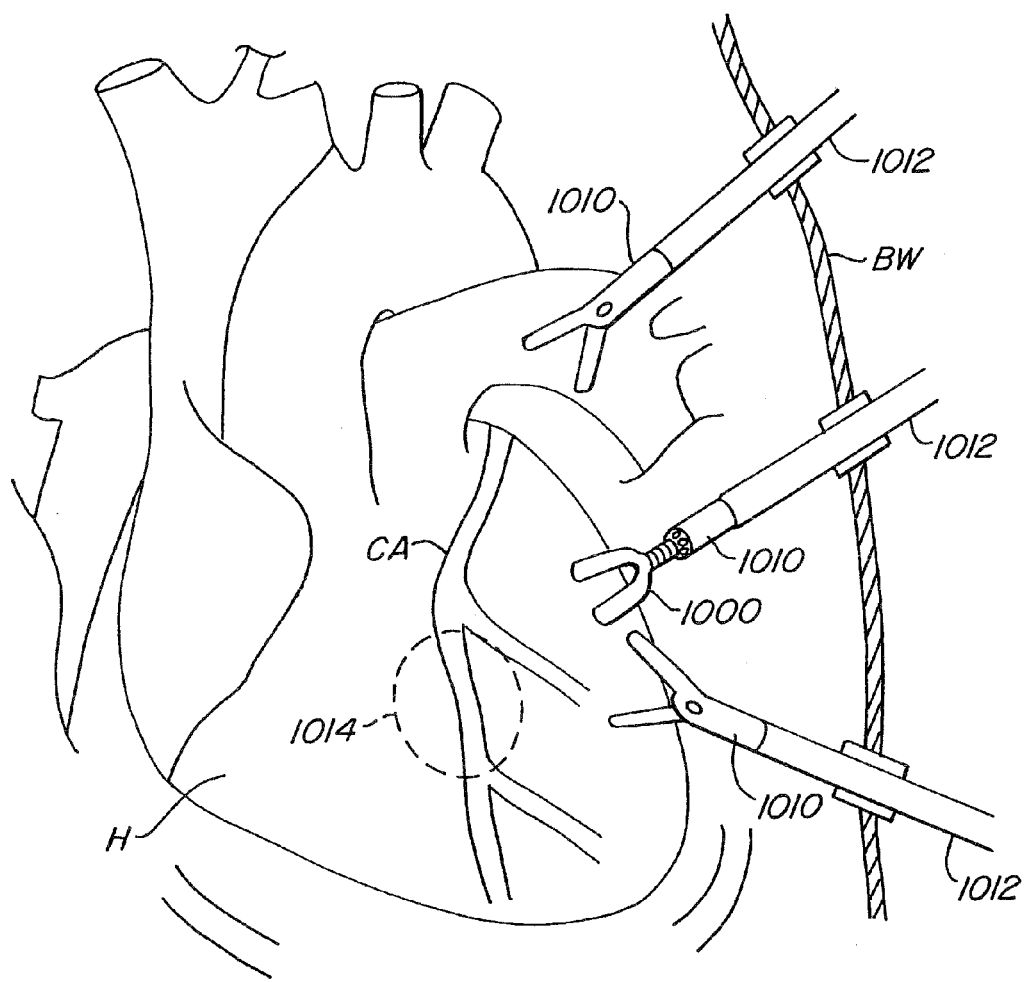
FIG. 2 illustrates access through a body wall with robotically operated surgical instruments and the stabilizer of the present invention.

The present invention is particularly useful in performing minimally invasive robotic coronary artery bypass graft (CABG) procedures. As illustrated in FIG. 2, the heart H remains beating and is accessed through a body wall BW, with robotically operated surgical instruments 1010 introduced through access sheaths or cannulas 1012. It may be appreciated that such a stabilizer 1000 may be used to stabilize any body tissue or organ other than the heart. In these cases, the robotic surgical instruments 1010 would be inserted through any body wall BW, such as the chest wall, abdominal wall, or like. The instruments 1010 may be positioned by pivoting the instruments 1010 about insertion points through the body wall BW by axial movement of the instruments 1010 through the cannulas 1012, rotation of the instruments 1010 about their axes, and articulation of the instruments 1010. When a coronary artery CA is the targeted for anastomosis, a surgical worksite 1014 is identified surrounding the coronary artery CA. Since the heart is beating, the surgical worksite 1014 is in motion. Such motion is inhibited by engaging a surface of the heart H, preferably in the area of the surgical worksite 1014, with a stabilizer 1000.

It should be understood that the stabilizer 1000 need not completely prevent motion of surgical site 1014. Force is applied to the stabilizer 1000 through downward pressure or tensioning of internal cables such that the stabilizer inhibits motion of the surgical worksite 1014 in at least one direction, and ideally in a plurality of directions. As explained more fully in co-pending U.S. patent application Ser. No. 09/436,982, filed Nov. 9, 1999, entitled "Performing Cardiac Surgery Without Cardioplegia"; the full disclosure of which is incorporated herein by reference, residual motion of surgical worksite 1014 may optionally be accommodated by the robotic surgical system by tracking the remaining motion and maintaining alignment between the surgical tools 1010 and the movement of the surgical worksite 1014. Advantageously, the heart may be tolerant of the forces involved in reducing motion of the surgical worksite as compared to attempts to completely cease motion.

Figure 3:
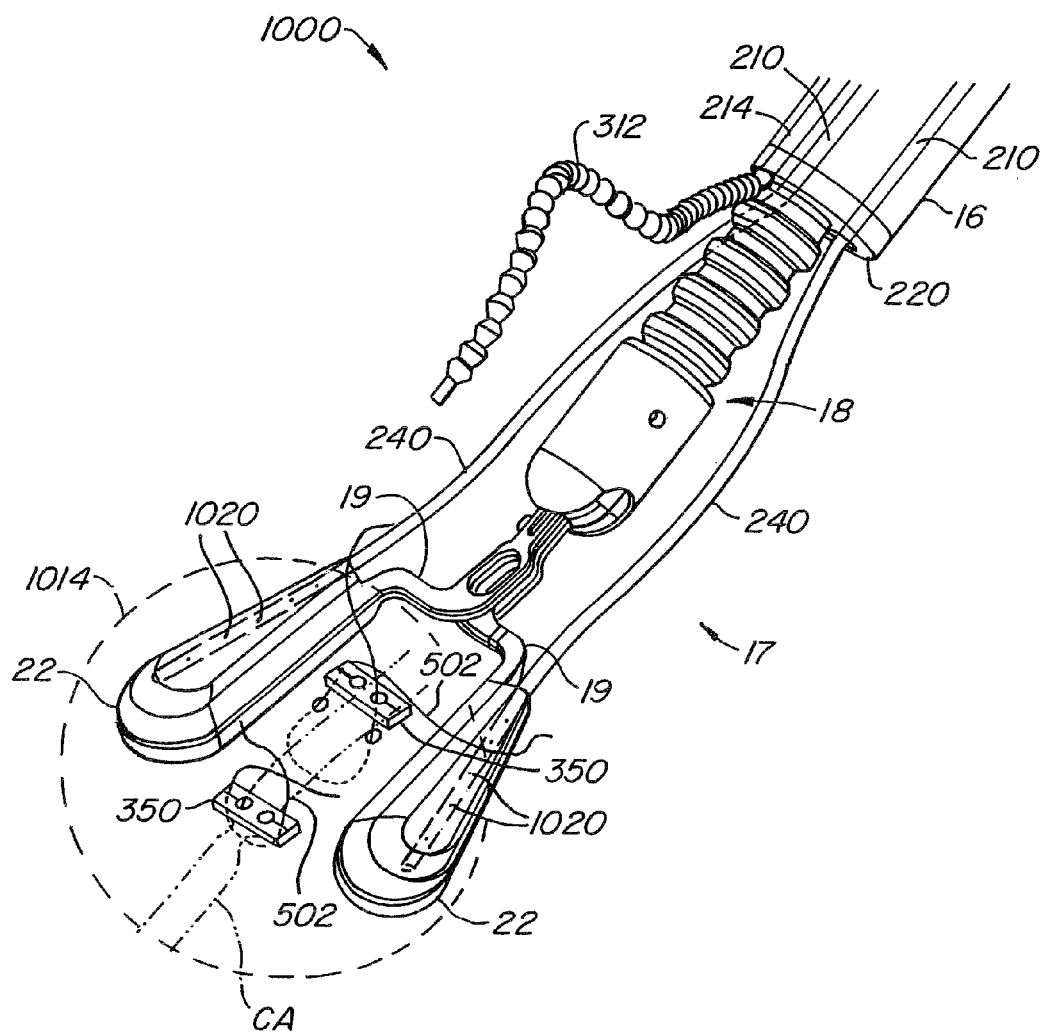
FIG. 3 illustrates an embodiment of the foot of the stabilizer of the present invention and vessel occlusion fasteners positioned to occlude a vessel of interest.

Referring to FIG. 3, an embodiment of the stabilizer 1000 is shown stabilizing the surgical worksite 1014. In this embodiment, the stabilizer 1000 comprises a narrow elongate shaft 16 mounting a stabilizer distal portion or foot 17. The foot 17 comprises a jointed portion or ankle 18 connected with a pair of stabilizer bodies or toe portions 19. As will be described in a later section, the toe portions 19 are actuated and locked in a selected deployment position by a tension cable 20 (not shown). Mounted on each toe portion 19 is a stabilizing surface or tissue engaging member 22. Suction tubes 240, inserted through suction lumens 210 in the shaft 16 so as to extend distally through shaft face 220, connect with each tissue engaging member 22. Suction is provided through suction holes 1020 along the engaging member 22. Such suction holds the stabilizer 1000 in firm contact with the worksite 1014. In addition, an irrigation conduit 312 is inserted through an irrigation lumen 214 in the shaft 16. The conduit 312 is manipulable to direct fluid or gas to the worksite 1014 or any desired location.

As shown in FIG. 3, the members 22 are typically positioned to straddle the coronary artery CA or vessel of interest. To prepare the coronary artery CA for anastomosis, the coronary artery CA is isolated from blood flow by cinching the coronary artery CA upstream and downstream of the desired location for anastomosis. Thus, when the anastomosis is made, blood will not flow out into the workspace. The coronary artery CA may be isolated by any known or suitable method. Likewise, according to the present invention, the coronary artery CA may be isolated with the use of flexible members 502 which are tied to vessel occlusion fasteners or fastening clips 350. Each flexible member 502 is passed under and around the coronary artery CA, as shown, using instruments 1010 inserted within the chest cavity. Each flexible member 502 is then tightened and held by a fastening clip 350, as will be described in further detail.

FIGS. 4A-4E illustrate an embodiment of a fastening clip 350 of the present invention. In the example shown, the clip 350 is configured to attach to two portions of a flexible member 502, such as in creating a loop. In one embodiment, the clip 350 comprises a generally elongate plate-like body 351, which may be rectangular as shown. The body 351 has at least one hole or bore 352 which intersects a radial slot 354. The bore 352 and slot 354 having a depth axis parallel to one another. In the example shown, the body 351 has a first bore 352a and a second bore 352b with respective slots 354a, 354b which lie outboard (towards the plate ends) from their respective bores 352a, 352b.

Figure 4A:
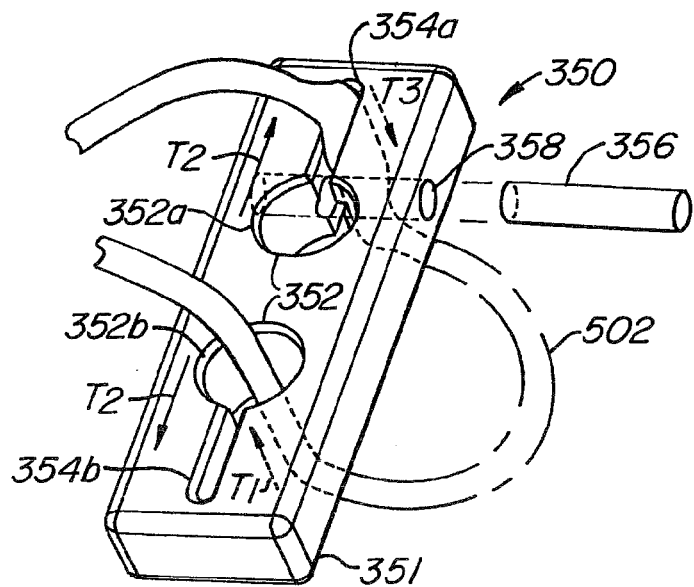
FIGS. 4A-4E illustrate an embodiment of a fastening clip of the present invention.
Figure 4B:
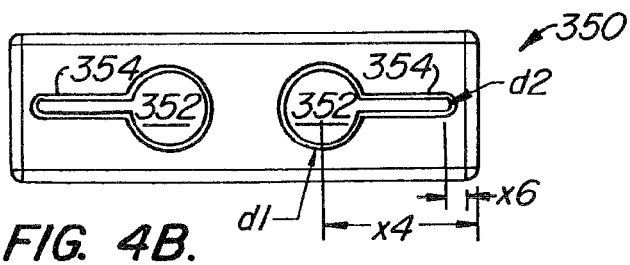
Figure 4C:
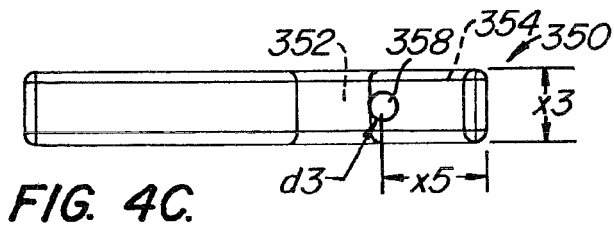
Figure 4E:
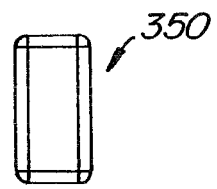
Figure 4D:
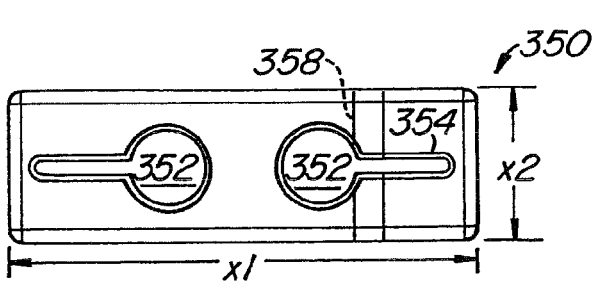

As best seen in FIG. 4A, the flexible member 502 is held within slot 354a. The member 502 may be held by any suitable means. For example, a locking pin 356 may be inserted in a transverse aperture 358 which passes across the bore 352/slot 354 intersection on one side of the clip 350, thus mechanically preventing the member 502 from moving back into the bore 352. The locking pin 356 may be sized to press-fit securely in aperture 358, may be bonded to body 350, or may be permanently or releasably fixed within aperture 358 by known means. The flexible member 502 is then passed under and around the coronary artery CA and threaded through the bore 352b in the direction of arrow T1, the bore 352 diameter (d1) being selected sufficiently larger than the member 502 diameter to permit suitable clearance. The member 502 may then be fixed in place by sliding the member 502 laterally from the bore 352b into the slot 354b in the direction of arrow T2. The slot width (d2) is selected to be sufficiently smaller than the member diameter so as to compress and deform the portion of the member 502 contained in the slot thereby creating substantial frictional forces to prevent the member 502 from being pulled out of the slot in the direction of arrow T3. The friction also resists inadvertent lateral movement of the tube back into the bore 352.

The relationship of the sizes of the flexible member 502, bore 352 and slot 354 is a function of the degree of frictional resistance desired, and may be varied to suit different materials and member constructions. In one preferred example, the clip 350 has a length (x1), width (x2) and depth (x3) of about 0.31, 0.1 and 0.05 inches (about 7.9, 2.5 and 1.3 mm) respectively, has a bore diameter (d1) of about 0.05 inches (1.3 mm), and a slot width (d2) of about 0.01 inches (0.25 mm).

The flexible member 502 may comprise silicone tubing or other flexible material. The flexible member is preferably large enough to catch in the slots 354 but not so large as to require large penetrations about the coronary artery CA or to be ineffective in occluding the artery CA. For exemplary clips 350 having a slot 354 with a width of about 0.010 inches, a preferred Silastic tubing has an outer diameter of about 0.050" and an inner diameter of 0.030", such as that available from QUEST MEDICAL of Allen, Tex. under the product name "Retract-O-Tape". Alternative elastic and inelastic flexible members 502, such as suture material and the like may also be used. The flexible member 502 is tied off to clips 350 using instruments 1010 in an endoscopic procedure, while the heart H is beating and without any need for a thoracotomy or a mini-thoracotomy.

In a preferred embodiment of the clip 350 for vessel occlusion, the member 502 and clip 350 are provided in a sealed package as an pre-assembled, sterilized disposable unit, in which the member 502 is locked into the slot 352 at one end by pin 356, with the other member end free. The tube may be pre-assembled with a suturing needle fixed to the free end.

Once clips 350 have been placed as shown in FIG. 3, the free ends of the members 502 may be tightened by pulling the slack and therefore constricting and occluding the coronary artery CA. After the members 502 have been fixed within the clip slots 354, the clips 350 may be left in place to occlude the coronary artery CA. The stabilizer 1000 may then be repositioned without disturbing the occlusion assembly of member 502 and clip 350. The coronary artery CA is thus stabilized, isolated and ready for the CABG procedure using the robotic surgical instruments 1010.

Figure 5:
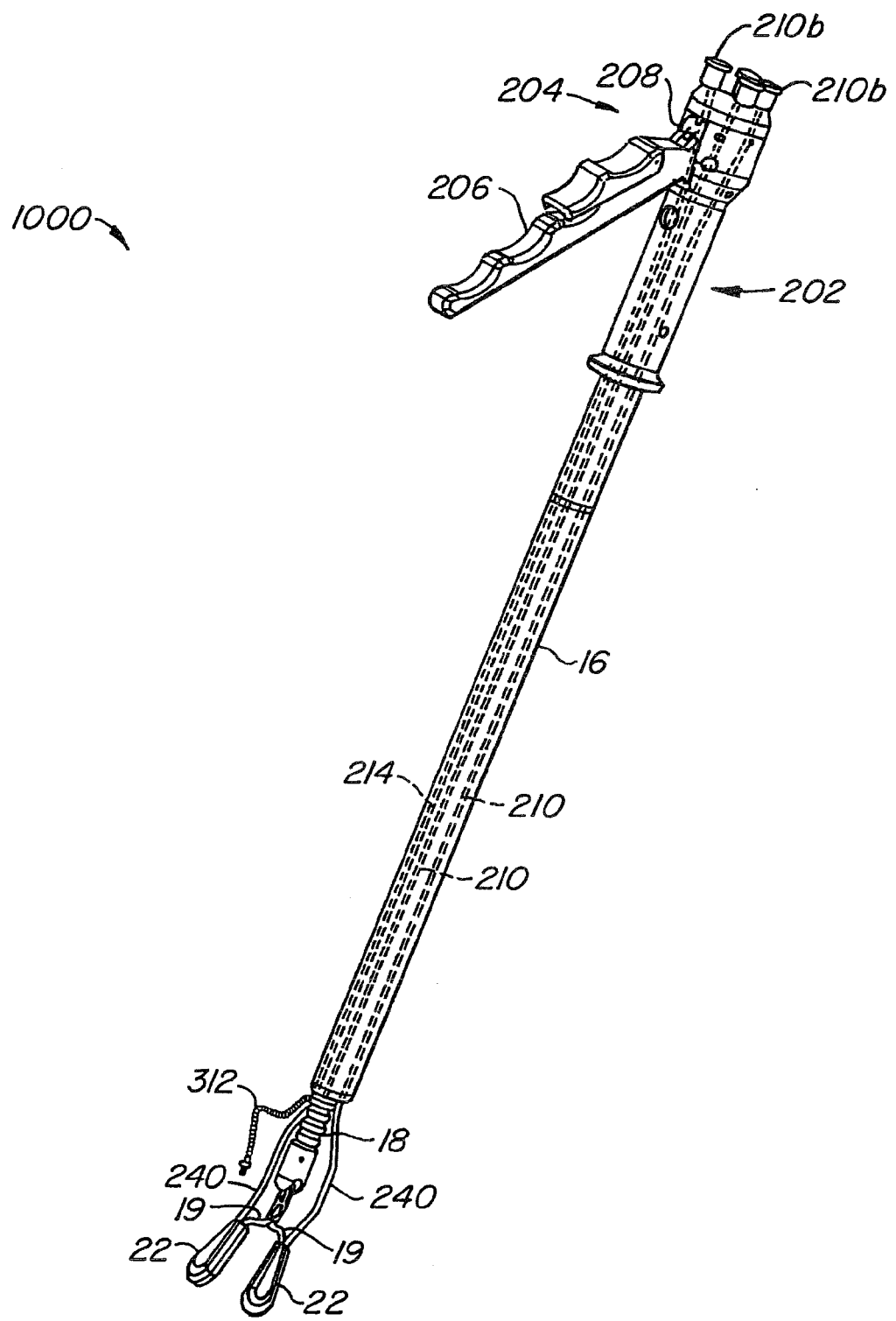
FIG. 5 is a full view illustration of an exemplary embodiment of the stabilizer of the present invention.

FIG. 5 provides a full view of an exemplary embodiment of the stabilizer 1000. As shown, the stabilizer 1000 comprises a narrow elongate shaft 16 mounting a stabilizer distal portion or foot 17. The stabilizer 1000 is shown in an approximate correct scale for an typical instrument having a shaft 16 of approximately 12 mm diameter. The foot 17 comprises a jointed portion or ankle 18 connected with a pair of stabilizer bodies or toe portions 19. Mounted on each toe portion 19 is a stabilizing surface or tissue engaging member 22. Suction tubes 240, inserted through suction lumens 210 in the shaft 16 so as to extend distally through shaft face 220, connect with each tissue engaging member 22. Suction is provided through suction holes 1020 along the engaging member 22. In addition, an irrigation conduit 312 is inserted through an irrigation lumen 214 in the shaft 16. The conduit 312 is manipulable to direct fluid or gas to the worksite 1014 or any desired location. The proximal portion 202 of the stabilizer 1000 includes an adjustable cable tensioner 204, which comprises a handle 206 actuating ratchet mechanism 208 which in turn adjustably engages cable 20 (not shown). As will be described in a later section, the toe portions 19 are actuated and locked in a selected deployment position by the cable 20.

Figure 6B:
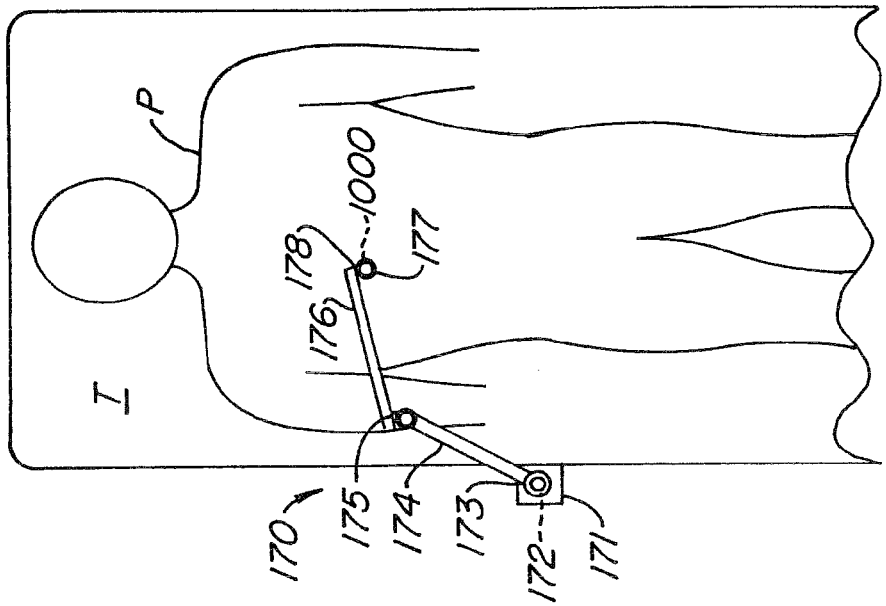
FIGS. 6A-6B illustrate an embodiment of the positioning and clamping system for the stabilizer when used in minimally invasive surgery.
Figure 6A:
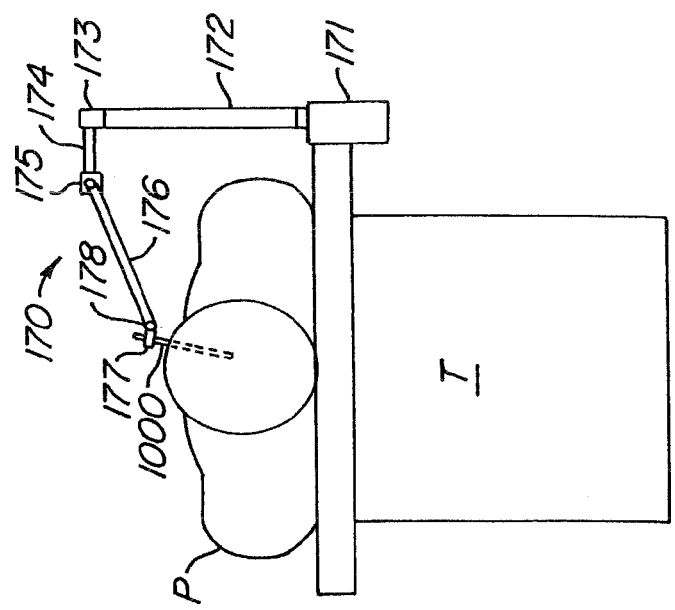

FIGS. 6A-6B illustrate an embodiment of a positioning and clamping system 170 for the stabilizer 1000 when used in minimally invasive surgery, optionally robotic surgery. The system 170 comprises a linkage of a plurality of lockable-releasable joints mounted on a base 171 which is rigidly fixed to the side rail of an operating table T or similar support. In the example shown, the linkage includes a vertical link 172 joined by 1-degree of freedom rotating joint 173 to a horizontal link 174. Link 174 is in turn joined by 2-degree of freedom joint 175 to descending link 176. Link 176 is in turn joined to clamp 177 by a 3-degree of freedom joint 178, such as a lockable ball joint. Clamp 177 adjustably clamps the shaft of stabilizer 1000, which is inserted into the chest of a patient P lying on the table T.

Note that all joints of clamping system 170 are lockable to rigidly hold stabilizer 1000. The elements of the stabilizer may be positioned against the tissue to be stabilized using robotically operated surgical instruments 1010 (such as tissue graspers, needle graspers, forceps or the like, see FIG. 2) and then locked in the desired configuration. Greater or lessor degrees of freedom at each joint are feasible. In addition, each link may be made to lockably telescope, to permit adjustment of link length. The joints may be arranged to all lock/release by means of a single control, or may be arranged to lock in a pre-determined sequence. The joints may each have a selected degree of residual friction in the unlocked state, to assist in manual positioning. The joints may have position encoders, locking status encoders, and pneumatic locking actuators. Additionally or alternatively, the clamp 177 may clamp and position the insertion cannula 1012 (not shown). Various alternative balancing mechanisms may be optionally included to counteract the force of gravity in each link.

Description of the Toe Portions of the Stabilizer

Figure 7A:
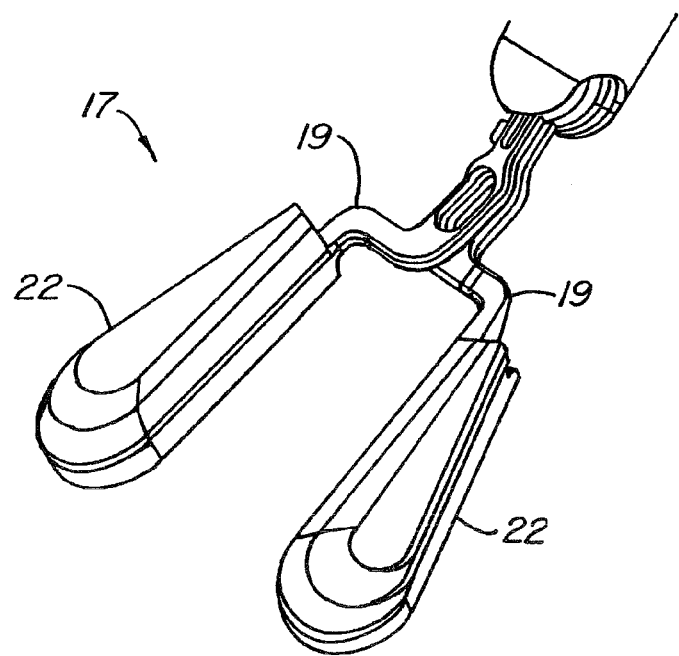
FIGS. 7A-7B illustrate an embodiment of the toe portions of the foot of the stabilizer.
Figure 7B:
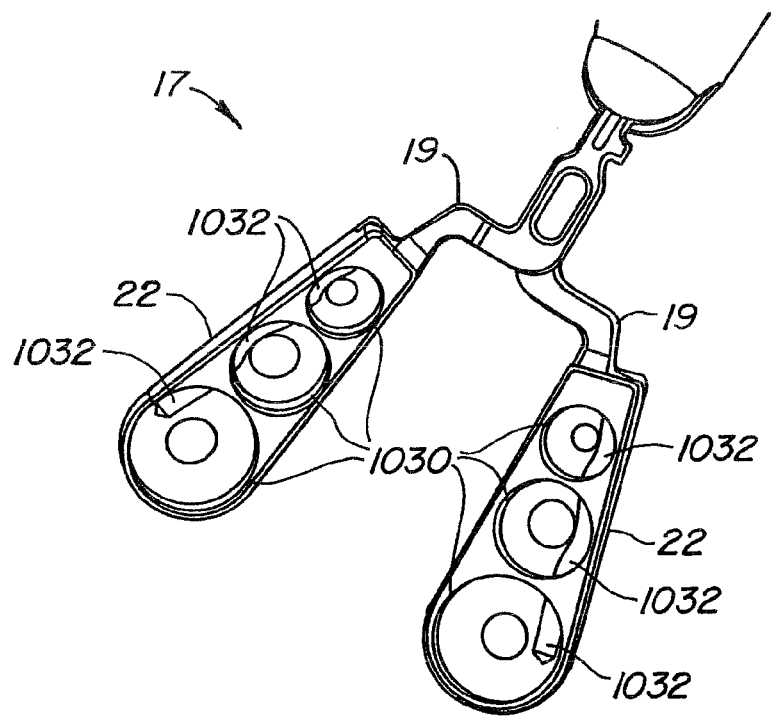

FIGS. 7A-7B illustrate an embodiment of the toe portions 19 of the foot 17 of the stabilizer 1000. Generally, the foot 17 comprises at least two toe portions 19, each portion 19 having a stabilizing surface or tissue engaging member 22 thereattached. FIG. 7A shows a top view of the toe portions 19 which are generally comprised of a smooth surface. FIG. 7B shows a bottom view of the toe portions 19 revealing the underside of the tissue engaging members 22. The underside of the members 22 have one or more suction ports 1030. Suction is provided to the suction ports 1030 by a suction tube 240 (not shown) which connects with the member 22 by insertion of the tube 240 into a suction tube receptacle 1032. Generally, a separate suction tube 240 is inserted into a suction tube receptacle 1032 in each member 22.

Figure 8:
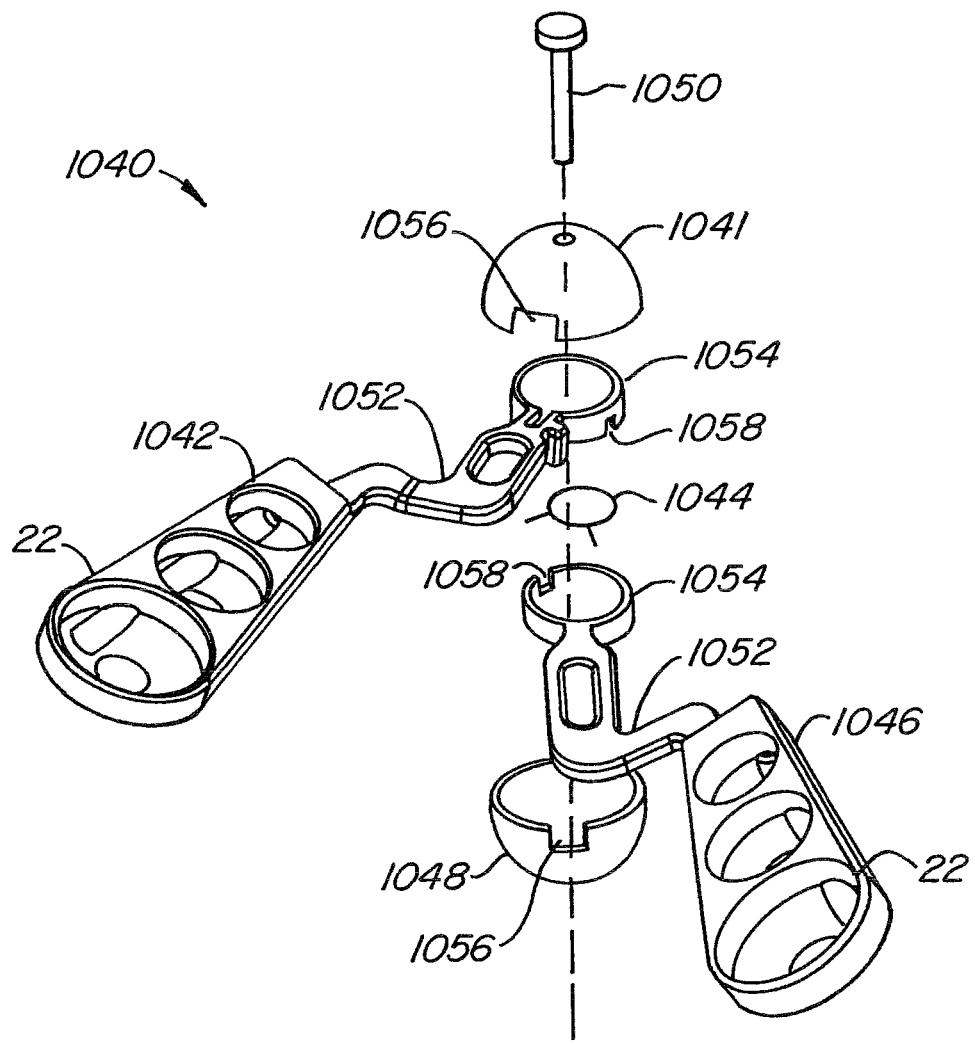
FIG. 8 illustrates the assembly of the toe portions.

The toe portions 19 are shaped and arranged so that the tissue engaging members 22 are generally parallel and spaced apart to permit surgical access to the surface of the heart therebetween. For example, the toes may be spaced from about 5-30 mm apart, preferably about 10-15 mm apart, adequate spacing to straddle a coronary artery CA of interest. As shown in FIG. 8, the toe portions 19 are joined in a toe assembly 1040 which allows the portions 19 and associated members 22 to collapse or rotate inward, reducing the space between the members 22 and allowing the foot 17 to be inserted through a cannula 1012. In this embodiment, the toe assembly 1040 comprises a top ball shell 1041, a first toe portion 1042, a torsion spring 1044, a second toe portion 1046, a bottom ball shell 1048, and a rivet 1050 which is insertable through the above components of the assembly 1040 to hold them in place. As shown, the toe portions 1042, 1046 each comprise a tissue engaging member 22, a strut 1052 and a ring mount 1054. The member 22, strut 1052 and ring mount 1054 may be molded or formed so as to comprise one continuous piece, or some or all of these may be joined to each other. Generally, one continuous piece provides more strength and resistance to fatigue failure.

Figure 9A:
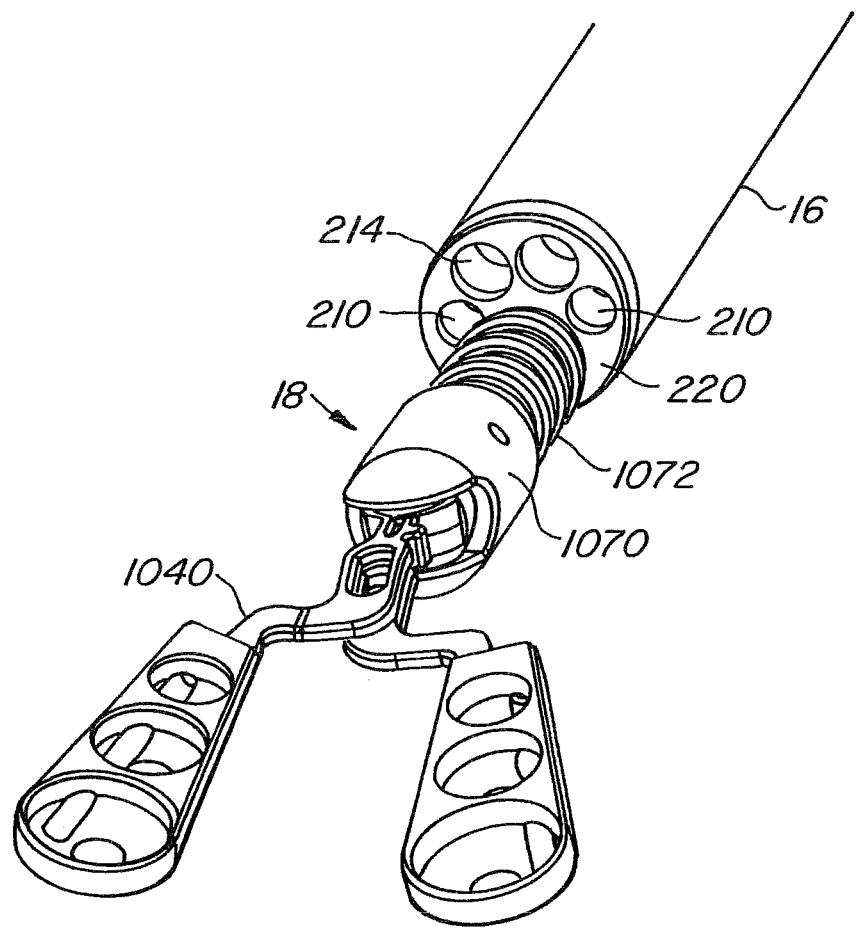
FIG. 9A shows the assembly of the toe portions joined with the ankle.

The components of the assembly 1040 are assembled as shown in FIG. 8, wherein the ring mount 1054 of the first toe portion 1042 fits within the top ball shell 1041 and its strut 1052 fits within a strut notch 1056. The torsion spring 1044 fits within a ring notch 1058 on each ring mount 1054 of the first and second toe portions 1042, 1046. And, the ring mount 1054 of the second toe portion 1046 fits within the bottom ball shell 1048 and its strut 1052 fits within its strut notch 1056. Together, the assembly 1040 provides a spring-loaded, collapsible pair of toe portions 1042, 1046 which are joined at one end to form a spherical split ball shell 1041, 1048. The split ball shell 1041, 1048 is joined with the ankle 18, as shown in FIG. 9A. The split ball shell 1041, 1048 of the assembly 1040 is disposed within the housing 1070 so that the assembly 1040 is freely rotatable.

Figure 9B:
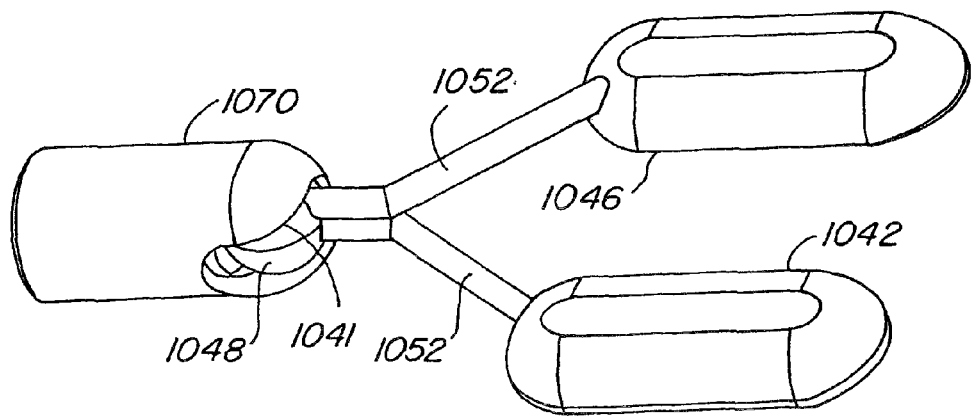
FIGS. 9B-9K illustrate an embodiment of how the toe portions 1042, 1046 may collapse from a deployed or expanded position to a furled or collapsed position.
Figure 9C:
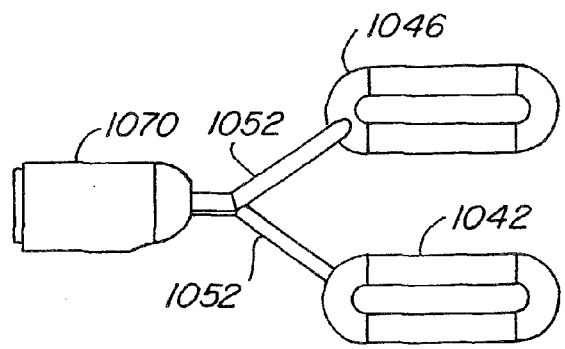
Figure 9D:
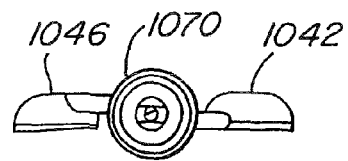
Figure 9E:
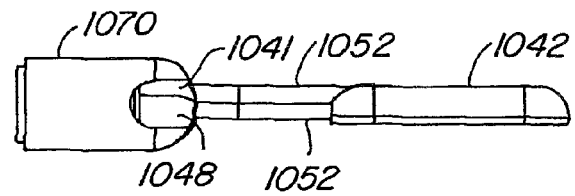
Figure 9F:
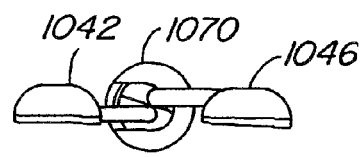
Figure 9G:
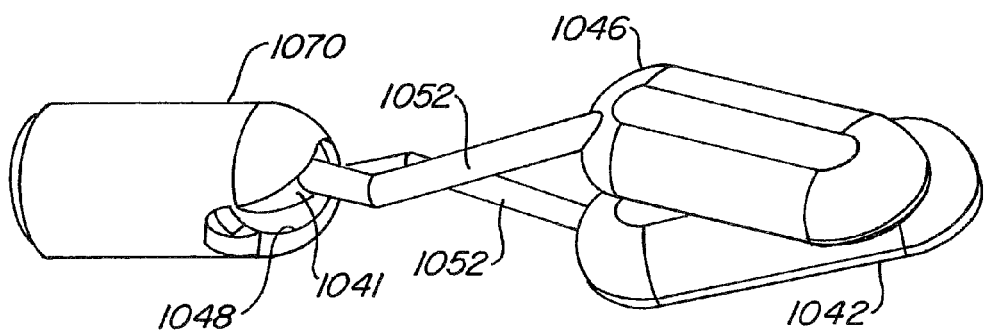
Figure 9H:
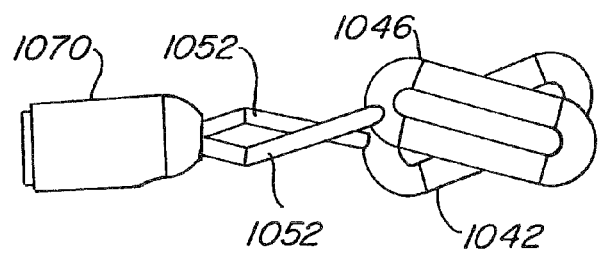
Figure 9I:
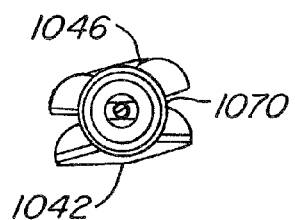
Figure 9J:
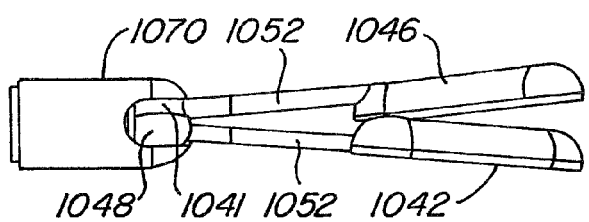
Figure 9K:
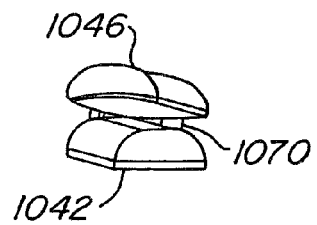

FIGS. 9B-9K illustrate an embodiment of how the toe portions 1042, 1046 may collapse from a deployed or expanded position to a furled or collapsed position for insertion through a cannula. FIG. 9B is a perspective view of the toe portions 1042, 1046 in the deployed position. FIG. 9C is a plan view of the toe portions 1042, 1046, FIG. 9D is a rear elevation view of the toe portions 1042, 1046, FIG. 9E is a side elevation view of the toe portions 1042, 1046 and FIG. 9F is a frontal elevation view of the toe portions 1042, 1046, all in the deployed position. By rotating the toe portions 1042, 1046 within the top ball shell 1041 and bottom ball shell 1048, the toe portions 1042, 1046 may collapse to a furled position illustrated in FIG. 9H. FIG. 9H is a plan view of the toe portions 1042, 1046, FIG. 9I is a rear elevation view of the toe portions 1042, 1046, FIG. 9J is a side elevation view of the toe portions 1042, 1046 and FIG. 9K is a frontal elevation view of the toe portions 1042, 1046, all in the furled position. It may be appreciated that the toe portions 1042, 1046 may collapse in a variety of arrangements and FIGS. 9B-9K serve to illustrate an embodiment of such arrangements.

Description of the Ankle of the Stabilizer

Referring again to FIG. 9A, the assembly 1040 is joined with the ankle 18 in this embodiment as shown. Here, the ankle 18 comprises an outer housing 1070 which is connected with an adjustable neck 1072. The neck 1072 is in turn connected with the shaft face 220 of the shaft 16. As shown, the shaft face 220 includes ports to access the suction lumens 210 and irrigation lumen 214, to name a few. As previously described, the split ball shell 1041, 1048 of the assembly 1040 is disposed within the housing 1070 so that the assembly 1040 is freely rotatable. In addition, the adjustable neck 1072 of the ankle 18 allows the housing 1070 and therefore assembly 1040 to move in all six degrees of freedom relative to the shaft 16.

Figure 10:
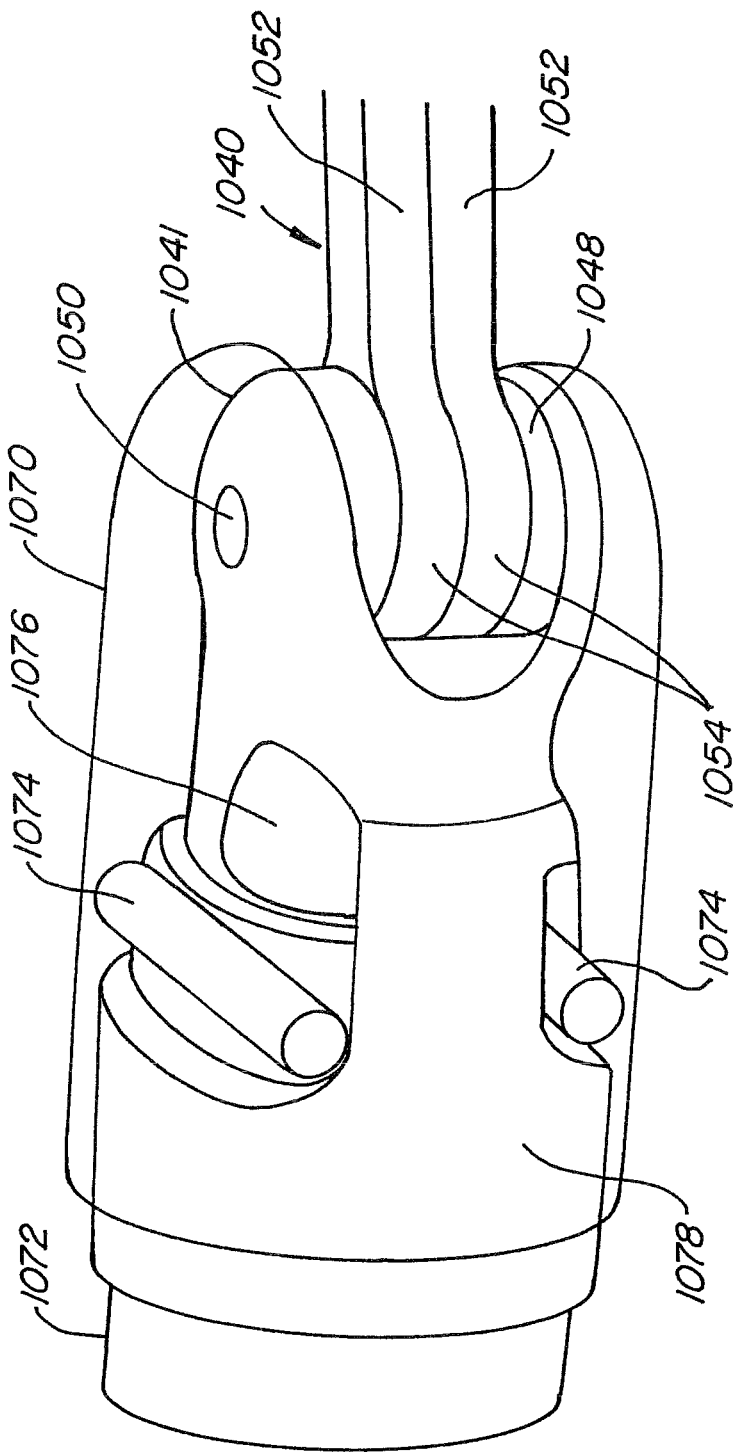
FIG. 10 is a perspective view of a portion of the ankle illustrating the locking mechanisms within the outer housing.

Once the assembly 1040 has been positioned in a desired orientation, the assembly 1040 and ankle 18 may be locked in place. Referring to FIG. 10, such locking may be achieved with the use of a locking ball 1076 which is disposed within an inner housing 1078, both the ball 1076 and inner housing 1078 of which are disposed within the outer housing 1070 as shown. Pins 1074 are fixedly attached to the outer housing 1070 and pass from one side of the housing 1070 to the other, passing adjacent to portions of the inner housing 1078.

Figure 11A:
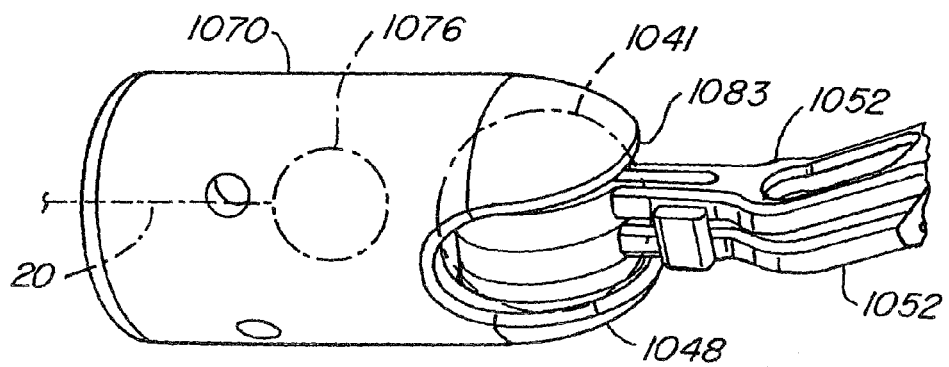
FIGS. 11A-11D) provide detailed views of the components of the locking mechanisms.
Figures 11C, 11D:
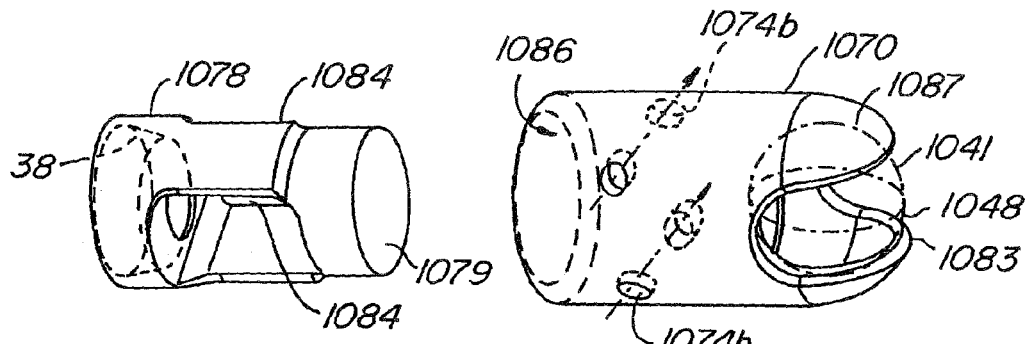
Figure 11B:
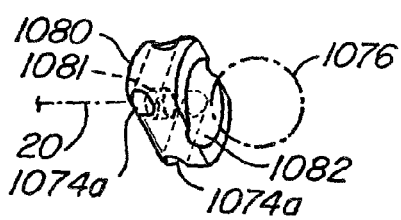

FIGS. 11A-11D provide more detailed views of the components of the locking mechanisms. FIG. 11A illustrates the position of the locking ball 1076, in dashed line, relative to the spherical split ball shell 1041, 1048 of the assembly 1040 within the outer housing 1070. The inner housing 1078 and other components have not been included in this view for clarity. FIGS. 11B-11D provide an exploded view of the additional components to illustrate how they fit together.

FIG. 11B illustrates a slide bearing 1080 having a central bore 1081 and a hemispherical mating surface 1082. The locking ball 1076 is positioned so that it is mateable against the hemispherical mating surface 1082 and the cable 20 passes through the central bore 1081 as shown. The slide bearing 1076 also includes pin apertures 1074a through which pins 1074 are fittable as illustrated by arrows.

FIG. 11C illustrates the inner housing 1078 having a slot 1084 and a hemispherical mating surface 1079. The slide bearing 1080 and locking ball 1076 fit within the slot 1084 of the inner housing 1078, as indicated by dashed lines.

FIG. 11D illustrates the outer housing 1070 having a bore 1086 and an end slot 1083 as shown. In addition, the housing 1070 has pin apertures 1074b which pass from one side of the outer housing 1070 to the opposite side 1070 side of the outer housing 1070. The inner housing 1078 fits within the bore 1086 of the outer housing 1070, as indicted by dashed lines. The pin apertures 1074a align with pin apertures 1074b so that pins 1074 may be passed through the apertures 1074a, 1074b and fixed in place by pressure fitting, threads, bonding or other known means. Thus, in the assembled ankle 18, the pins 1074 serve to fixedly connect the slideable member 1080 to the outer housing 1070. However, the slot 1084 within the inner housing 1078 provides sufficient clearance so that the inner housing 1078 is free to move slightly in an axial direction within bore 1086 when the cable 20 is relaxed. This is one aspect which allows movement of the ankle 18 when the cable 20 is relaxed. The spherical split ball shell 1041, 1048, as illustrated in dashed line, is received within the end slot 1083 and is mateable against hemispherical mating surface 1079.

Figure 11E:
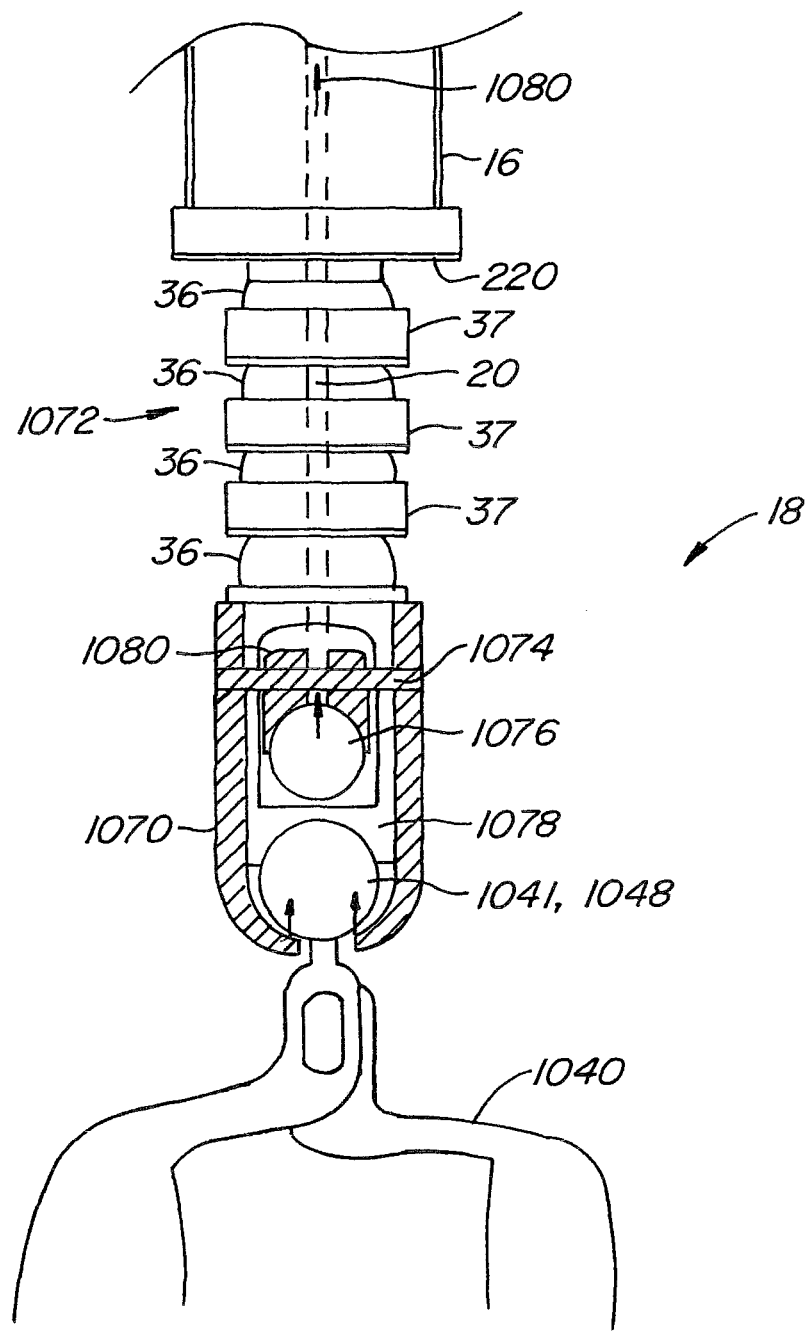
FIG. 11E provides a cross-sectional view of the ankle and the components associated with the locking feature.

FIG. 11E provides a cross-sectional view of the ankle 18 and the components associated with the locking feature. As shown, the locking ball 1076 is attached to a tension cable 20 which extends through the neck 1072 and along the shaft 16. The locking ball 1076 is disposed against the slide bearing 1080, within the inner housing 1078 and the outer housing 1070, and can freely move within the inner housing 1078 when the adjusting the ankle 18. The pins 1074 are fixedly attached to the outer housing 1070 and pass through the slide bearing 1080 so the pins 1074, slide bearing 1080 and outer housing 1070 are moveable as a unit as identified by shading. The spherical split ball shell 1041, 1048 of the assembly 1040 is disposed within the outer housing 1070 as shown so that the shell 1041, 1048 and the locking ball 1076 are separated by the hemispherical mating surface 1079 of the inner housing 1078. The shell 1041, 1048 can freely move between the inner housing 1078 and outer housing 1070 when adjusting the ankle 18 or assembly 1040.

In this embodiment, the neck 1072 is comprised of a series of interlocking balls 36 and intermediate socket rings 37. The balls 36 each have a hollow core through which extends the distal portion of the cable 20. Joints between the balls 36 and the rings 37 may be sealed by the rings or may alternatively or additionally have an outer covering of a flexible material, such as an extruded heat-shrinkable polymeric material. Each ball 36 may be rotated independently against an adjacent ring 37 to allow the neck 1072 to be positioned. Once the neck 1072 and the assembly 1040 are positioned, they may be locked in place by applying tension to the cable 20 in the direction of arrow 1080.

As cable 20 is tensioned, the outer housing 1070 moves slightly proximally relative to the inner housing 1078, urging the spherical split ball shell 1041, 1048 into frictional contact with the hemispherical mating surface 1079. As the shell 1041, 1048 bears upon inner housing 1078, the inner housing 1078 in turn bears upon one or more of the balls 36 and intermediate sockets rings 37 of the ankle 18. By continuing to apply tension to the cable 20, the locking ball 1076 and shell 1041,1048 are eventually held tightly and restricted a movement. Thus, it may be seen that when the cable 20 is tensioned, the tension force is communicated sequentially by joint contact forces from locking ball 1076 to slide bearing 1080 to outer housing 1070 to shell 1041,1048 to inner housing 1078 and finally to the balls 36 and socket rings 37. The mechanical reaction force which balances the tension force on cable 20 is provided by the contact of the most proximal ball joint 36 which is fixedly mounted to shaft face 220. The contact forces so generated provide a frictional resistance to rotational movement at each of these joints, causing the foot assembly to become locked joint-by-joint throughout.

Note that although the mating surfaces of the contacting elements such as balls 36, and socket rings 37 are exemplified above as being of a generally spherical contour, other alternative surface contours are feasible and may be desirable. FIG. 12A illustrates an embodiment of a portion of the neck 1100 showing the balls 36 interlocked with the rings 37. Here, a generally hemispherical surface 1104 of ball 36 mates with a generally hemispherical surface 1102 of socket ring 37 over a somewhat distributed contact area, since surface 1104 approximately conforms in shape to surface 1102. When the neck 1072 is placed in compression (such as by applying tension to a central tension cable, not shown), the summation of forces over the contact area tends toward the centerline of the neck 1072, and may be represented by arrow 1084, acting at an angle θ. In this example, the angle θ is typically about 40 degrees for the contour of the surface 1104.

Figure 12B:
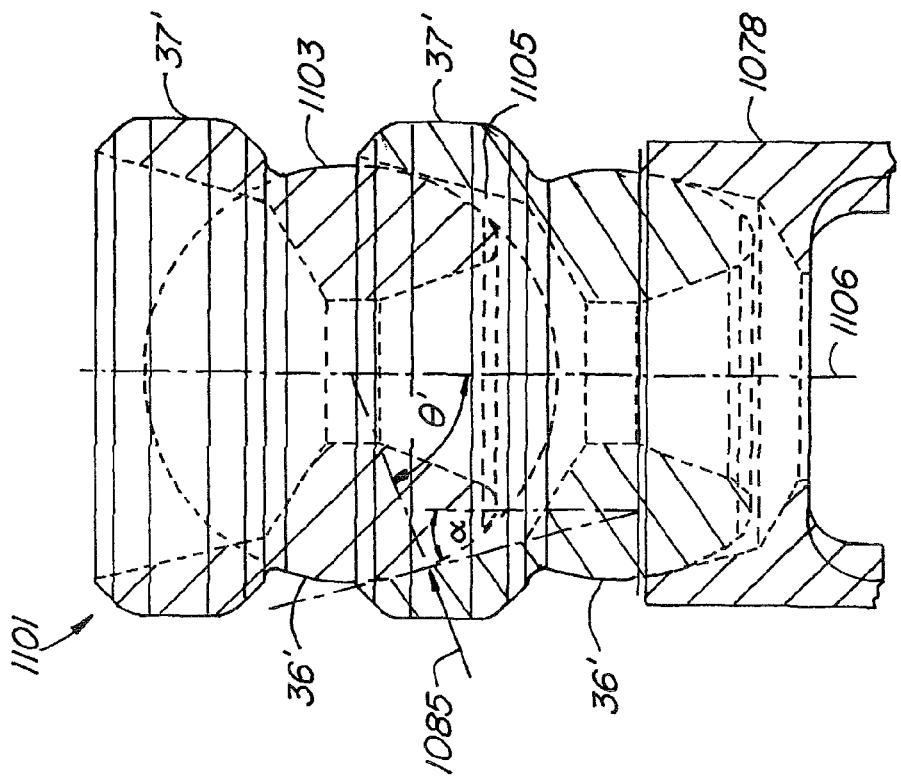
FIGS. 12A-12B are cross-sectional depictions of the balls and rings of the neck portion of the ankle wedged together to frictionally hold the neck in position.
Figure 12A:
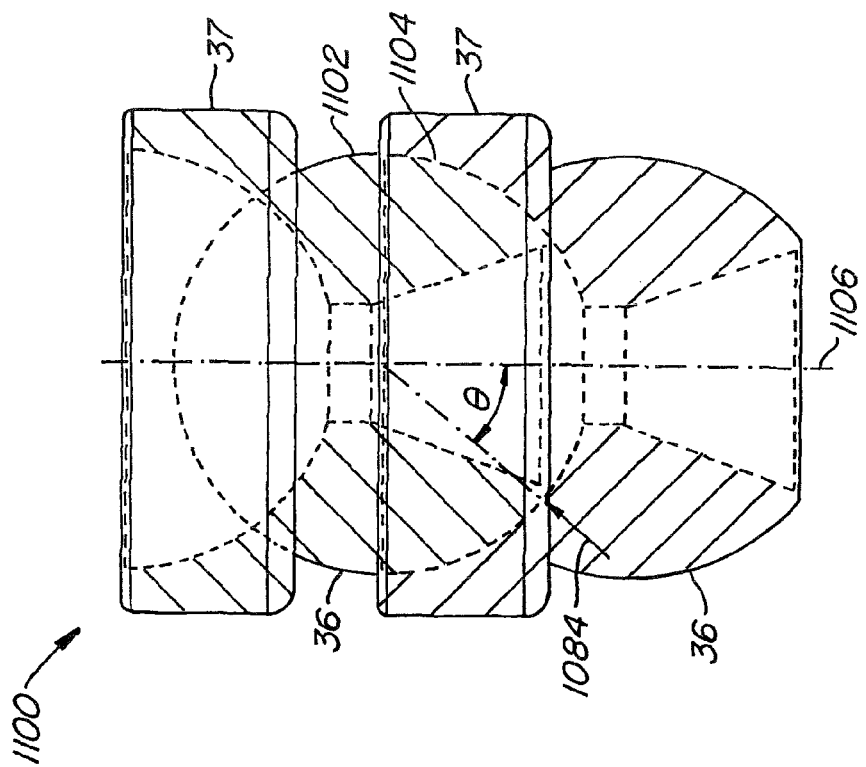

In an alternative embodiment a portion of the neck 1101, as shown in FIG. 12B, a generally hemispherical surface 1103 of alternative ball 36' contacts a generally conical surface 1105 of alternative socket ring 37'. Due to the contours of the surfaces 1103, 1105, the surfaces 1103, 1105 have considerably more concentrated contact area. This is because surface 1103 becomes approximately tangent to surface 1105 only at a narrow region of tangency. Thus, when assembly 1101 is placed in compression, the summation of forces over the contact area is restricted to the region of tangency, as represented by arrow 1085, acting at an angle θ'. The angle θ' of the region of tangency may be adjusted by suitably selecting the conical angle α of surface 1105. In the example of FIG. 12B, the conical angle α may be about 20 degrees and the angle θ' may be about 69 degrees.

Due to the generally hemispherical contour of surface 1103, the alternative embodiment of the portion of the neck 1101 will have a similarly shaped tangent region between ball 36' and socket ring 37' in the event that these elements are rotated out of the parallel alignment shown in FIG. 12B.

Note that the contact between a hemispherical surface (approximated in this example by surface 1103) and a conical surface (approximated in this example by surface 1105) may be idealized as a circle perpendicular to the center axis, although a real structure will react to applied contact forces over a region of finite area, the shape of which may be a function of surface irregularities, material properties, deformations and the like.

In addition, although in the preferred embodiments the surfaces 1102, 1103, 1104, 1105 may be axially symmetrical surfaces of revolution, they need not necessarily be so, such as, for example, where it is desired to limit motion within the neck portions 1100 or 1101 to a single degree of rotational freedom.

As mentioned above, the larger contact angle θ' of neck embodiment 1101 provides a stronger locking frictional force resisting rotation about the joint than is provided by the smaller contact angle θ of neck embodiment 1100, for a given overall neck diameter and compression force. The relationship between the angle θ and θ' and the applied perpendicular breakaway force for the joint may be approximated by the following formula:

$$Fa = \mu F_t R/(2d \cos \theta)$$

where:
$Fa$=breakaway force (locking effect)
$F_t$=tension force on cable (causing joint compression)

R=joint radius (e.g., hemispherical radius)
d=lever arm of applied Fa from joint center (e.g., distance from toe to joint center).
θ=coefficient of static friction (function of material properties, lubrication effect of body fluids, etc.)

Thus the relative breakaway force for the two exemplary embodiments shown in FIGS. 12A and 12B is approximately proportional to the inverse ratio of cosines the contact angles or:

$$Fa'/Fa=\cos\theta/\cos\theta'=\cos(40°)/\cos(69°)=2.14$$

Thus it may be seen that the alternative neck embodiment 1101 has a substantially enhanced locking effect relative to neck embodiment 1100, given comparable operative conditions.

A suction-enhanced beating heart stabilizer may be constructed for surgery performed via a large sternotomy which is held open by a sternal retractor. See, for example, Borst et al., U.S. Pat. No. 6,015,378, the disclosure of which is incorporated herein by reference. In a stabilizer intended for this purpose having cable-locked ball and socket type joints, the locking force may be increased by selecting a larger ball joint assembly, sized to provide a desired breakaway force for a selected cable tension.

However, in minimally invasive cardiac surgery, such large incisions and accompanying tissue damage are desirably avoided, and the stabilizers embodiments of the present invention may be of a size suitable for insertion through a small cannula placed in a small body wall incision, such as in the intercostal space between ribs. For this purpose, the joint size is preferably kept small. Thus, the ability of the alternative neck embodiment 1101 to provide a large locking force within the small joint diameter particularly suits it for use in instrumentation intended for minimally invasive or endoscopic surgery.

Description of the Suction Tubes

Suction tubes 240 are insertable through suction lumens 210 in the shaft 16, as previously shown in FIG. 3 and FIG. 5, so as to extend distally through shaft face 220. FIGS. 13A-13B illustrate an embodiment of a suction tube 240. As shown in FIG. 13A, the suction tube 240 has an elongated shape with a stopper portion 242 at proximal end 1092 and a flexible portion 244 at distal end 1094. FIG. 13B is an enlarged view of the flexible portion 244. The tubes 240 may be made to be disposable or may be readily sterilizable for reuse. Typically, the flexible portion 244 is made from a flexible polymer, which may optionally be coil-reinforced as shown to prevent kinking and suction collapse. The suction tube 240 includes a suction tip 1090 disposed at the distal end 1094 having one or more suction holes 1020.

Figure 14:
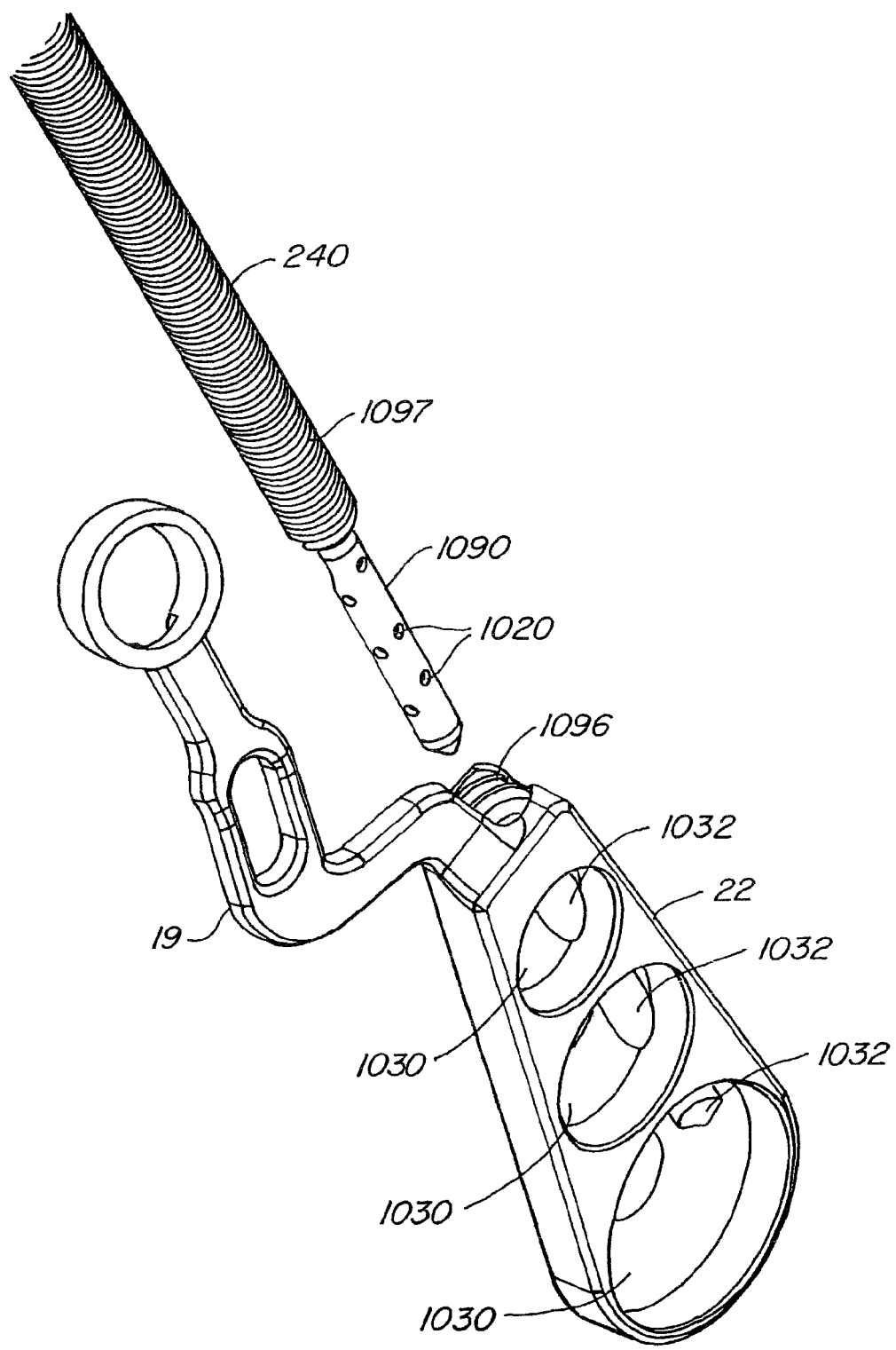
FIG. 14 shows the insertion of a suction tip into a suction tube receptacle in a tissue engaging member.

The suction tip 1090 is insertable through a lumen port 210b, shown in FIG. 5, and through the suction lumen 210 until the stopper portion 242 frictionally engages and seals to the lumen port 210b. At this point, the suction tip 1090 protrudes through the shaft face 220. As shown in FIG. 14, the suction tip 1090 is then insertable into the suction tip receptacle 1032 in the tissue engaging member 22. Note that the entry to the receptacle 1032 may have thread-like grooves to "snap fit" to reinforcement coils 1097 at the end of portion 240. The receptacle 1032 extends along the member 22, passing through the suction ports 1030. Generally, the tip 1090 is positioned so that the suction holes 1020 align with the suction ports 1030. As described previously, suction is provided through the suction holes 1020 along the engaging member 22. Such suction holds the stabilizer 1000 in firm contact with the worksite 1014.

Description of the Irrigator

FIGS. 15, 16, 17, 17A-17B illustrate an embodiment of an irrigation device or irrigator 310 as previously shown in FIG. 3. The irrigator 310 is insertable through the irrigation lumen 214 in the shaft 16 of the stabilizer 1000 so that it protrudes outwardly from the shaft face 220. Fluids, such as liquids or gases, may be delivered to the worksite 1014 through the irrigator 310 as needed. The fluids may be used for a number of surgical purposes, such as to remove blood from the anastomotic site. For example, the irrigator 310 may be positioned by a surgeon so that it is adjacent an anastomosis site, leaving clearance for working tools, and a flow of saline solution may be adjusted to provide a steady drip to remove blood and the like. Alternatively, a flow of carbon dioxide may be established to blow liquids away from the surgical site.

In the embodiment illustrated in FIG. 15 and FIG. 16, the irrigator 310 comprises an elongate (and preferably somewhat flexible) conduit 312 and a flexibly adjustable dispenser 314. The dispenser 314 terminates in a nozzle or spout portion 316. In this embodiment, the irrigator 310 also includes a mounting plug or lumen connector 318 and a fluid supply connector 320 in communication with conduit 312.

The diameter or width dimensions of conduit 312 is selected to be insertable into and through the lumen 214 in the stabilizer shaft 16. As the conduit 312 is fully inserted into the lumen 214, the spout portion 316 extends through the distal lumen opening in shaft face 220. Preferably, the diameter or width of the dispenser 314 and nozzle 316 is also selected to be insertable through lumen 214 (note that dispenser 314 preferably may be straightened for convenient insertion).

In a preferred embodiment, the irrigator 310 is provided in a sealed package as an pre-assembled, sterilized disposable unit, and is inserted in and mounted to the separately-sterilized stabilizer 1000 during surgical preparation. The irrigator 310 preferably comprises a conventional biocompatible polymer material. Alternatively, the irrigator 310 may be installed in the stabilizer 1000 in separate components, which are coupled after the conduit is inserted into lumen 214, e.g., dispenser 314 may be coupled to conduit 312 after the conduit is inserted in lumen 214.

As illustrated in FIG. 17 and FIGS. 17A-17B, the adjustable dispenser 314 preferably comprises an "snap bead" type assembly, including a plurality of sub elements or "beads" 322, coupled end-to-end in chain-like fashion. Each substantially identical "bead" sub-element includes a proximal socket portion 324, a distal ball portion 326, and an internal longitudinal conduit portion 328 open at both ends. The ball 326 is of a size selected to "snap-fit" into the conforming-shaped socket portion 324 of the adjoining bead 322, the beads 322 preferably comprising a molded, elastic polymer material. The shape of the ball 326 and socket 324 is configured to form a ball-and-socket joint between each pair of adjacent beads 322, so as to provide a substantially effective fluid seal while permitting a substantial range of rotational motion in two degrees of freedom.

The "snap-fit" dimensions are preferably selected so as to provide a secure chain assembly and also substantial residual normal force between the inner surface of socket 324 and the outer surface of ball 326, so as to create frictional resistance to rotational movement between adjacent beads 322. The rotational freedom allows the shape of the dispenser 314 to be conveniently adjusted, e.g., by a surgeon using a robotic end effector such as a forceps, while the frictional resistance causes the adjusted shape of dispenser 314 to remain fixed after it is released by the surgeon. The inter-communicating conduit portions 328 of the beads 322 form a continuous lumen from conduit 312 to nozzle 316.

Optionally, alternative adjustable-shape tubular elements known in the art may be included in the dispenser 314. However, the preferred ball-and-socket dispenser 314 described herein has been found to provide a conveniently and precisely adjustable member which is stable and has little or no "spring-back", i.e., it "stays where the surgeon puts it". This eliminates trial-and-error effort and time consumption during adjustment due to springiness and over-correction, and allows the dispenser 314 to be quickly re-positioned as desired to suit changing surgical requirements.

Optionally, a thin, flexible tether filament 330 may be included passing longitudinally along the axis of the dispenser 314, e.g., being fixed at one end to nozzle 316 at a mount 331 and extending through the central lumen of dispenser 314 into conduit 312. The tether 330 may be fixed at its other end to a convenient point (not shown) along the conduit length or proximal to the conduit.

A conventional fluid supply may be coupled to connector 320. The fluids may include liquids (e.g., saline solution, and the like) or gases (e.g., insufflation gas, carbon dioxide, and the like). The fluid flow rate may be controlled by conventional fluid supply controls, such as valves and the like.

The irrigator of the invention may also be mounted to supports or instruments other than the stabilizer 1000, and used where ever an adjustable endoscopic dispenser of surgical fluids is desired. It has been found that the convenient and repeatable adjustability of the irrigation dispenser 314 permits it to be used additionally or alternatively to direct fluids on to surgical accessories, such as to clear blood or other substances from an endoscope objective element, and the like.

Description of the Handle

As previously described, the ankle 18 of the stabilizer 1000 may be positioned against the target worksite 1014 by manipulation with the use of robotic surgical instruments 1010 within the chest cavity. Once the stabilizer 1000 has been positioned, the ankle 18 may be locked in place to prevent movement of the toes 19 and to maintain proper orientation of the stabilizer 1000. As mentioned, such locking is achieved by applying tension to the cable 20 which passes through the shaft 16 to the ankle 18 where it is attached to the locking ball 1076. Such tension is applied to the cable 20 by actuating a cable tensioner assembly 204 on the stabilizer 1000.

Figure 20:
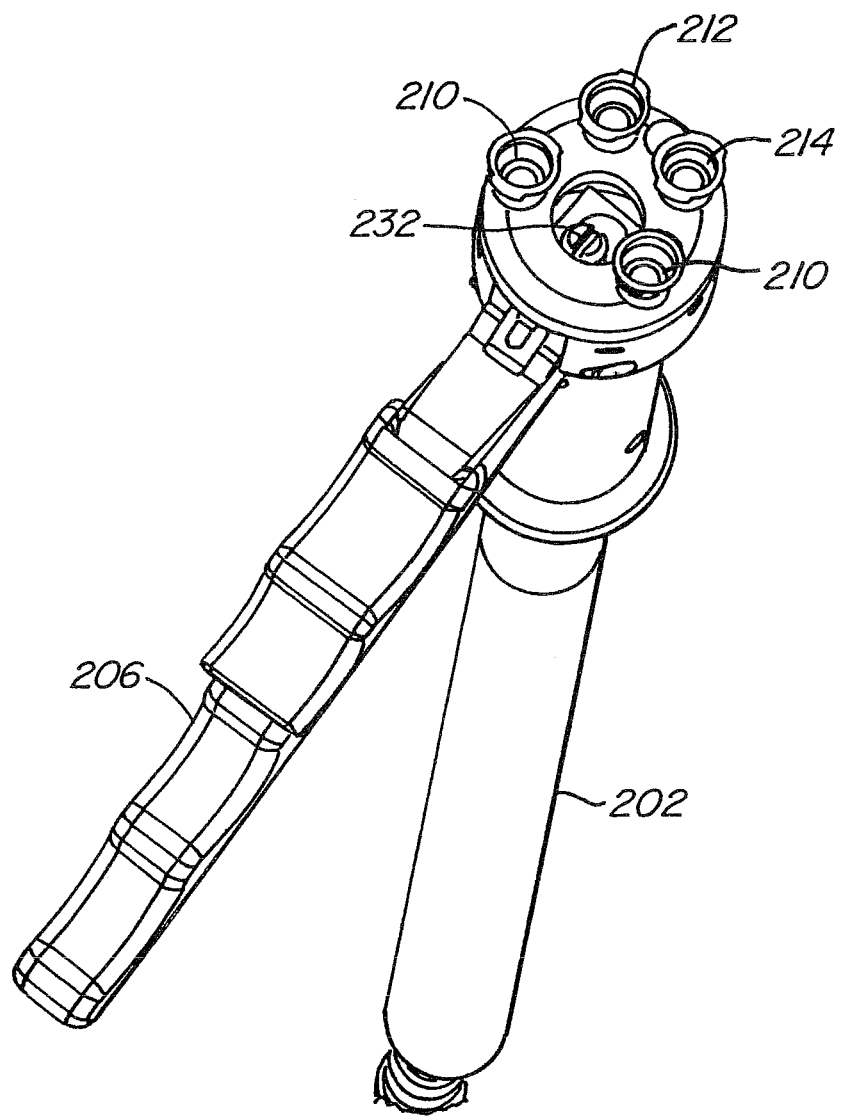
FIG. 20 provides an end view of the handle illustrating exposure of the end screw for adjustment.

FIG. 18 illustrates an embodiment of the cable tensioner assembly 204 of the present invention, shown at the proximal end of the shaft 16. The cable tensioner 204 comprises a pivotal handle 206 and ratchet mechanism 208. FIG. 19 illustrates the mechanisms within the handle 206 which connect the handle 206 with the cable 20. As shown, the handle 206 is pivoted to body 202 at pivot pin 222 and has an inboard portion 230 which is attached to cable 20. Thus, as handle 206 is rotated downward in the direction of arrow T1, the tension applied from pivot pin 222 to inboard portion 230 causes the cable 20 to be stressed and retracted upward in the direction of arrow T2. Ratchet pawls 224 are pivoted above handle 206 to engage surface 226, so as to lock the cable tensioner 204 by preventing handle 206 from pivoting upwards. The cable tension at any given position of handle 206 can be adjusted by end screw 232, which is threaded to a terminus of cable 20 and bears on the attachment 230 so as to adjust cable tension. FIG. 20 provides an end view of the handle 206 illustrating exposure of end screw 232 for adjustment.

Figure 22:
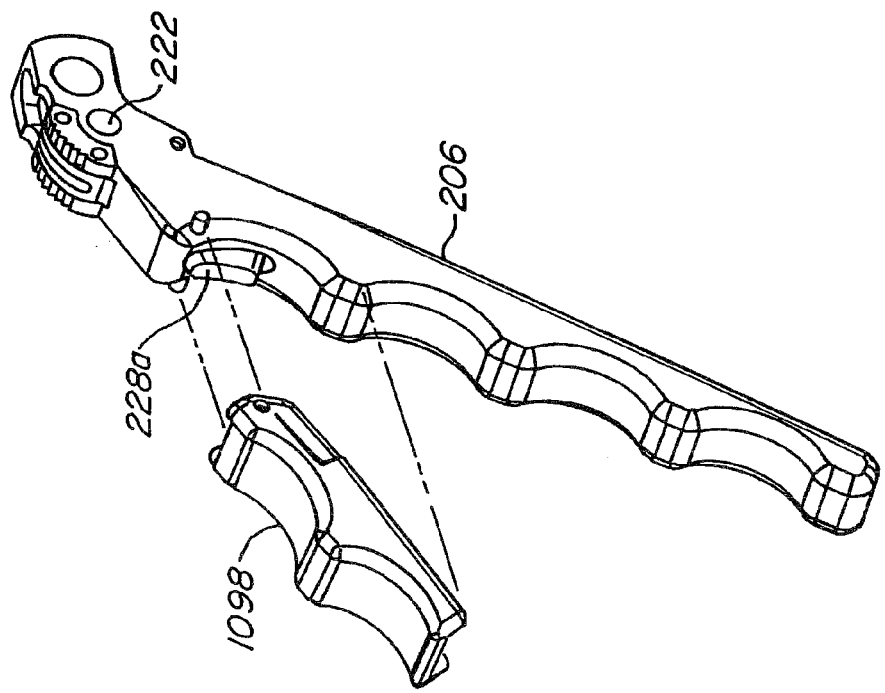
FIGS. 21-22 illustrate a cover handle which is pivotally attached to the handle to assist in depressing the release button.
Figure 21:
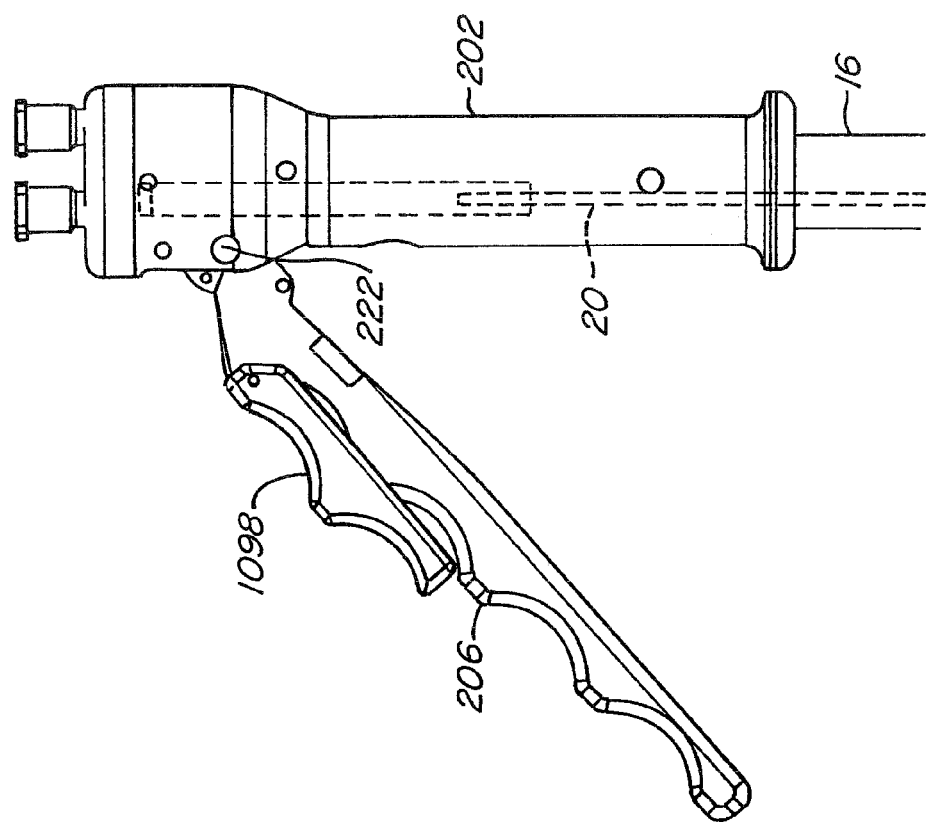

The cable 20 is released by pressing a release button 228a located on the handle 206, as illustrated in FIGS. 18-19. By pressing the release button 228a, the surgeon or assistant can quickly release the cable tension for removal or repositioning of the stabilizer 1000. The release button 228a is mechanically linked (linkage not shown) to release actuator 228b, which pushes the pawl 224 away from ratchet toothed surface 226 when button 228a is depressed, so as to allow the handle 206 to be released. To assist in depressing the release button 228a, some embodiments include a cover handle 1098 which is pivotally attached to the handle 206, as illustrated in FIG. 21 and FIG. 22. By squeezing the cover handle 1098 against the handle 206, the underlying release button 228a is depressed. This simply allows the lever action of the cover handle 1098 to apply a stronger force to the button 228a. In some embodiments, the cover handle 1098 is built into the handle 206.

The employment of a single-handle cable tensioner 206 leaves substantial volume of body 202 free for routing of one or more supply lumens for such purposes as suction, irrigation, and insertion of surgical accessories. In the example shown in FIG. 20, there are four lumens, two suction lumens 210 an accessory insertion lumen 212 and an irrigation lumen 214, each with a corresponding access port in the proximal end or face of body 202. The lumens each extend within shaft 16 (which also houses tension cable 20) to a distal port in the distal face 220 of shaft 16. The accessory insertion lumen may be used to insert various surgical devices, such as clamps, retractors, a holding device to support a graft vessel (e.g. internal mammary artery (IMA)), or the like.

ADDITIONAL EMBODIMENTS

Additional embodiments of the present invention illustrate alternative or additional aspects of the stabilizer described above. Although only a limited number of such embodiments are described, it is understood that such description is not intended to limit the scope of the present invention.

Additional Embodiment #1

Figure 23:
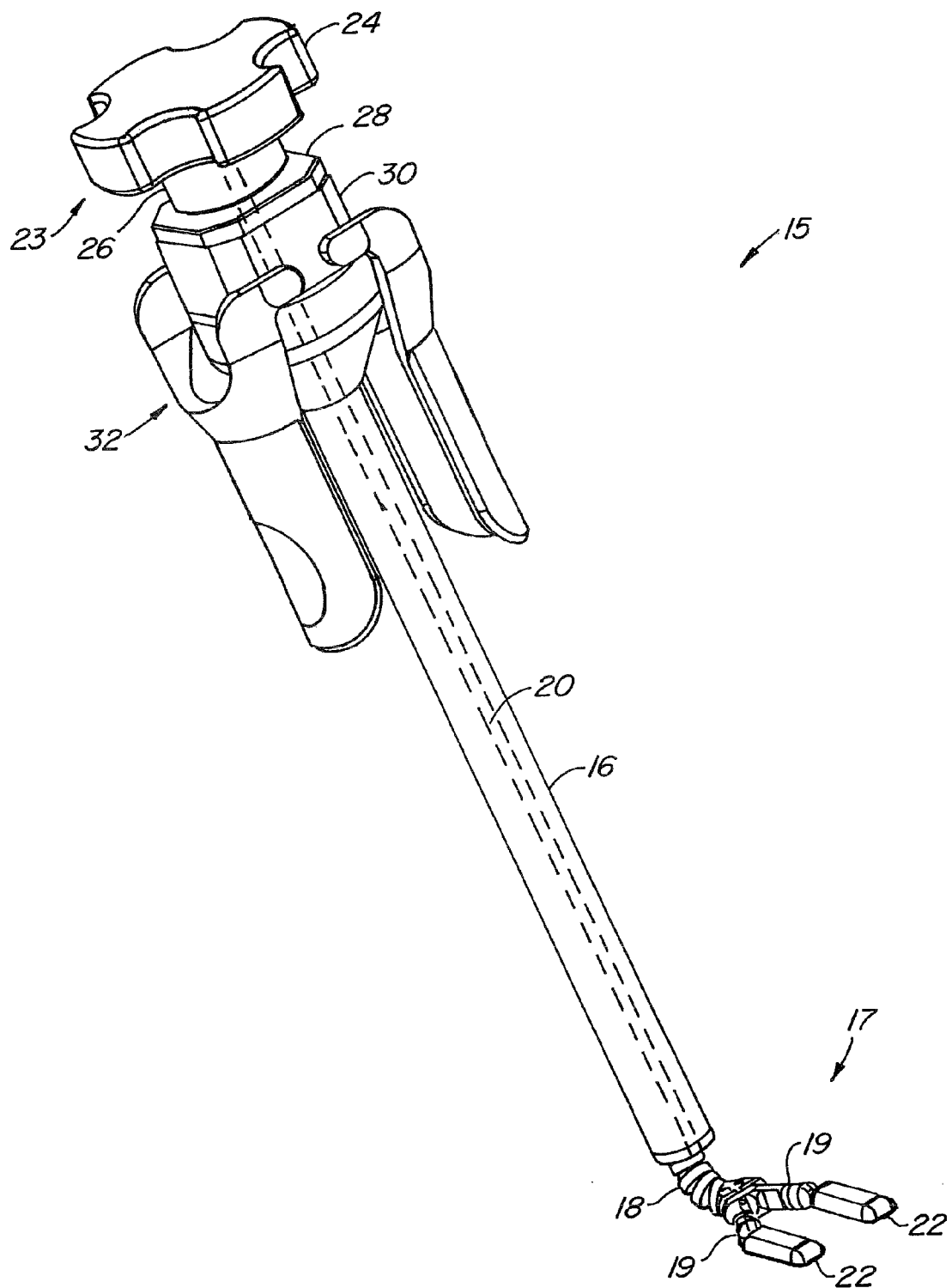
FIG. 23 is a perspective view of a first additional embodiment of the stabilizer.

FIG. 23 illustrates a first additional embodiment of the stabilizer. FIG. 23 provides a perspective over-all view of the stabilizer 15, which includes the elongate shaft 16 and stabilizer distal portion or foot 17. Again, the foot 17 comprises the jointed portion or ankle 18 connected with the pair of stabilizer bodies or toe portions 19. Also, the toe portions 19 are actuated and locked in a selected deployment position by the tension cable 20. Each toe 19 in turn mounts on of a pair of stabilizing surface or tissue engaging members 22, 22.

In this embodiment, the stabilizer 15 includes an adjustable cable tensioner 23, which comprises an internally threaded manual knob 24 engaging an externally threaded proximal cable junction 26. The knob 24 bears on a thrust bearing 28 which is mounted to the base of a proximal shaft housing 30. The cable 20 may be adjustably tensioned by turning the knob 24 to retract cable 20 until a selected tension is reached. A quick-release mechanism 32 is included in the proximal shaft housing 30 to permit toe 19 positioning. The cable 20 may be quickly loosened from a pre-set tension so that the toe 19 is moveable and positionable. The cable 20 may then be re-tensioned to substantially the same pre-set tension without turning knob 24 so that the toe 19 is again fixed in place. The details of this quick-release mechanism 32 will be described later in relation to FIGS. 28A-28B.

Figure 24:
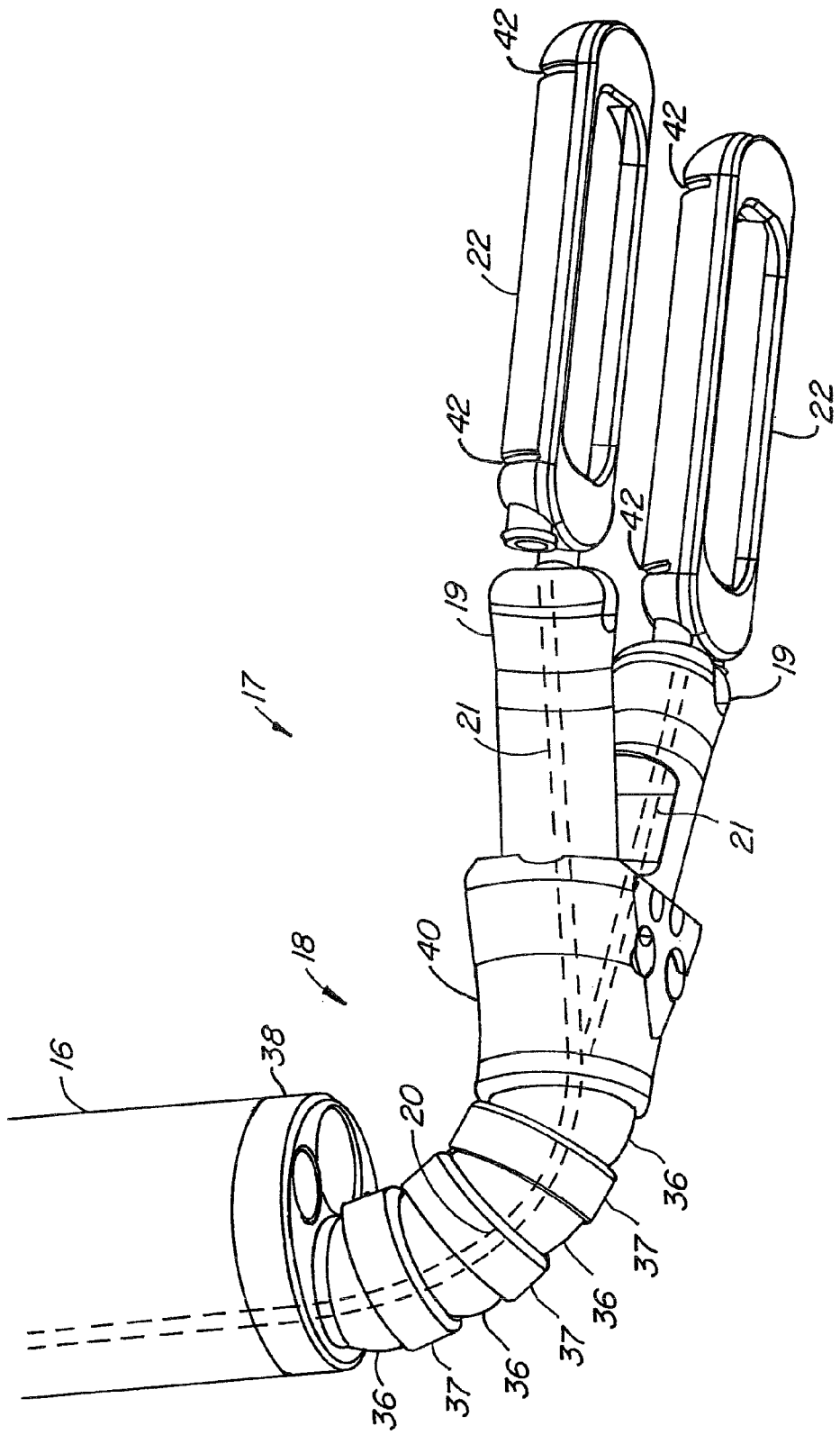
FIG. 24 is a detailed elevation view of the stabilizer foot of the first additional embodiment.

FIG. 24 is a detailed view of the stabilizer foot 17 and distal portion of shaft 16, showing the structure of the ankle 18 in this embodiment. Here, the ankle 18 comprises one or more (preferably about 3-4) sets of balls 36 engaged in intermediate socket rings 37. The most proximal ball 36 engages shaft end cap 38 and the most distal ball engaging toe mount housing

40. The balls 36 each have a hollow core through which extends the distal portion of tension cable 20. The cable 20 is bifurcated into connector cables 21, which extend through toe housing 40 to couple with the toes 19. Note that the stabilizing surfaces 22 preferably each include a pair of grooves or cleats 42 for releasably securing flexible members 502 during surgery.

Figure 25:
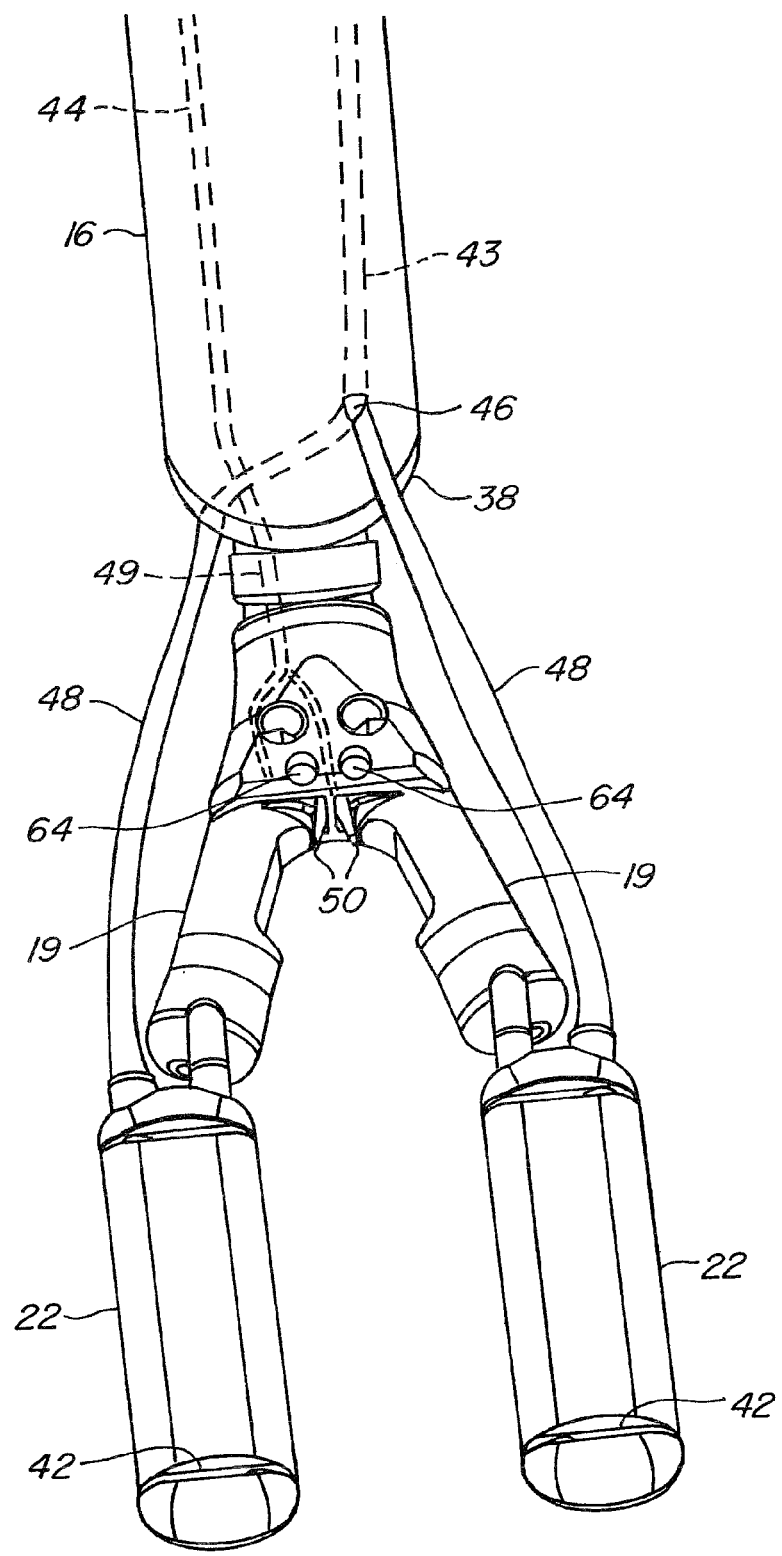
FIG. 25 is a detailed plan view of the stabilizer foot of the first additional embodiment.

FIG. 25 provides a detailed view of the stabilizer foot 17. In this example, a single vacuum source tube 43 extends through shaft 16 to a vacuum plenum 46 in shaft distal end cap 38. The plenum 46 communicates with a pair of vacuum conduits 48 which connect to the stabilizing surfaces 22. The conduits 48 may be composed of a flexible polymer, optionally with internal stiffening coils to resist collapse. Alternatively, individual vacuum source tubes may be provided for each stabilizer surface 22, and alternative embodiments may have entirely internal vacuum source routing.

Also shown in this example is an irrigation fluid supply tube 44 which extends through shaft 16 to communication with a irrigation conduit 49, which connects to irrigation nozzles 50. In this example, the conduit 49 is internal, connecting to the nozzles 50 in the center of toe housing 40. Alternatively, one or more irrigation nozzles 50 may be provided in stabilizing surfaces 22, and the conduit 49 may communicate externally in the manner of vacuum conduits 48.

Figure 26:
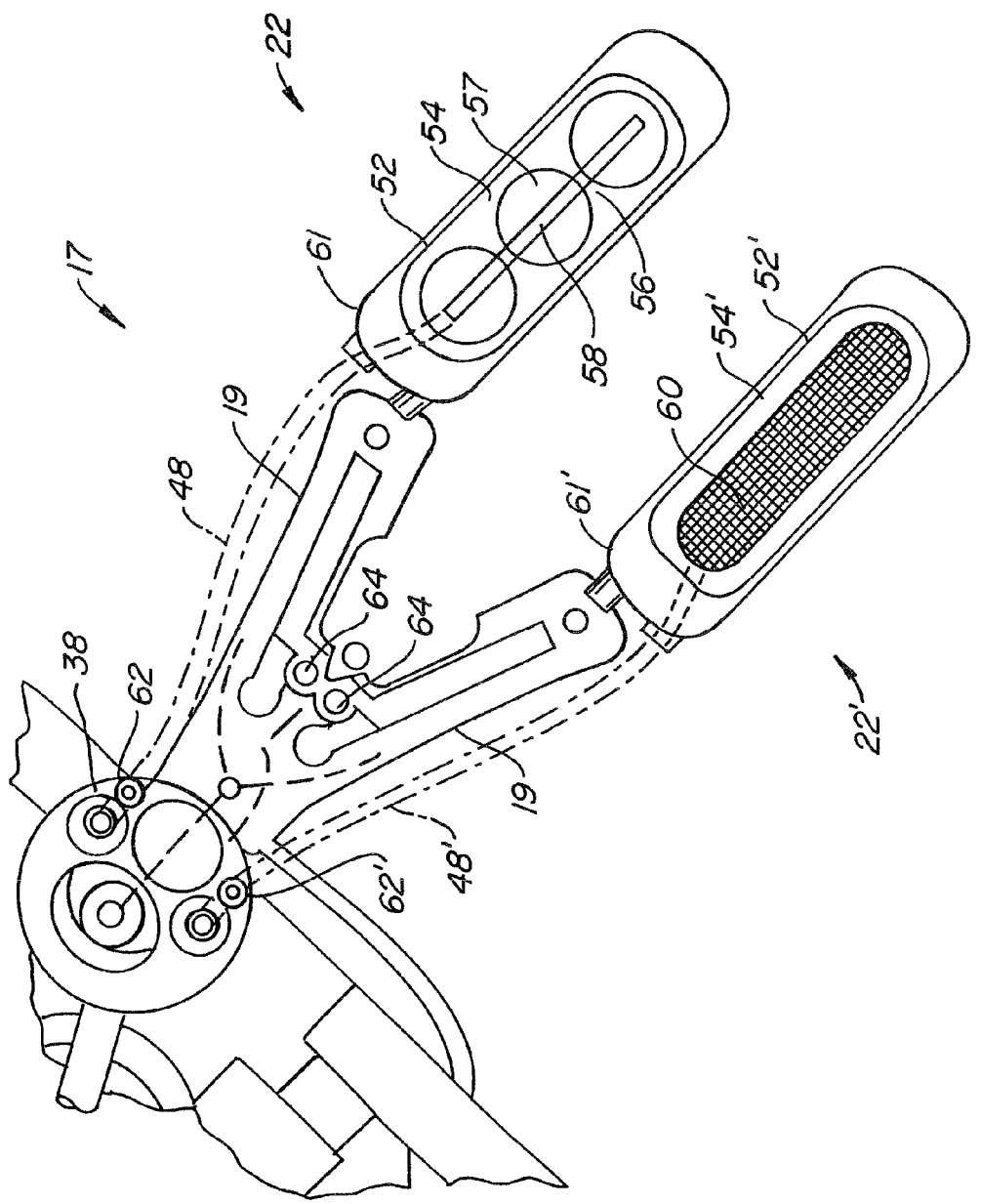
FIG. 26 is a detailed view of the underside of the stabilizer foot of FIG. 25.

FIG. 26 is a view of the underside of foot 17 in the embodiment shown in FIG. 25. FIG. 26 shows suction pads 52, 52' mounted to the undersides of stabilizing surfaces 22, 22'. The pads include a mating perimeter 54 which engages the tissue surface of the beating heart, typically at the site of an anastomosis, and creates a bonding pressure to the tissue upon application of vacuum within pad 52, 52'.

As shown, various conformations of suction pads 52 are feasible. In this example, pad 52 includes subdividing webs 56 with divide the pad surface into a plurality of subpad areas or suckers 57. An interconnecting pad plenum 58 may be included to control pressure of one sucker relative to the adjacent, e.g., by metering holes which prevent loss on suction by one sucker 57 in the event of leakage in the adjacent sucker. Alternative pad 52' includes a grid 60 within the mating perimeter 54. The grid 60 controls tissue contact, and may provide a selected degree of friction with tissue.

In one preferred embodiment, pads 52, 52' are configured as disposable units, the pads 52, 52' being mounted to disposable sleeves 61, 61' including disposable conduits 48, 48'. The sleeves 61, 61' are mounted upon stabilizing surfaces 22, 22' (e.g., slipped over and held by friction) and connected to vacuum ports 62, 62' in shaft end cap 38 prior to surgery.

Figure 27A:
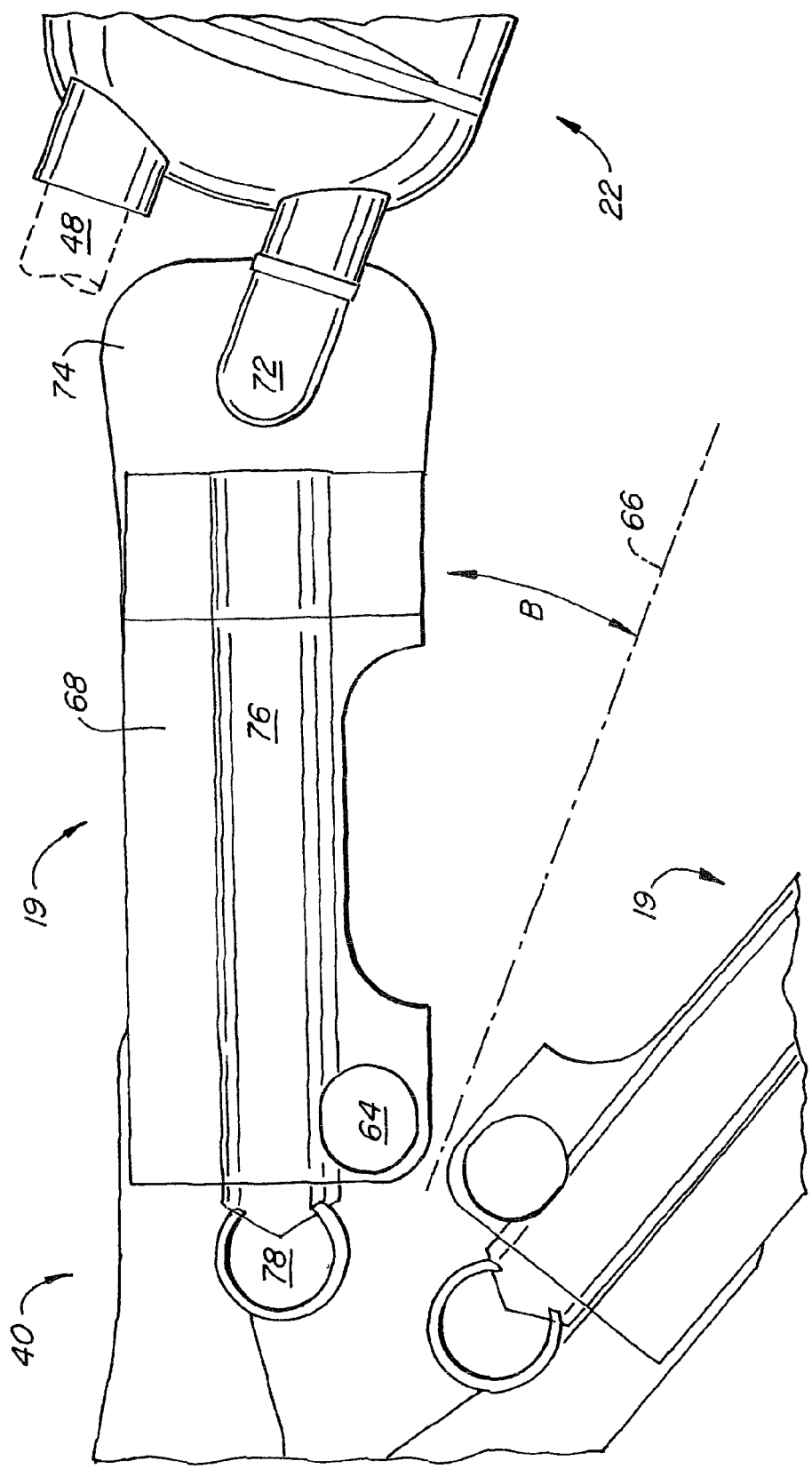
FIGS. 27A and 27B are section views of the ankle portion of the stabilizer foot showing the locking mechanism.
Figure 27B:
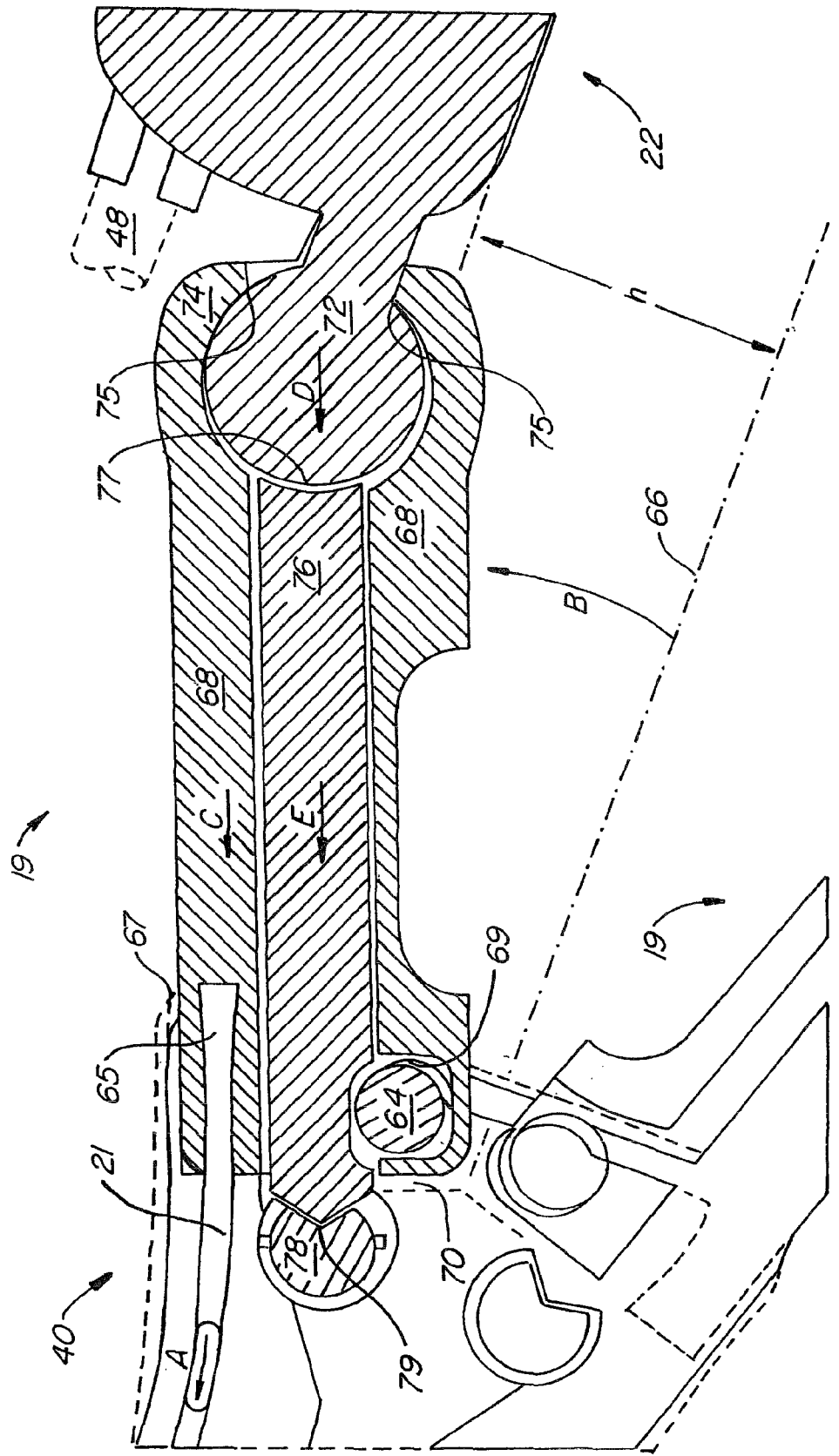

FIGS. 27A-27B illustrate bow the toes 19 are able to pivot and lock in place. FIG. 27A is an detail plan view of one toe 19 together with a portion of toe housing 40 and FIG. 27B is a longitudinal section view of the same subject. The toes 19 are pivotally joined to toe housing 40 by pivot pins 64, permitting rotation of the toes towards or away from foot centerline 66 to cycle between the stowed, furled toe position and the spread, deployed toe position as shown by Arrow B.

The toe spreading rotation is activated by tension on cable 21 as adjustably applied by the cable tensioner 23 and cable 20, previously shown in FIG. 23. Connector cable 21 (previously shown in FIG. 24) is fixed at cable distal end 65 to toe casing 68, as shown in FIG. 27B. The cable distal end 65 may be fixed by any suitable means, such as by swaging, splayed in soldered socket, set screw or the like. Such fixing occurs at a point outboard of pin 64 (farther from centerline 66). Tension on cable 21 thus tends to rotate toe casing 68 outwards in the direction shown by Arrow B until stabilizing surfaces 22 are offset from centerline 66 by a selected offset h. Outward rotation of toe 19 is limited to a selected angle by mechanical stop, such as contact with toe housing 40 at area 67.

Following toe rotation, the action of cable 21 acts to frictionally lock or adjustably brake toe 19 from further movement as follows: Pivot pin 64 engages casing 68 with a selected degree of longitudinal clearance or play as indicated by clearance spaces 69 and 70, thus permitting casing 68 to move slightly longitudinally in the direction shown by Arrow C as tension is applied to cable 21. This movement of casing 68 in turn pulls on stabilizer mounting ball 72 which mounts stabilizing surface 22 by engagement of toe socket 74. Contact of ball 72 with socket 74 at distal contact area 75 in turn causes movement of ball 70 in the direction of Arrow D. Ball 72 in turn impinges upon the distal end of push-rod 76 at contact area 77, moving push-rod 76 along the toe axis in the direction shown by Arrow E. The push-rod 76 in turn contacts rod seating pin 78 at contact point 79, preventing further movement of rod 78. The clearances at spaces 69, 70, 75, 77 and 79 are selected so that when the cable 21 is tensioned to a selected locking tension, the frictional forces at these contact areas is substantial and acts as a locking break to effectively resist and prevent rotational motion of ball 72 in ball housing 74 during the conduct of surgery. Optionally, surface 77 of pin 76 may be provided with an abrasive coating or pattern to increase friction (e.g., bonded diamond dust).

Note that the tension of cable 20 is also passed via the forces on toe housing 40 to the one or more ball joints 36, 37, creating a lock or braking friction in these joints at the same time that the stabilizing surface joint 72, 74 is locked.

Preferably at a reduced or intermediate tension of cable 21, the friction at contacts 75 and 77 is sufficient to partially resist rotation or adjustably brake ball 72, to permit stabilizer surface 22 to by "manually" rotated within socket 74 for controlled adjustment of surfaces 22 to target tissues, such as by action of robotic end effectors operating within a body cavity. Optionally, the degrees of freedom and range of motion of ball and socket joint 72, 74 may be selectively enabled and limited by suitable slots and limit pins in socket 74 and ball 72.

Figure 28A:
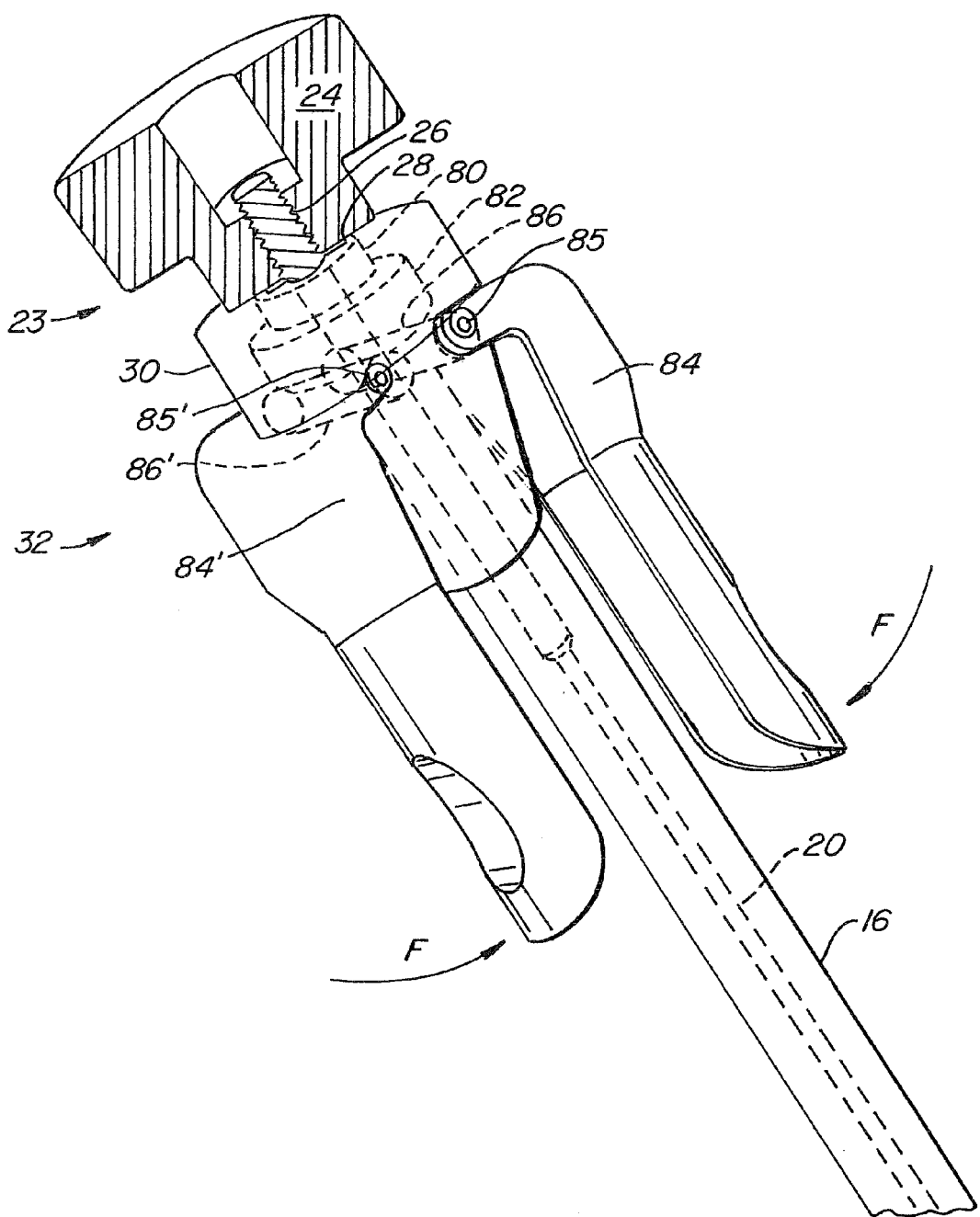
FIGS. 28A and 28B are section views of the external handle or base portion of the stabilizer showing the quick-release mechanism in the fixed and released positions respectively.
Figure 28B:
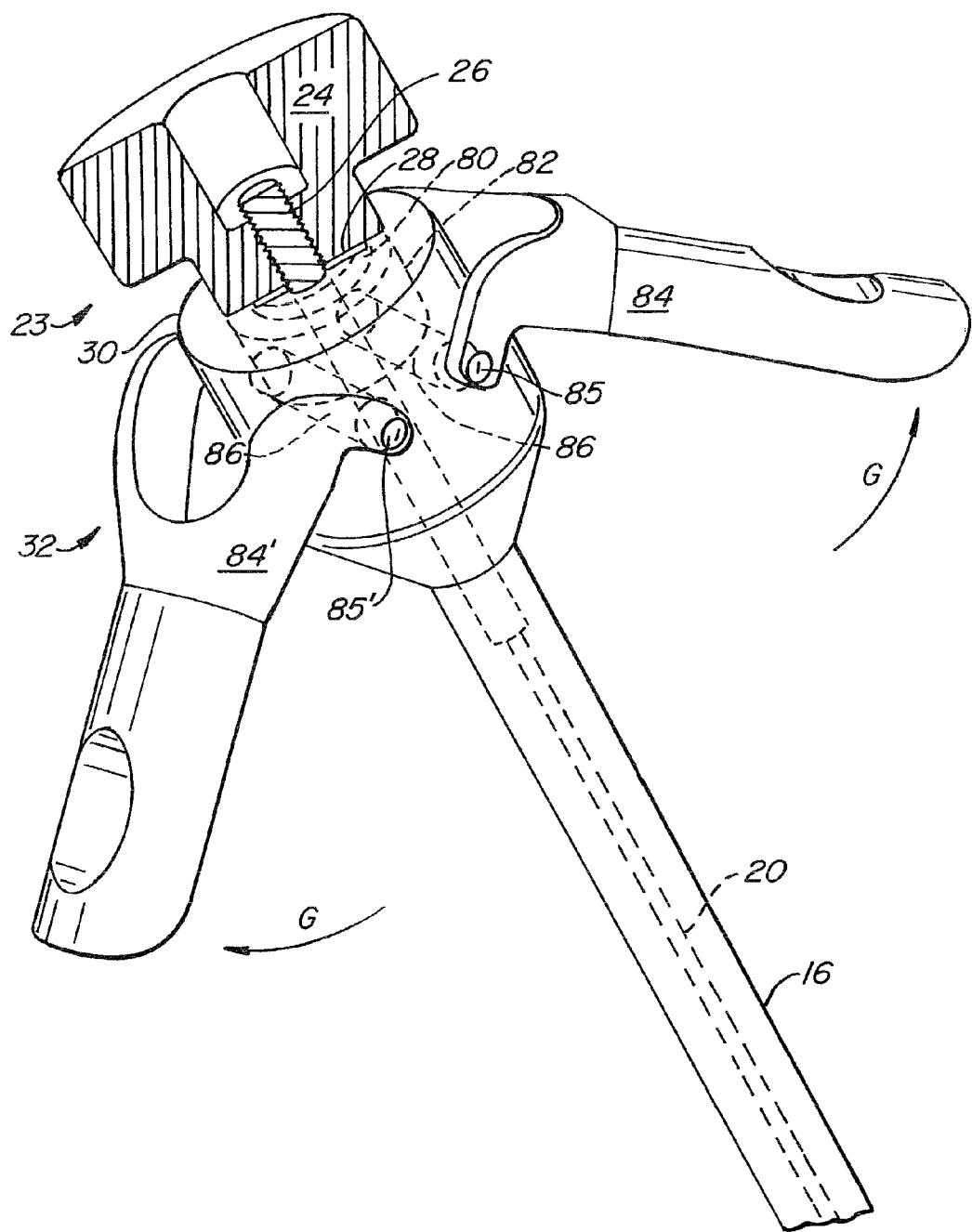

FIGS. 28A-28B are section views of the external or base portion of the stabilizer 15 showing the quick-release mechanism 32 in the fixed and released positions respectively. Note in FIG. 28A that the adjustable cable tensioner 23 may be preadjusted to a selected tension of cable 20, as described above, so that the knob 24 bears on thrust bearing 28. In this example, thrust bearing 28 is seated on bearing plate 80 in proximal shaft housing 30. The bearing plate 80 is in turn supported by release plate 82. An opposed pair of release handles 84, 84' are mounted to the sides of housing 30 by rigid connections to axles 85, 85' which are in turn pivoted to the sides of housing 30. The axles 85, 85' are re rigidly connected to internal release cams 86, 86' within housing 30. In the example shown, each of release cams 86 comprises a round section eccentrically mounted to axle 85, so as to have an angularly-variable cam-like profile relative to the axle 85. The cam profile of the release cam 86 is configured to contact and support release plate 82 when the handle 84 is moved to the closed position as shown by Arrow F in FIG. 28A, i.e., the surface portion of cam 86 in contact with plate 82 is at or near the maximum or high point of the cam profile when the levers are closed. The cam-supported release plate 82 in turn rigidly supports bearing plate 80 to maintain cable tension.

As shown in FIG. 28B, when the handles 84',84' are moved to the open position as shown by Arrow G, the release cams 86, 86' are rotated, and the cam profile is configured to contact the plate 82 at or near a low point of the profile when the handles 84 are in the open position. Both the bearing plate 80 and the release plate 82 are axially movably mounted in housing 30, so that as the release plate tends to move downward in response to cable tension, thus releasing the cable tension without requiring any adjustment of knob 24. The cable may be returned to the original tension by returning the handles 84',84' to the closed as shown by Arrow F in FIG. 28A. The mechanical advantage of cams 86 relative to handles 84 may be selected to provide a predetermined motion of plate 82 as the handles are moved.

Optionally the cam 86 may be slightly over-center when the levers are closed to be stabilize the closed position. The handles 84 and/or cams 86 may also be spring biased or balanced to be stable closed or bi-stable in both open and closed positions and may be inter-geared to operate symmetrically. Optionally, compression adjusters, such as spring washers and the like, may be placed between plates 80 and 82 to limit or control the cable tension. Alternative levers with mechanical advantage may be used in substitution for release cams 86.

In one embodiment, the cam profile is selected so that, when knob 24 is adjusted to lock the motion of foot 17 as described above, the release of tension when the handles 84 are then moved to the open position (Arrow G), leaves a selected degree of residual cable tension, maintaining toe outward position (Arrow B as shown in FIGS. 27A-27B), and permitting controlled, partially-braked motion of surfaces 22 and joints 36/37. Thus, in the released position, the surgeon or assistant may conveniently adjust the surfaces 22 to mate with the target tissue, e.g., by the use of robotic surgical end effectors, and then re-lock the foot 17 precisely and quickly by closing levers 84.

Figure 29:
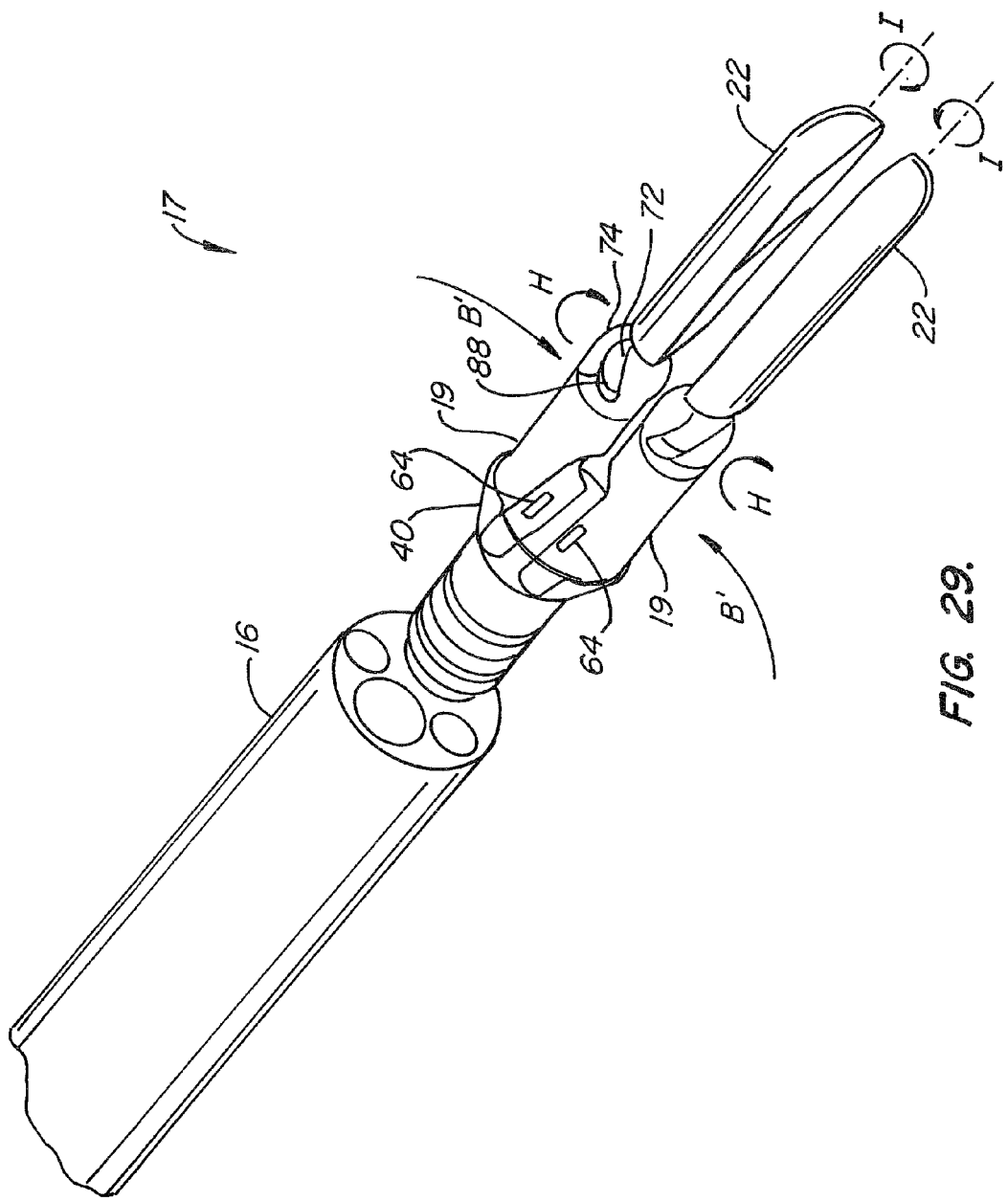
FIG. 29 is a detailed view of the stabilizer foot as rotated to the furled position to facilitate insertion or retraction.

FIG. 29 is a detailed view of the stabilizer foot 17 as rotated to the stowed or furled configuration to facilitate insertion or retraction. In surgical use, the stabilizer is typically inserted through a narrow cannula (not shown) passing through an incision in the patient's body wall. The compact stowed configuration permits the foot to fit in a narrow cannula. After loosening cable tension by action of the cable tensioner 23, the toes 19 may be rotated inward as shown by Arrows B'. Each stabilizing surface 22 may be aligned with the axis of shaft 16 by transversing motion of the ball-socket joint 72,74 along slot 88 as shown by Arrow H. Finally, each of the stabilizing surfaces 22 may be rotated about its own axis as shown by Arrows I to lie assembled facing one another, the assembled stabilizing surface profile preferably approximating a rounded overall shape. Thus aligned, the foot may be inserted into and along the cannula until the foot 17 extends into the body cavity adjacent the surgical site.

Note that the contours of the toe housing 40, toes 19 and surfaces 22 are preferably generally smooth and rounded, facilitating automatic alignment of these elements with the cannula opening as the foot 17 is retracted. In addition, these foot elements may be manipulated by the surgeon or assistant to assist retraction, e.g., by use of the end effectors of a surgical robotic system.

Additional Embodiment #2

Figure 30:
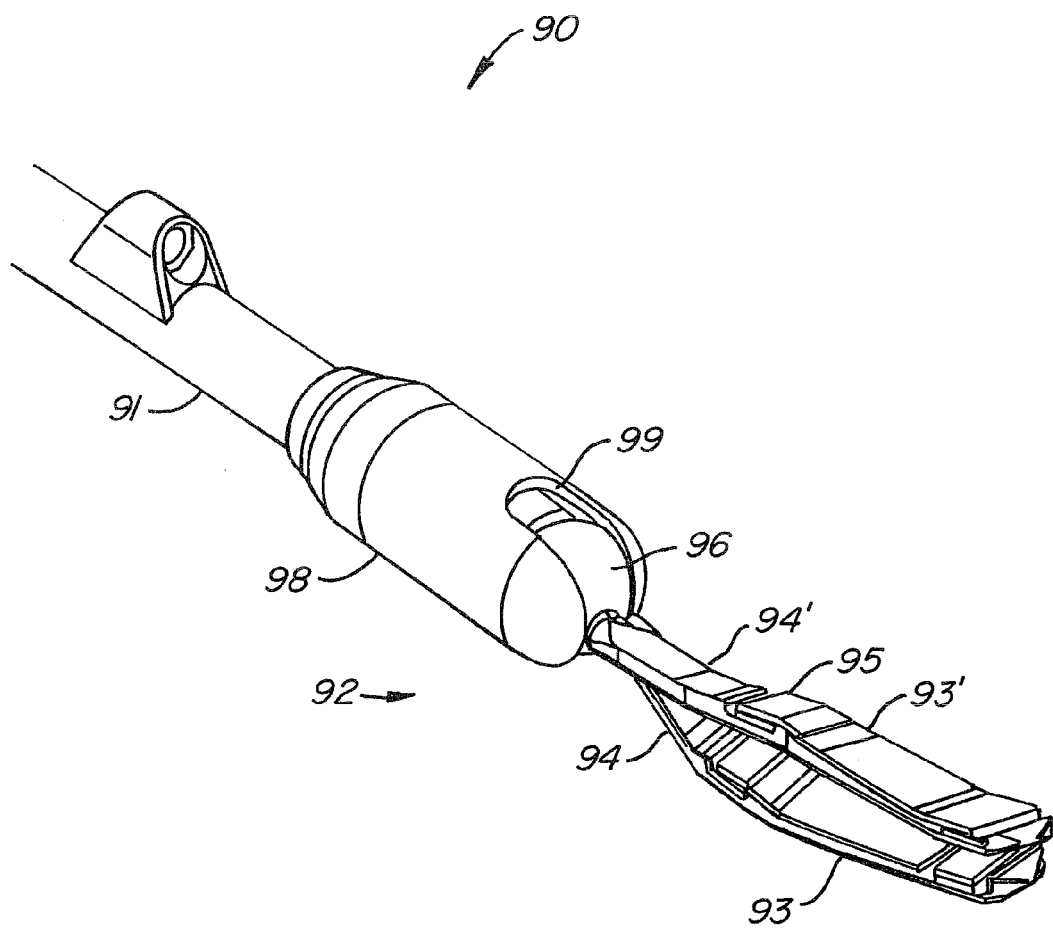
FIG. 30 is a perspective view of the foot portion of a second additional embodiment of the stabilizer, showing the stabilizer toe portions rotated by the split ball mounting to the furled position.
Figure 31:
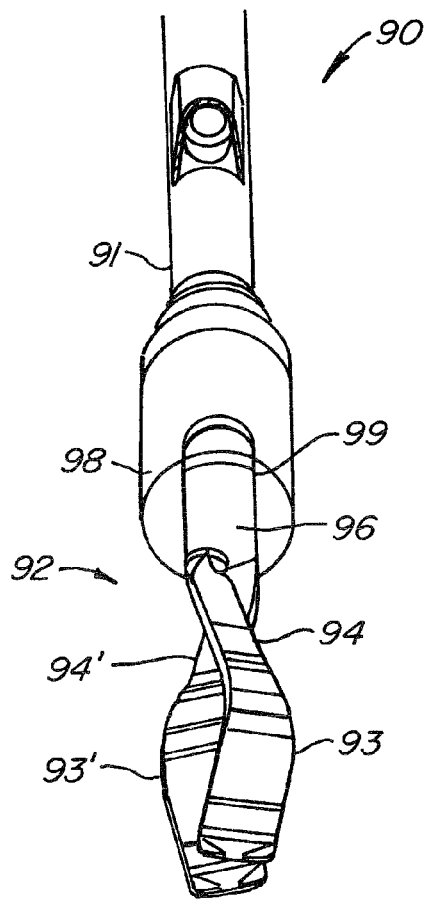
FIG. 31 is a top view of the stabilizer of FIG. 30 showing the furled toe portions superimposed on the stabilizer shaft, illustrating the compact cross-sectional configuration of the furled stabilizer.
Figure 32:
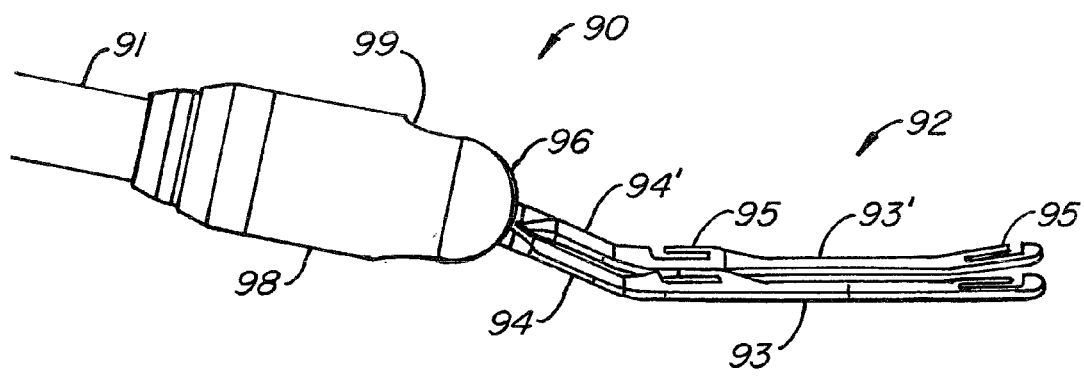
FIG. 32 is a side view of the foot portion of the stabilizer of FIG. 30 also showing the toe portions in the furled position.

FIG. 30 illustrates a second additional embodiment of the stabilizer. FIG. 30 is a perspective view showing the distal end of shaft 91 of the stabilizer 90. An attached foot portion 92 is comprised of stabilizing surfaces 93, 93' which are supported by toe portions 94, 94', respectively. The toe portions 94, 94' are joined by a split ball mounting 96 which functions in a manner similar to the spherical split ball shell 1041, 1048 previously described. The split ball mounting 96 allows the toe portions 94, 94' to rotate from the furled or stowed configuration to an open or deployed configuration. The shaft 91 rigidly connects to a joint socket housing 98 which encloses and mounts split ball 96 at its distal end. FIG. 31 is a top view of the stabilizer 90 distal end and FIG. 32 is a side view of the stabilizer 90 distal end.

Figure 33:
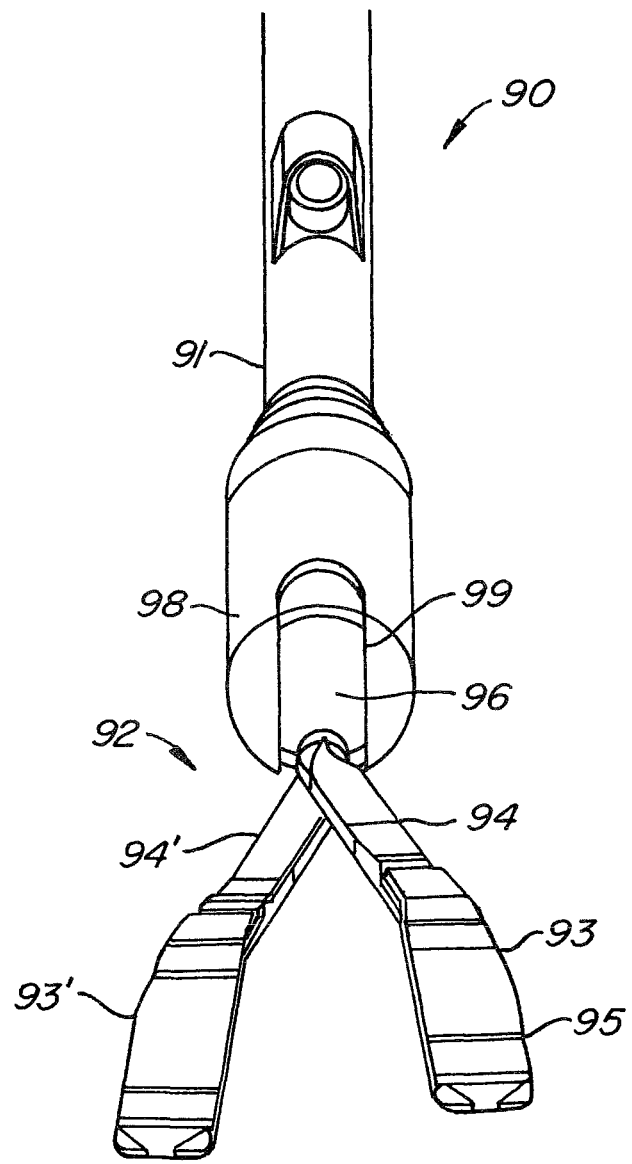
FIG. 33 is a top view of the foot portion of the stabilizer of FIG. 30 showing the stabilizer toe portions in the deployed position.

FIG. 33 shows stabilizer 90 with the toe portions 94, 94' and the stabilizing surfaces 93, 93' rotated outwards by the split ball mounting 96 to the deployed configuration. The split ball mounting 96 and toe portions 94, 94' may be transversed along slot 99 to move the stabilizing surfaces 93, 93' collectively to positions at an angle to the shaft axis. Note the plurality of pocket-grooved cleats 95 on surfaces 93 for holding flexible members such as Silastic tubing and suture material.

Figure 34:
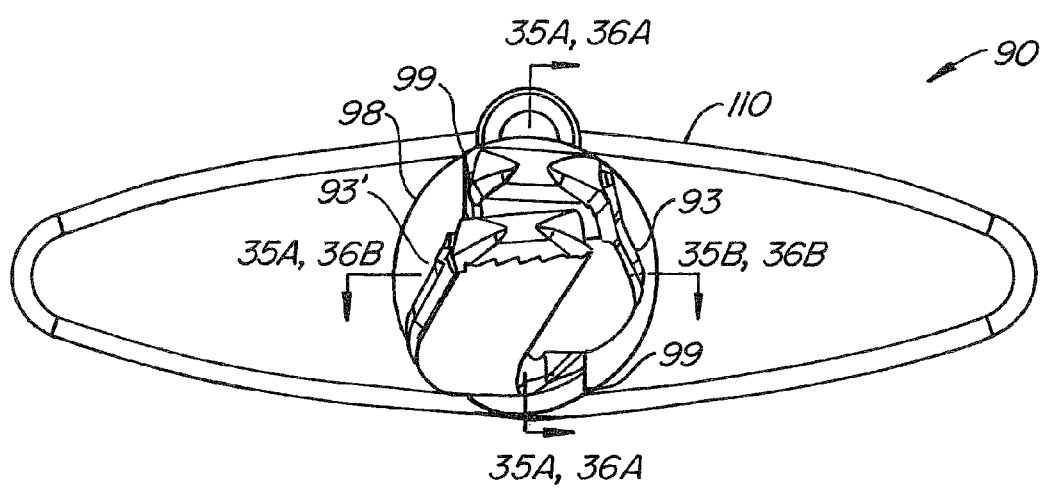
FIG. 34 is a frontal elevation view of the stabilizing surfaces nested in an overlapping configuration within the overall diameter of the joint housing 98.

FIG. 34 is a frontal elevation view of the stabilizing surfaces 93, 93' nested in an overlapping configuration within the overall diameter of the joint housing 98. FIGS. 35A and 35B are side and plan longitudinal cross-sectional views of the split ball joint 96 of the stabilizer and socket housing 98. FIG. 35A is a section along Line 35A-35A as shown in FIG. 34 (generally along slot 99), and FIG. 35B is a section along Line 35B-35B as shown in FIG. 34 (generally perpendicular to slot 99). Note that the split ball joint 96 comprises a right and left generally hemispherical ball sides 101 and 101', assembled movably together in contact along ball junction 106 to form collectively a generally spherical body which is housed and movably contained between inner socket member 103 and outer socket member 104. Ball side 101 mounts toe 94 and ball side 101' mounts toe 94'. Inner socket member 103 and outer socket member 104 are fixedly mounted to socket housing 98 which is in turn mounted to shaft 91.

The respective ball sides 101, 101' may be move in concert (without relative motion between ball halves) or may be moved independently. The ball halves 101, 101' may be rotated within the socket 103/104 axially, i.e., along the axis of the respective toe 94. The ball halves 101, 101' may also be moved transversely, i.e., to swing laterally to follow slot 99 or alternatively to move perpendicular to slot 99 within the clearance of the slot width. Note that in FIG. 35B, the toes 94, 94' have been traversed along slot 99 until the ball junction 106 lies generally perpendicular to the axis of shaft 91.

Pushrod 108 extends through the hollow center of shaft 91 and may be driven (see FIGS. 36A-36B) in the direction of Arrow J to frictionally impinge upon the adjacent ball halves at distal contact surface 109, causing the ball joint 96 to be frictionally locked or braked. Note that when the pushrod 108 contact is with only one ball half, as in FIG. 35B, friction is still induced by pressure at ball junction 106, and at contact with outer socket 104. Thus both balls 101, and 101' are braked or locked.

Figure 36A:
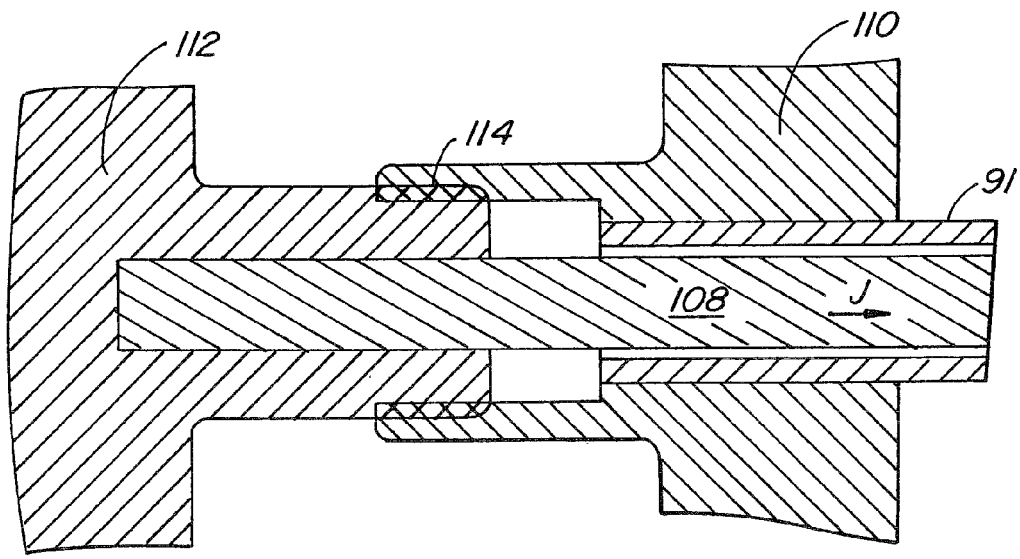
FIGS. 36A and 36B are longitudinal cross-sectional views of the push rod compression mechanism of the stabilizer, showing the handle or base from the side and top respectively.
Figure 36B:
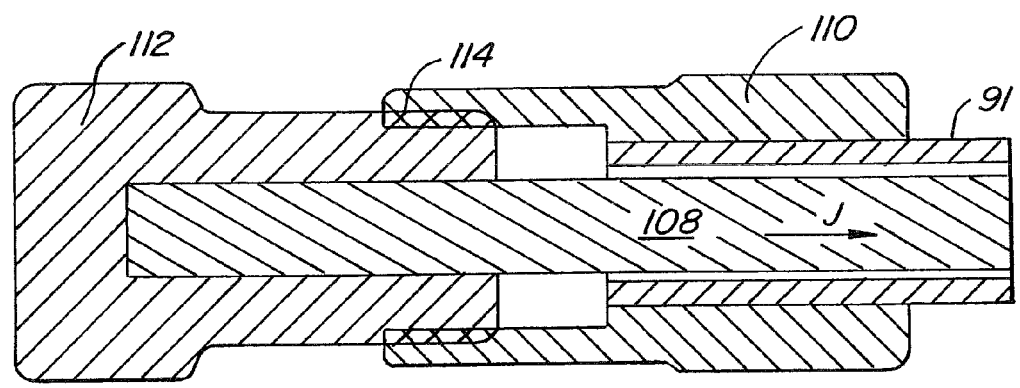

FIGS. 36A-36B are longitudinal cross-sectional views of the push rod compression mechanism of the stabilizer, showing the handle or base 110 from the side and top respectively, corresponding to the sections of Line 36A-36A and Line 36B-36B respectively as shown in FIG. 34. Base or handle 110 is rigidly mounted to hollow shaft 91. The pushrod 108 extends outward beyond handle 110 to fixedly mount to knob 112. Knob 112 is in threaded engagement with handle 110, and thus as knob 112 is screwed inward into handle 110, pushrod 108 is driven in the direction of Arrow J.

Additional Embodiment #3

Figure 37:
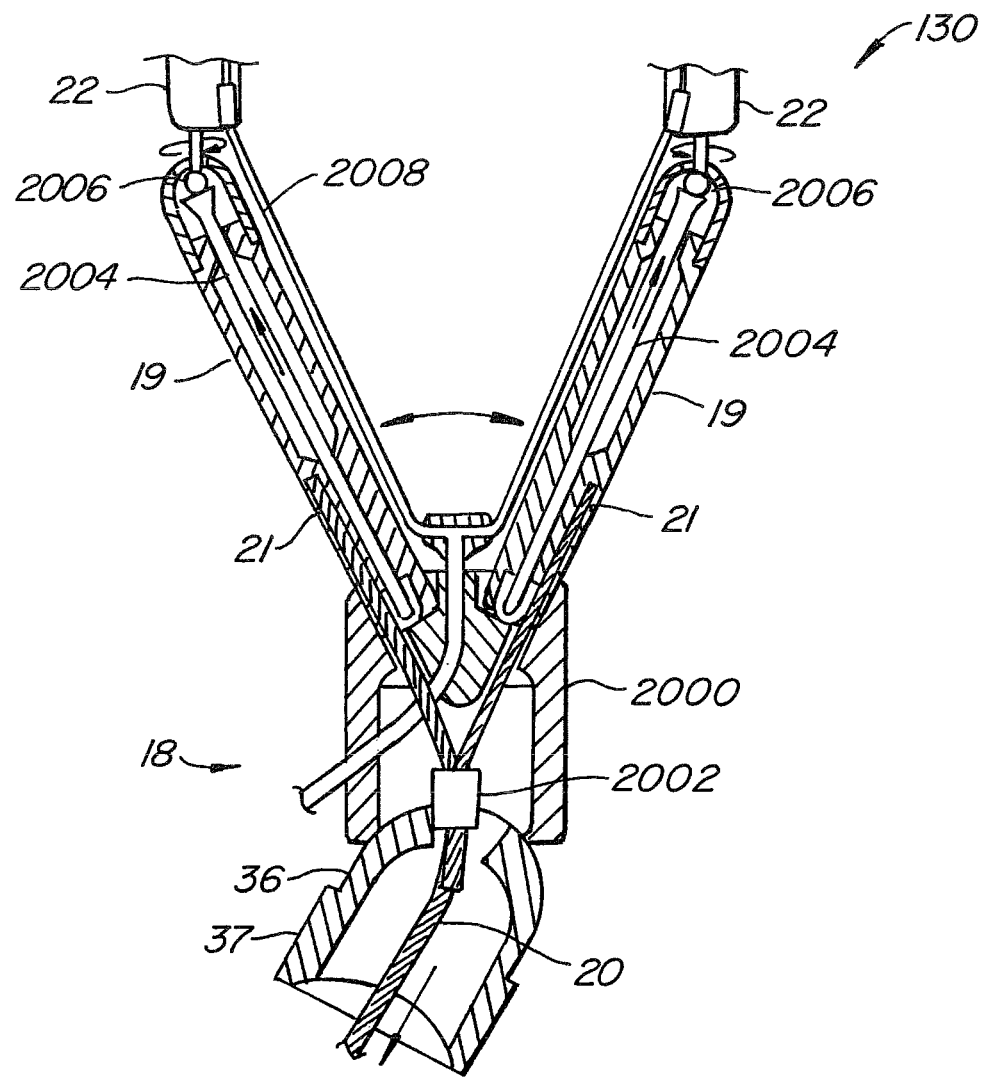
FIG. 37 is a section plan view of a third additional embodiment of a stabilizer comprising a ball-joint ankle portion and tension-cable-actuated lockable toe portions.

FIG. 37 is a section plan view of an additional embodiment of a foot 130 of the stabilizer. As shown in this embodiment, the foot 130 comprises an ankle 18 and toes 19. The ankle 18 comprises a series of balls 36 and intermediate socket rings 37, of which only one is shown, connected with a housing 2000. Seals 2002 may be present between the balls 36 and socket rings 37 and between the ball 36 and housing 2000. The cable 20 enters the housing 2000 and connects with the toes 19 by connector cables 21. The cable 20 and connector cables 21 are joined with a cable crimp 2002. A push rod 2004 is disposed within each toe 19 and is engageable with a diamond dust ball link 2006. Each link 2006 is attached to a stabilizing surface or tissue engaging member 22. In addition, a vacuum or irrigation line 2008 is disposed within each toe 19 as shown. The principles of function and construction are generally similar to the Additional Embodiment #1.

Additional Embodiment #4

Figure 38A:
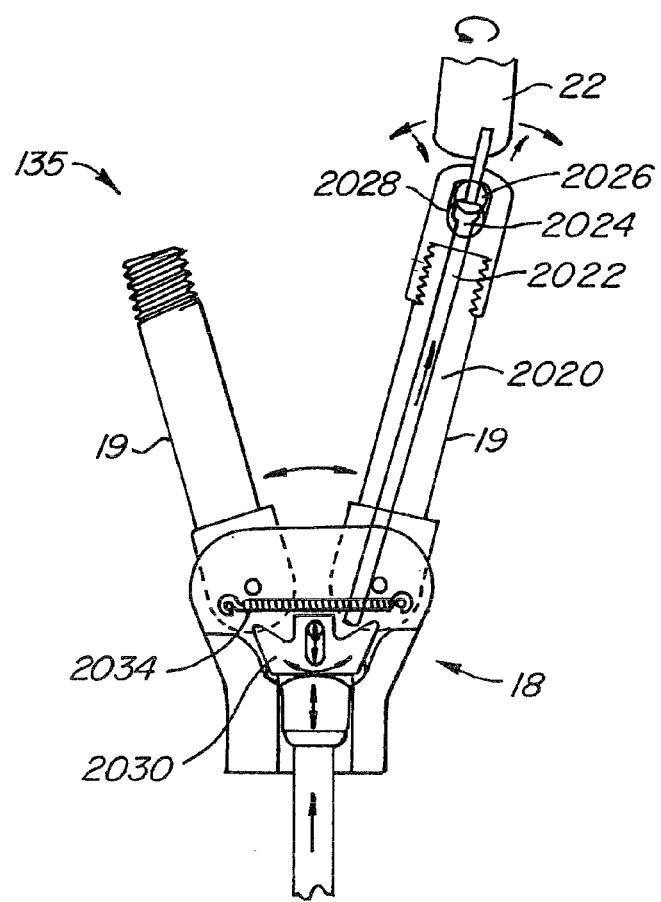
FIGS. 38A-38B are a section plan view and elevation of a fourth additional embodiment of a stabilizer comprising a ball-joint ankle portion and pushrod-actuated lockable toe portions.
Figure 38B:
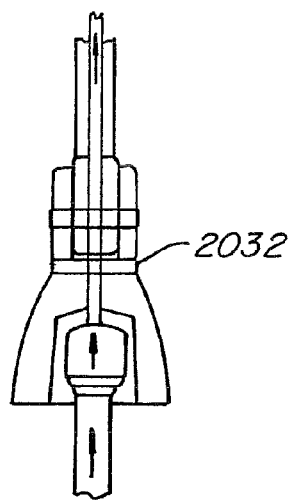

FIG. 38A is a section plan view of an additional embodiment of a foot 135 of the stabilizer. As shown in this embodiment, the foot 135 comprises an ankle 18 and toes 19. Each toe 19 is comprised of a tension tube 2020 which holds a push rod 2022. Each push rod 2022 has a cup-shaped end 2024. The cup-shaped end 2024 is mated with a ball link 2026, which is typically diamond dust coated or polished, by way of an installation hole 2028 to form a ball-and-socket joint. The ball link 2026 is connected to a stabilizing surface or tissue engaging member 22. Opposite the cup-shaped end 2024, each push rod 2022 is joined with the ankle 18. Within the ankle 18, a cam 2030 actuates the push rods 2022. The cam 2030 floats about a float pin 2032, as illustrated in FIG. 38B. In addition, the ankle 18 comprises an over-center spring 2034 as shown. In this example, the toes 10 are lockable by pushrod-actuation, wherein shaft mounted pushrod assembly 2036 bears on cam 2030.

Additional Embodiment #5

Figure 39A:
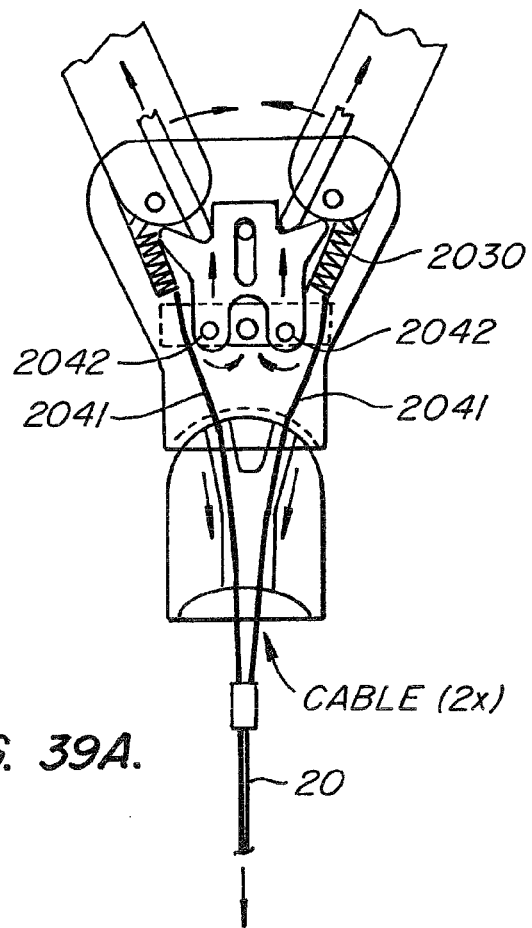
FIGS. 39A-39B are a section plan view and elevation of a fifth additional embodiment of a stabilizer comprising a ball-joint ankle portion and tension-cable/cam or gear-actuated lockable toe portions.
Figure 39B:
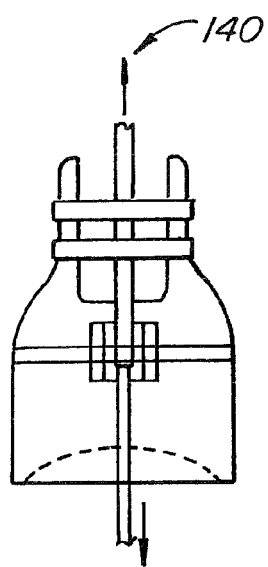

FIG. 39A is a section plan view and FIG. 39B is an elevation of an alternative embodiment 140 of a stabilizer including aspects of the invention. In this example the stabilizer comprises a ball-joint ankle portion and tension-cable/cam or gear-actuated lockable toe portions. Embodiment 120 is generally similar to embodiment 135 of FIG. 38A-38B, except that cam 2030 is activated by a pair of subcams 2042, which are in turn actuated by cable 2043 and cable 2044. The cable actuation provides flexibility as neck portion 2046 is rotatably adjusted.

Additional Embodiment #6

Figure 40:
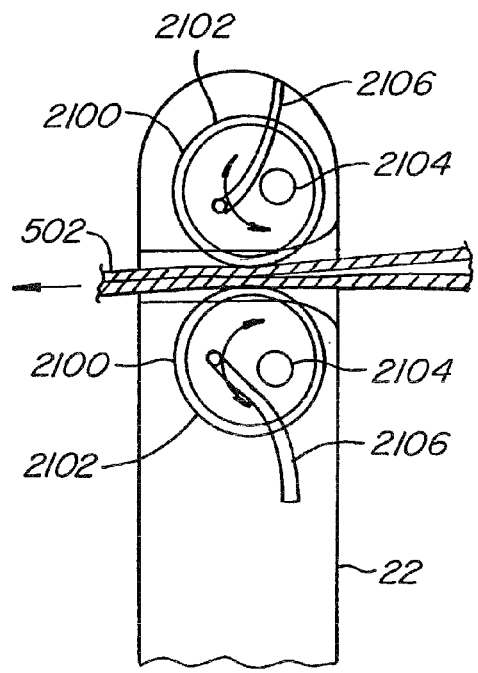
FIG. 40 and FIG. 40A are sixth additional embodiments illustrating stabilizer toe cleats.

As previously described, to prepare the coronary artery CA for anastomosis, the coronary artery CA is isolated from blood flow by cinching the coronary artery CA upstream and downstream of the desired location for anastomosis. Thus, when the anastomosis is made, blood will not flow out into the workspace. The coronary artery CA may be isolated by any known or suitable method. In some embodiments of the present invention, the coronary artery CA is to be isolated with the use of flexible members 502 which are held by the tissue engaging member 22 rather than by vessel occlusion fasteners or fastening clips 350. FIG. 40 provides an embodiment of a tissue engaging member 22 having a flexible member 502 removably attached thereto. In this embodiment, two discs 2100 are mounted on the tissue engaging member 22. Each disc 2100 has a knurled perimeter 2102 and rotates eccentrically about a pivot pin 2104. The discs 2100 are spaced apart so that the flexible member 502 is pinched between the discs 2100 as the flexible member 502 is pulled in the direction of the arrow. As the member 502 is pulled, each disc 2100 rotates and impinges against a torsion spring 2106. This holds the flexible member 502 in place.

Figure 40A:
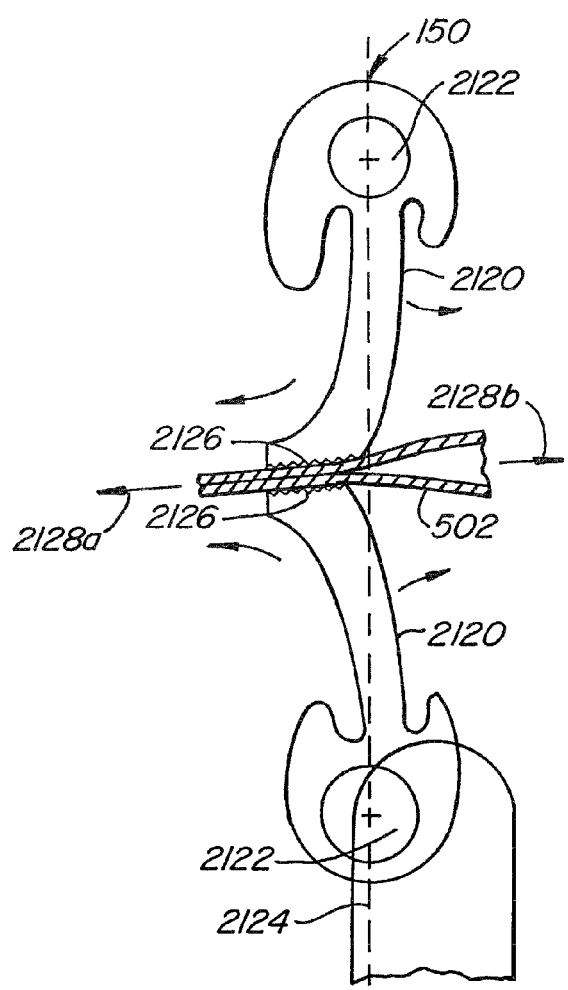

FIG. 40A shows an embodiment of a spring cleat 150 for holding a flexible member (e.g., silastic tubing) which operates on a "jam cleat" principle generally similar to the embodiment of FIG. 40. The spring cleat 150 includes a pair of leaf spring members 2120, each spring member 2120 being mounted at a fixed end to a corresponding spaced-apart pair of mounting elements 2122 so that the spring members 2120 lie adjacent and generally parallel to a mounting surface, such as the upper surface of a stabilizing member 22. The spring members 2120 may comprise, for example, a flexible plastic composition and the mounting element 2122 may include a rivet fixed to the stabilizer, so as to penetrate and clamp the leaf spring member 2120 at its fixed end. Alternatively, springs 2120 may be fixed to the mounting surface by bonding, ultrasonic welding, screws or other fixation means. The free ends of the spring members extend towards one another, and are arranged so as to provide a spring-to-spring contact zone 2126 when not holding a flexible member. The contact zone 2126 may be offset from the centerline 2124 passing between the pair of mounting elements 2122.

As a flexible member 502, such as silastic tube, is pulled in an insertion direction (Arrow 2128a) in the direction of the offset the spring members are urged apart, thus opening the contact zone 2126 to receive the flexible member 502, while maintaining a steady clamping pressure of the spring end on the member 502. The contact zone portion 2126 may have texture elements, such as serrations or teeth, to increase friction with the member 502. In the event that a tension force on the member 502 tends to pull the member 502 in the opposite direction from insertion (Arrow 2128b), the combination of friction and clamping force tends to cause the contact zone to close tighter, causing a "jam cleat" effect to greatly increase the force resisting further extraction. The member 502 may be removed by pulling in the insertion direction while pulling upwards (away from mounting surface) to slide the flexible member 502 out of the contact zone 2126. Alternatively, the spring members 2120 may be of a rigid composition, with conventional torsion springs being included in mounting elements 2122.

Additional Embodiment #7

Figure 41A:
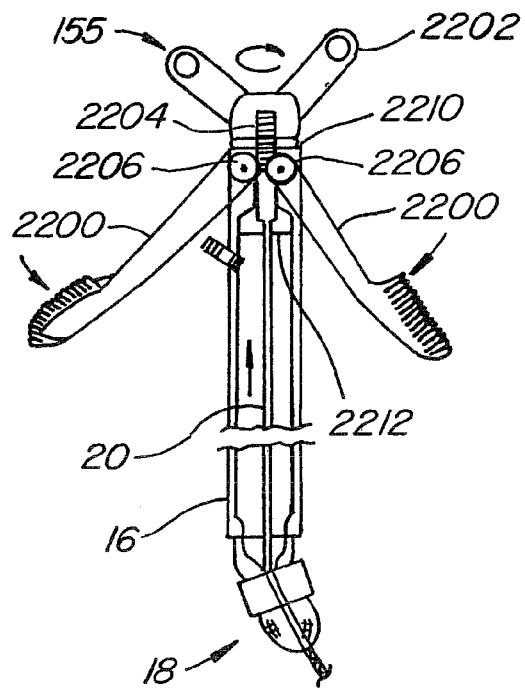
FIGS. 41A-41B are section elevation views of a seventh additional embodiment of a stabilizer comprising a quick-release and cable tensioning mechanism included in the handle, illustrated in the closed and released configurations.
Figure 41B:
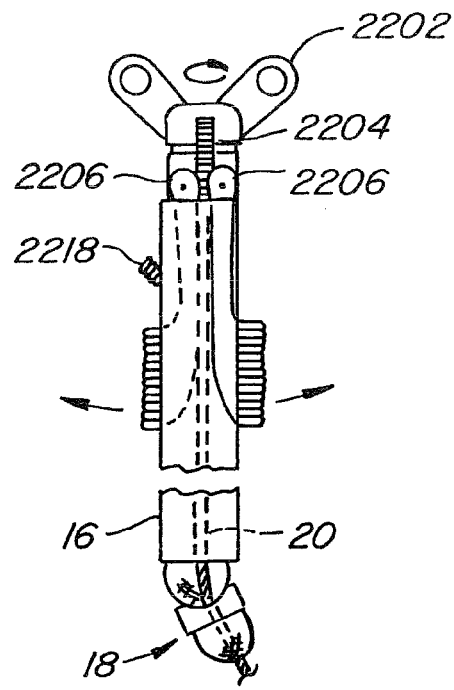

FIGS. 41A-41B illustrate an additional embodiment 155 of the stabilizer of the present invention. FIGS. 41A-41B illustrate how the toes 19 of the stabilizer are able to lock in place by movement of handles 2200. FIG. 41A illustrates the handles 2200 in an open position. As shown, the cable 20 is disposed within the shaft and ankle 18 and connects with the toes (not shown). The proximal end of the cable 20 is connected to a maximum lock control 2202 by a threaded cable coupler 2204. The handles 2200 are connected with the shaft 16 and cable 20 by eccentric rollers 2206. By moving the handles 2200 in the direction of the arrows in FIG. 41A, the cable 20 is tightened and the toes are locked in place. FIG. 41B illustrates the handles 2200 in the position wherein the toes are locked in place. By moving the handles 2200 in the direction of the arrows in FIG. 41B, the cable 20 is released and the toes are again free to move. This embodiment also includes a washer vacuum input 2208, a thrust 2210 and one or more seals 2212.

Additional Embodiment #8

Figure 42:
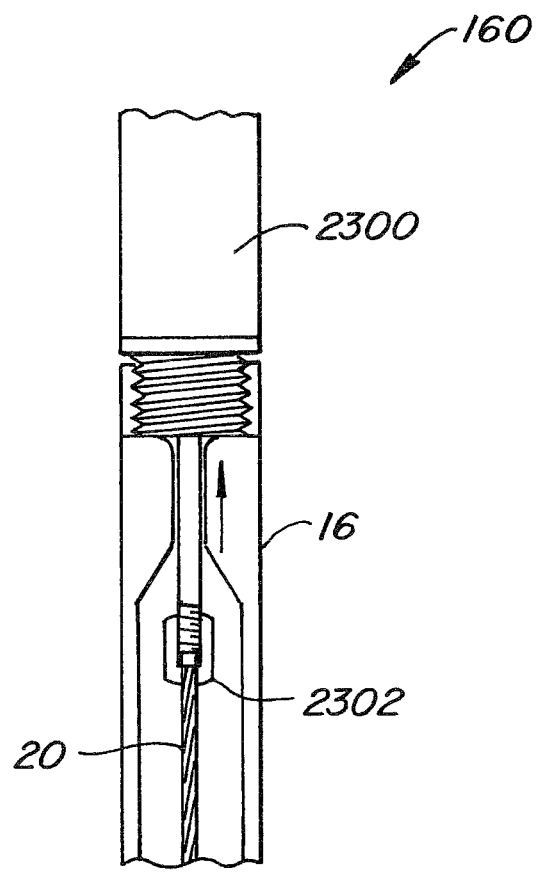
FIG. 42 is a section elevation view of an eighth additional embodiment illustrating an optional pneumatic cable tensioning mechanism.

FIG. 42 is a section elevation view of an alternative embodiment of a stabilizer 160 including aspects of the invention, showing in this example an optional pneumatic cable tensioning mechanism. Within the shaft 16, a pneumatic cylinder 2300 is disposed. The pneumatic cylinder 2300 is coupled to the cable 20 by a cable coupler 2302. The cable 20 is tensioned by actuation of the pneumatic cylinder 2300.

Additional Embodiment #9

Figure 43A:
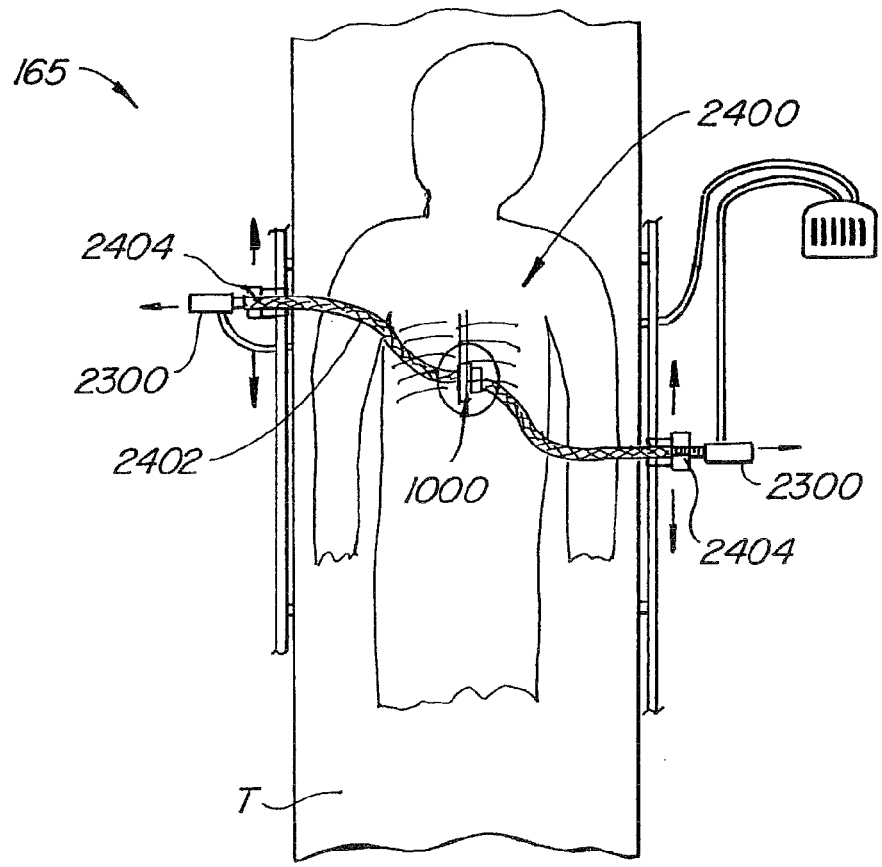
FIGS. 43A-43C illustrate a ninth additional embodiment comprising a positioning and clamping system for a beating heart stabilizer.
Figure 43B:
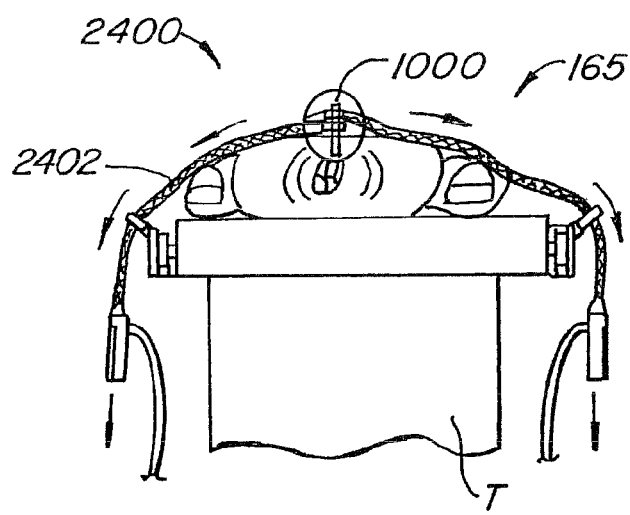

FIGS. 43A-43B are a top view and an end view of one embodiment 165 of the positioning and clamping system for the stabilizer 1000 when used in minimally invasive surgery, optionally robotic surgery. Embodiment 165 is an alternative to the system 170 previously described in relation to FIGS. 6A-6B. The system 165 comprises a linkage of a plurality of lockable-releasable joints which are rigidly fixed to the side rail of an operating table T or similar support. In this embodiments, the system 170 comprises a two-sided, pneumatically actuated system 2400 mountable to the rails of the operating table T. The system 2400 includes conformable members comprising a plurality of tension-cable lockable ball joints 2402. The ball joints 2402 are comprised of balls 37 and intermediate socket rings 37 assembled in the manner as previously described in relation to the ankle 18 and illustrated in FIG. 12A or FIG. 12B. In addition, the joints 2402 function in generally the same way as described in relation to the ankle 18 wherein an internal adjustable tension cable (not shown) is used to apply compressive force upon the sets of ball joints, locking them by internal friction forces, and rendering the linkage rigid. The system 2400 includes an optional pneumatic cable tensioner, as previously described in relation to FIG. 42, attached to the pneumatic cylinder 2300 by a swing latch 2402. Other alternative cable tensioners, optionally be included in the system 2400.

Figure 43C:
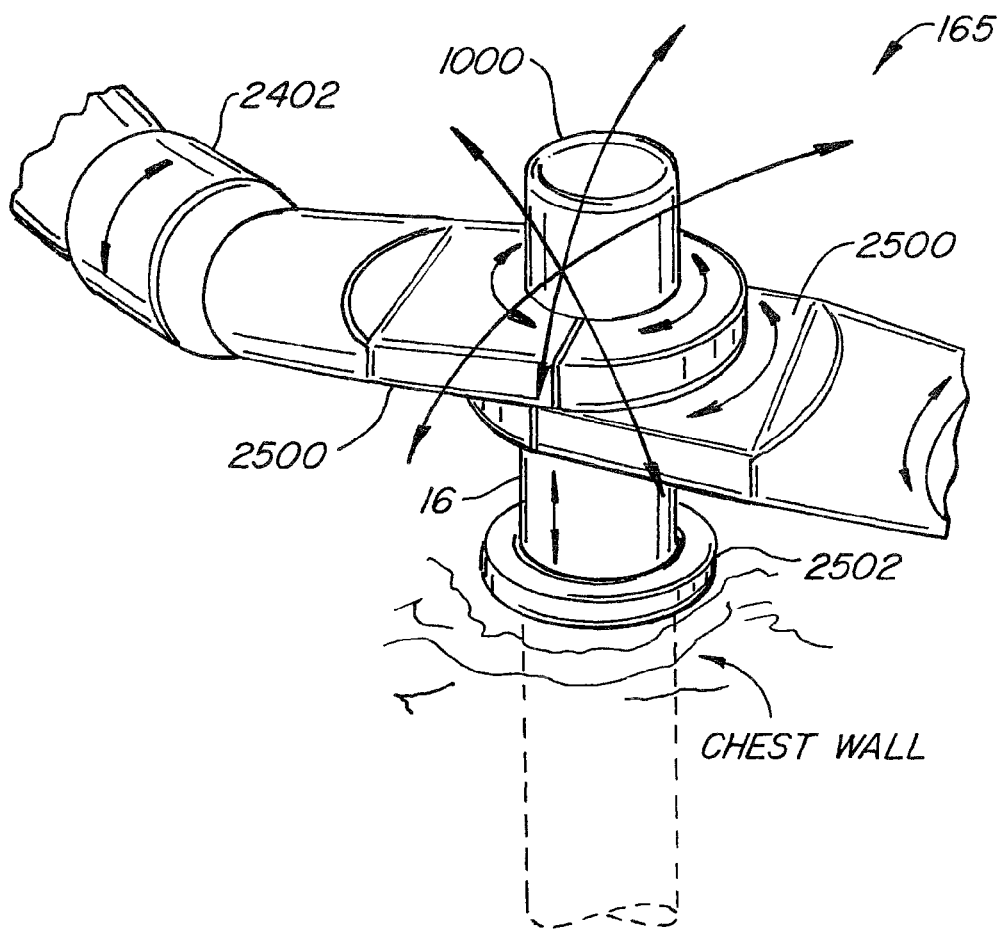

FIG. 43C illustrates how the ball joints 2402 may be joined with the stabilizer 1000 to hold the stabilizer 1000 in place within the chest cavity of the patient. As shown, the ball joints 2402 may be connected with pneumatic clamps 2500. The clamps 2500 are used to clamp the shaft 16 of the stabilizer 1000 as shown. The clamped portion of the shaft 16 is separated from the chest wall by a flange 2502 and any distance of the shaft 16.

It should be noted that although the stabilizer embodiments described above are exemplified as hand-actuated and table mounted systems, the stabilizers of the invention include alternative embodiments mounted to and positioned by robotic systems, such as are described in U.S. patent application Ser. No. 09/436,524 filed Nov. 9, 1999, now issued as U.S. Pat. No. 6,398,726 and also published as corresponding PCT Application WO 00/30551, which are incorporated by reference herein.

For example, the stabilizer embodiments described above may be mounted to the surgical tool interface of such robotic system, and the stabilizer may be positioned and fixed within the body cavity by movements of the robotic servomechanical manipulator. In the stabilizer cable 20 may be tensioned by actuation of a robotically actuated cable tensioner, operated by hydraulic, pneumatic or electromechanical cable retracting devices of known types, which may be mounted to the robotic tool interface.

In addition, robotically actuated stabilizers such as described in WO 00/30551 may additionally include suction mechanisms of the type described herein, the suction tube or lumen being housed within or adjacent the tool shaft and communicating to a suction source (the suction source may be robotically or manually controlled). A flexible portion of the suction lumen may be included adjacent to the robotically actuated wrist-like members, to accommodate wrist motion. Similarly, irrigation mechanisms such as described above may be included in these robotic stabilizer systems.

Thus, while the present invention has been described herein with reference to particular embodiments thereof, a latitude of modification, various changes and substitutions are intended in the foregoing disclosure, and it will be appreciated that in some instances some features of the invention will be employed without a corresponding use of other features without departing from the scope of the invention as set forth. Therefore, many modifications may be made to adapt a particular situation or material to the teachings of the invention without departing from the essential scope and spirit of the present invention. It is intended that the invention not be limited to the particular embodiment disclosed as the best mode contemplated for carrying out this invention but that the invention will include all embodiments and equivalents falling within the scope of the appended claims.

What is claimed is:

1. A method of endoscopically preparing a blood vessel associated with a target tissue for a surgical procedure, said method comprising:
   endoscopically positioning first and second toe portions of a tissue stabilizer against the target tissue to stabilize the tissue while the first and second toe portions straddle the blood vessel so that the first toe portion is positioned on one side of the blood vessel and the second toe portion is positioned on an opposite side of the blood vessel so as not to engage the blood vessel, wherein the tissue stabilizer comprises a shaft sized to allow insertion through an endoscopic cannula and a manipulable foot connected with the shaft, wherein the foot comprises the first toe portion rotatably joined with the second toe portion by a shell, wherein each toe portion comprises at least one suction port to apply suction to the target tissue during stabilization, and wherein the first toe portion and second toe portion are rotatable to a first arrangement wherein the foot is insertable through the endoscopic cannula;
   endoscopically positioning at least one vessel occlusion device around the blood vessel to restrict blood flow therethrough;
   removing the tissue stabilizer from the target tissue while the vessel occlusion device remains in place.

2. A method as in claim 1, further comprising repositioning the tissue stabilizer to a second location against the target tissue while the vessel occlusion device remains in place.

3. A method as in claim 1, wherein the vessel occlusion device comprises a plate-like body having a bore intersecting a radial slot and a flexible member having a free end and fixed end, wherein the fixed end is fixedly attached to the body, and wherein endoscopically positioning at least one vessel occlusion device comprises passing the free end of the flexible member around the blood vessel and into the radial slot so that the member is frictionally held.

4. A method of controlling blood flow in a blood vessel, said method comprising:
   providing a vessel occlusion device comprising
      a plate-like body having a bore intersecting a radial slot, and
      a flexible member having a free end and fixed end, wherein the fixed end is fixedly attached to the body;
   passing the free end of the flexible member around the blood vessel and through the bore so that the blood vessel is encircled by the flexible member and the plate-like body;

pulling the flexible member so that the blood flow is restricted in the blood vessel; and sliding the flexible member into the radial slot so that the member is frictionally held; and inserting a locking pin through a transverse aperture in the plate-like body after sliding the flexible member into the radial slot so that the flexible member is prevented from sliding back into the bore.

5. A method as in claim 4, further comprising:

removing the locking pin from the transverse aperture in the plate-like body; and sliding the flexible member out of the radial slot to release the flexible member so that blood flow through the blood vessel is increased.

6. A method as in claim 4, further comprising:

removing the locking pin from the transverse aperture in the plate-like body; and adjusting the position of the flexible member by sliding the flexible member out of the radial slot and re-sliding the flexible member into the radial slot.

7. A method as in claim 4, further comprising:

providing a tissue stabilizer for endoscopically stabilizing a target tissue within or upon which the blood vessel is disposed; and positioning the tissue stabilizer against the target tissue to stabilize the tissue.

\* \* \* \* \*